US011396670B2

(12) United States Patent
Finnis et al.

(10) Patent No.: US 11,396,670 B2
(45) Date of Patent: *Jul. 26, 2022

(54) PROTEIN EXPRESSION STRAINS

(71) Applicant: Albumedix Ltd, Nottingham (GB)

(72) Inventors: Christopher John Arthur Finnis, Nottingham (GB); Per Kristoffer Nordeide, Copenhagen (DK); Jennifer Mary McLaughlan, Nottingham (GB)

(73) Assignee: Albumedix Limited, Nottingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/464,991

(22) Filed: Sep. 2, 2021

(65) Prior Publication Data

US 2022/0090159 A1 Mar. 24, 2022

Related U.S. Application Data

(63) Continuation of application No. 16/624,616, filed as application No. PCT/EP2018/066344 on Jun. 20, 2018, now Pat. No. 11,130,979.

(30) Foreign Application Priority Data

Jun. 20, 2017 (EP) ..................... 17176932

(51) Int. Cl.
 *C12P 21/00* (2006.01)
 *C12N 9/00* (2006.01)
 *C12N 15/81* (2006.01)

(52) U.S. Cl.
 CPC ................ *C12P 21/00* (2013.01); *C12N 9/93* (2013.01); *C12N 15/81* (2013.01); *C12Y 603/02002* (2013.01)

(58) Field of Classification Search
 CPC .. C12N 15/81; C12N 9/93; C12N 9/00; C12P 21/00
 See application file for complete search history.

(56) References Cited

U.S. PATENT DOCUMENTS

| | | | |
|---|---|---|---|
| 4,302,386 A | 11/1981 | Stevens | |
| 5,223,409 A | 6/1993 | Ladner et al. | |
| 5,728,553 A | 3/1998 | Goodey et al. | |
| 6,159,705 A | 12/2000 | Trueheart et al. | |
| 10,023,618 B2 | 7/2018 | Finnis et al. | |
| 11,130,979 B2* | 9/2021 | Finnis ..................... | C12P 21/00 |
| 2004/0171154 A1 | 9/2004 | Storici et al. | |
| 2018/0009856 A1 | 1/2018 | Finnis et al. | |
| 2020/0157155 A1 | 5/2020 | Finnis et al. | |

FOREIGN PATENT DOCUMENTS

| | | |
|---|---|---|
| CN | 102296033 A | 12/2011 |
| EP | 0319067 A1 | 6/1989 |
| EP | 399455 A2 | 11/1990 |
| EP | 428141 A2 | 5/1991 |
| EP | 0464590 A2 | 1/1992 |
| FR | 2980483 A1 | 3/2013 |
| JP | 2001-501097 A | 1/2001 |
| JP | 2010-029148 A | 2/2010 |
| JP | 2011-103789 A | 6/2011 |
| WO | WO-1990/01063 A1 | 2/1990 |
| WO | WO-1992/04367 A1 | 3/1992 |
| WO | WO-1992/06204 A1 | 4/1992 |
| WO | WO-1992/013951 A1 | 8/1992 |
| WO | WO-1995/17413 A1 | 6/1995 |
| WO | WO-1995/22625 A1 | 8/1995 |
| WO | WO-1996/000787 A1 | 1/1996 |
| WO | WO-1996/37515 A1 | 11/1996 |
| WO | WO-1998/013513 A2 | 4/1998 |
| WO | WO-2000/24883 A1 | 5/2000 |
| WO | WO-2000/44772 A2 | 8/2000 |
| WO | WO-2000/056900 A2 | 9/2000 |
| WO | WO-2003/066824 A2 | 8/2003 |
| WO | WO-2004/009819 A2 | 1/2004 |
| WO | WO-2005/061718 A1 | 7/2005 |
| WO | WO-2006/066595 A2 | 6/2006 |
| WO | WO-2006/067511 A1 | 6/2006 |
| WO | WO-2006/136831 A2 | 12/2006 |
| WO | WO-2009/126920 A2 | 10/2009 |
| WO | WO-2010/059315 A1 | 5/2010 |
| WO | WO-2010/092135 A2 | 8/2010 |
| WO | WO-2010/128142 A1 | 11/2010 |
| WO | WO-2011/051489 A2 | 5/2011 |
| WO | WO-2011/103076 A1 | 8/2011 |
| WO | WO-2011/124718 A1 | 10/2011 |
| WO | WO-2012/059486 A1 | 5/2012 |
| WO | WO-2012/112188 A1 | 8/2012 |
| WO | WO-2012/150319 A1 | 11/2012 |
| WO | WO-2013/075066 A2 | 5/2013 |
| WO | WO-2013/135896 A1 | 9/2013 |
| WO | WO-2014/031831 A1 | 2/2014 |
| WO | WO-2014/072481 A1 | 5/2014 |
| WO | WO-2014/138371 A1 | 9/2014 |
| WO | WO-2014/179657 A1 | 11/2014 |
| WO | WO-2015/036579 A1 | 3/2015 |
| WO | WO-2015/063611 A2 | 5/2015 |
| WO | WO-2017/112847 A1 | 6/2017 |

OTHER PUBLICATIONS

Ayer et al,. The critical role of glutathione in maintenance of the mitochondrial genome. Free Radic Biol Med. Dec. 15, 2010;49(12):1956-68.
Bai et al., The CCR4 and CAF1 proteins of the CCR4-NOT complex are physically and functionally separated from NOT2, NOT4, and NOT5. Mol Cell Biol. Oct. 1999;19(10):6642-51.
Bakti et al., Study on the glutathione metabolism of the filamentous fungus Aspergillus nidulans. Acta Microbiol Immunol Hung. Sep. 1, 2017;64(3):255-272.
Barton et al., Site-directed, recombination-mediated mutagenesis of a complex gene locus. Nucleic Acids Res. Dec. 25, 1990;18(24):7349-55.
Berndsen et al., New insights into ubiquitin E3 ligase mechanism. Nat Struct Mol Biol. Apr. 2014;21(4):301-7.

(Continued)

*Primary Examiner* — Tekchand Saidha
(74) *Attorney, Agent, or Firm* — McCarter & English, LLP; Yu Lu

(57) ABSTRACT

The invention provides an improved host strain for production of desired protein.

24 Claims, 9 Drawing Sheets

Specification includes a Sequence Listing.

(56) References Cited

OTHER PUBLICATIONS

Bhaskar et al., Architecture of the ubiquitylation module of the yeast Ccr4-Not complex. Structure. May 5, 2015;23(5):921-8.

Biterova et al., Mechanistic details of glutathione biosynthesis revealed by crystal structures of *Saccharomyces cerevisiae* glutamate cysteine ligase. J Biol Chem. Nov. 20, 2009;284(47):32700-8.

Biterova et al., Structural basis for feedback and pharmacological inhibition of *Saccharomyces cerevisiae* glutamate cysteine ligase. J Biol Chem. May 7, 2010;285(19):14459-66.

Bowie et al., Identifying determinants of folding and activity for a protein of unknown structure. Proc Natl Acad Sci U S A. Apr. 1989;86(7):2152-6.

Calissano et al., In vivo site-directed mutagenesis of Neurospora crassa beta-tubulin gene by spheroplasts transformation with oligonucleotides. Fungal Genetics Reports. 1996;43:1-3.

Collart et al., NOT1 (CDC39), NOT2(CDC36), NOT3, and NOT4 encode a global-negative regulator of transcription that differentially affects TATA-element utilization. Genes Dev. Mar. 1, 1994;8(5):525-37.

Collart et al., The Ccr4-not complex. Gene. Jan. 15, 2012;492(1):42-53.

Collart, Global control of gene expression in yeast by the Ccr4-Not complex. Gene. Aug. 14, 2003;313:1-16.

Cullen et al., Sequence and centromere proximal location of a transformation enhancing fragment ans1 from Aspergillus nidulans. Nucleic Acids Res. Nov. 25, 1987;15(22):9163-75.

Derbyshire et al., A simple and efficient procedure for saturation mutagenesis using mixed oligodeoxynucleotides. Gene. 1986;46(2-3):145-52.

Dockal et al., The three recombinant domains of human serum albumin. Structural characterization and ligand binding properties. J Biol Chem. Oct. 8, 1999;274(41):29303-10.

Dominguez et al., Structural model of the UbcH5B/CNOT4 complex revealed by combining NMR, mutagenesis, and docking approaches. Structure. Apr. 2004;12(4):633-44.

Ebi, PA No. CP004800.2. *Saccaromyces cerevisiae* YJM1252 Mot2p. 2 pages, Jun. 23, 2016.

Edgar, Muscle: multiple sequence alignment with high accuracy and high throughput. Nucleic Acids Res. Mar. 19, 2004;32(5):1792-7.

Finnis et al., High-level production of animal-free recombinant transferrin from *Saccharomyces cerevisiae*. Microbial Cell Factories. Nov. 17, 2010;9(87):1-11.

Finnis et al., Thymidine phosphorylase activity of platelet-derived endothelial cell growth factor is responsible for endothelial cell mitogenicity. Eur J Biochem. Feb. 15, 1993;212(1):201-10.

Fleer et al., Stable multicopy vectors for high-level secretion of recombinant human serum albumin by *Kluyveromyces* yeasts. Biotechnology (N Y). Oct. 1991;9(10):968-75.

Franklin et al., Structure, function, and post-translational regulation of the catalytic and modifier subunits of glutamate cysteine ligase. Mol Aspects Med. Feb.-Apr. 2009;30(1-2):86-98.

Gasser et al., Protein folding and conformational stress in microbial cells producing recombinant proteins: a host comparative overview. Microbial Cell Factories. 2008;7(11):1-18.

Gems et al., An autonomously replicating plasmid transforms Aspergillus nidulans at high frequency. Gene. Feb. 1, 1991;98(1):61-7.

GenBank Accession No. 1HK3_A, Chain A, Human Serum Albumin Mutant R218p Complexed With Thyroxine (3,3',5,5'-Tetraiodo-L-Thyronine). 3 pages, Oct. 10, 2012.

GenBank Accession No. AAA98797, albumin [*Homo sapiens*]. May 3, 1996. 2 pages.

GenBank Accession No. ACF10391, albumin precursor, partial [*Capra hircus*]. Jul. 26, 2016. 2 pages.

GenBank Accession No. AJU45621, Mot2p [*Saccharomyces cerevisiae* YJM1252]. Mar. 16, 2016. 3 pages.

GenBank Accession No. NP_010991, CCR4-NOT core ubiquitin-protein ligase subunit MOT2 [*Saccharomyces cerevisiae* S288c]. 2 pages, Aug. 22, 2014.

GenBank ID No. AJU42819, *Saccharomyces cerevisiae* YJM1129 Mot2p. Apr. 20, 2015. 2 pages.

GenBank ID No. AJU38337, *Saccharomyces cerevisiae* YJM984 Irc5p. Jan. 25, 2017. 3 pages.

GenBank ID No. AJU52240, *Saccharomyces cerevisiae* YJM1418 Mot2p. Jul. 28, 2016. 2 pages.

Grant et al., Glutathione is an essential metabolite required for resistance to oxidative stress in the yeast *Saccharomyces cerevisiae*. Curr Genet. 1996;29:511-515.

Grant et al., Glutathione synthetase is dispensable for growth under both normal and oxidative stress conditions in the yeast *Saccharomyces cerevisiae* due to an accumulation of the dipeptide gamma-glutamylcysteine. Mol Biol Cell. Sep. 1997;8(9):1699-707.

Guo et al., 3'-end-forming signals of yeast mRNA. Mol Cell Biol. Nov. 1995;15(11):5983-90.

Gutiérrez-Escobedo et al., Role of glutathione in the oxidative stress response in the fungal pathogen Candida glabrata. Curr Genet. Aug. 2013;59(3):91-106.

Hara et al., Improvement of oxidized glutathione fermentation by thiol redox metabolism engineering in *Saccharomyces cerevisiae*. Appl Microbiol Biotechnol. Nov. 2015;99(22):9771-8.

Hatem et al., Glutathione is essential to preserve nuclear function and cell survival under oxidative stress. Free Radic Biol Med. Feb. 2014;67:103-14.

Hatem et al., Glutathione is essential to preserve nuclear function and cell survival under oxidative stress. Free Radical Biology and Medicine. 2014;75:S25, Poster P14.

Hawksworth et al., Ainsworth & Bisby's Dictionary of The Fungi, Eighth Edition. International Mycological Institute. CAB International, Wallingford. p. 171, (1995).

Hoefs, Globulin correction of the albumin gradient: correlation with measured serum to ascites colloid osmotic pressure gradients. Hepatology. Aug. 1992;16(2):396-403.

Irie et al., The yeast MOT2 gene encodes a putative zinc finger protein that serves as a global negative regulator affecting expression of several categories of genes, including mating-pheromone-responsive genes. Mol Cell Biol. May 1994;14(5):3150-7.

Katoh et al., MAFFT version 5: improvement in accuracy of multiple sequence alignment. Nucleic Acids Res. Jan. 20, 2005;33(2):511-8.

Katoh et al., MAFFT: a novel method for rapid multiple sequence alignment based on fast Fourier transform. Nucleic Acids Res. Jul. 15, 2002;30(14):3059-66.

Katoh et al., Multiple Alignment of DNA Sequences with MAFFT. Bioinformatics for DNA Sequence Analysis, Methods in Molecular Biology. David Posada (Ed.). Humana Press. Chapter 3, pp. 39-64 (2009).

Katoh et al., Parallelization of the MAFFT multiple sequence alignment program. Bioinformatics. Aug. 1, 2010;26(15):1899-900.

Katoh et al., PartTree: an algorithm to build an approximate tree from a large number of unaligned sequences. Bioinformatics. Feb. 1, 2007;23(3):372-4.

Kelly et al., *Escherichia coli* gamma-glutamylcysteine synthetase. Two active site metal ions affect substrate and inhibitor binding. J Biol Chem. Jan. 4, 2002;277(1):50-8.

Kerry-Williams et al., Disruption of the *Saccharomyces cerevisiae* YAP3 gene reduces the proteolytic degradation of secreted recombinant human albumin. Yeast. Jan. 30, 1998;14(2):161-9.

Kistler et al., Genetic and biochemical analysis of glutathione-deficient mutants of *Saccharomyces cerevisiae*. Mutagenesis. Jan. 1990;5(1):39-44.

Kjeldsen et al., Secretory expression of human albumin domains in *Saccharomyces cerevisiae* and their binding of myristic acid and an acylated insulin analogue. Protein Expr Purif. Jul. 1998;13(2):163-9.

Kobayashi et al., The development of recombinant human serum albumin. Ther Apher. Nov. 1998;2(4):257-62.

Kragh-Hansen et al., Practical aspects of the ligand-binding and enzymatic properties of human serum albumin. Biol Pharm Bull. Jun. 2002;25(6):695-704.

Kren et al., In vivo site-directed mutagenesis of the factor IX gene by chimeric RNA/DNA oligonucleotides. Nat Med. Mar. 1998;4(3):285-90.

(56) References Cited

OTHER PUBLICATIONS

Kruk et al., The multifunctional Ccr4-Not complex directly promotes transcription elongation. Genes Dev. Mar. 15, 2011;25(6):581-93.
Lee et al., The essential and ancillary role of glutathione in *Saccharomyces cerevisiae* analysed using a grande gsh1 disruptant strain. FEMS Yeast Res. Apr. 2001;1(1):57-65.
Lodi et al., Secretion of human serum albumin by Kluyveromyces lactis overexpressing KlPDI1 and KlERO1. Appl Environ Microbiol. Aug. 2005;71(8):4359-63.
Lowman et al., Selecting high-affinity binding proteins by monovalent phage display. Biochemistry. Nov. 12, 1991;30(45):10832-8.
Maris et al., Glutathione, but not transcription factor Yap1, is required for carbon source-dependent resistance to oxidative stress in *Saccharomyces cerevisiae*. Curr Genet. Mar. 2000;37(3):175-82.
Mazzoni et al., The inactivation of KlNOT4, a Kluyveromyces lactis gene encoding a component of the CCR4-NOT complex, reveals new regulatory functions. Genetics. Jul. 2005;170(3):1023-32.
Miller et al., Ccr4-Not complex: the control freak of eukaryotic cells. Crit Rev Biochem Mol Biol. Jul.-Aug. 2012;47(4):315-33.
Minghetti et al., Molecular structure of the human albumin gene is revealed by nucleotide sequence within q11-22 of chromosome 4. J Biol Chem. May 25, 1986;261(15):6747-57.
Mortimer et al., Genealogy of principal strains of the yeast genetic stock center. Genetics. May 1986;113(1):35-43.
Murray et al., Unexpected divergence and molecular coevolution in yeast plasmids. J Mol Biol. Apr. 5, 1988;200(3):601-7.
Nardi et al., Assay of gamma-glutamylcysteine synthetase and glutathione synthetase in erythrocytes by high-performance liquid chromatography with fluorimetric detection. J Chromatogr. Aug. 24, 1990;530(1):122-8.
NCBI Accession No. XP_517233, Predicted: serum albumin [Pan troglodytes]. Jun. 2, 2016. 2 pages.
Needleman et al., A general method applicable to the search for similarities in the amino acid sequence of two proteins. J Mol Biol. Mar. 1970;48(3):443-53.
Neilsen et al., Production of biopharmaceutical proteins by yeast. Jul./Aug. 2013. Bioengineered. vol. 4, No. 4, p. 207-211.
Ner et al., A simple and efficient procedure for generating random point mutations and for codon replacements using mixed oligodeoxynucleotides. DNA. Mar. 1988;7(2):127-34.
Ness et al., DNA shuffling of subgenomic sequences of subtilisin. Nat Biotechnol. Sep. 1999;17(9):893-6.
Ohtake et al., Molecular cloning of the gamma-glutamylcysteine synthetase gene of *Saccharomyces cerevisiae*. Yeast. Dec. 1991;7(9):953-61.
Painting et al., A note on the presence of novel DNA species in the spoilage yeasts *Zygosaccharomyces bailii* and *Pichia membranaefaciens*. J Appl Bacteriol. Apr. 1984;56(2):331-5.
Penninckx, A short review on the role of glutathione in the response of yeasts to nutritional, environmental, and oxidative stresses. Enzyme Microb Technol. Jun. 1, 2000;26(9-10):737-742.
Preissler et al., Not4-dependent translational repression is important for cellular protein homeostasis in yeast. EMBO J. Jul. 14, 2015;34(14):1905-24.
Pócsi et al., Glutathione, altruistic metabolite in fungi. Adv Microb Physiol. 2004;49:1-76.
Reidhaar-Olson et al., Combinatorial cassette mutagenesis as a probe of the informational content of protein sequences. Science. Jul. 1, 1988;241(4861):53-7.
Rice et al., EMBOSS: the European Molecular Biology Open Software Suite. Trends Genet. Jun. 2000;16(6):276-7.
Romanos et al., Foreign gene expression in yeast: a review. Yeast. Jun. 1992;8(6):423-88.
Scherer et al., Replacement of chromosome segments with altered DNA sequences constructed in vitro. Proc Natl Acad Sci U S A. Oct. 1979;76(10):4951-5.
Skinner et al., Biology and Activities of Yeasts. Academic Press, London. Table of Contents. 7 pages (1980).

Sleep et al., Albumin and its application in drug delivery. Expert Opin Drug Deliv. May 2015;12(5):793-812.
Sleep et al., The secretion of human serum albumin from the yeast *Saccharomyces cerevisiae* using five different leader sequences. Biotechnology (N Y). Jan. 1990;8(1):42-6.
Spector et al., A genetic investigation of the essential role of glutathione: mutations in the proline biosynthesis pathway are the only suppressors of glutathione auxotrophy in yeast. J Biol Chem. Mar. 9, 2001;276(10):7011-6.
Storici et al., In vivo site-directed mutagenesis using oligonucleotides. Nat Biotechnol. Aug. 2001;19(8):773-6.
Tang et al., Three-pathway combination for glutathione biosynthesis in *Saccharomyces cerevisiae*. Microb Cell Fact. Sep. 16, 2015;14:139.
Thompson et al., CLUSTAL W: improving the sensitivity of progressive multiple sequence alignment through sequence weighting, position-specific gap penalties and weight matrix choice. Nucleic Acids Res. Nov. 11, 1994;22(22):4673-80.
Tian et al., Accurate multiplex gene synthesis from programmable DNA microchips. Nature. Dec. 23, 2004;432(7020):1050-4.
UniProtKB—P02768 (Albu_Human). 31 pages. Apr. 25, 2018.
UniProtKB/Swiss-Prot Accession No. O35090, RecName: Full= Serum albumin; Flags: Precursor. Nov. 2, 2016. 6 pages.
UniProtKB/Swiss-Prot Accession No. P02768, RecName: Full= Serum albumin; Flags: Precursor. Nov. 2, 2016. 57 pages.
UniProtKB/Swiss-Prot Accession No. P02769, RecName: Full= Serum albumin; AltName: Full=BSA; AltName: Allergen=Bos d 6; Flags: Precursor. Nov. 2, 2016. 13 pages.
UniProtKB/Swiss-Prot Accession No. P02770, RecName: Full= Serum albumin; Flags: Precursor. Nov. 2, 2016. 8 pages.
UniProtKB/Swiss-Prot Accession No. P07724, RecName: Full= Serum albumin; Flags: Precursor. Nov. 2, 2016. 10 pages.
UniProtKB/Swiss-Prot Accession No. P08835, RecName: Full= Serum albumin; Flags: Precursor. Nov. 2, 2016. 6 pages.
UniProtKB/Swiss-Prot Accession No. P14639, RecName: Full= Serum albumin; Flags: Precursor. Nov. 2, 2016. 10 pages.
UniProtKB/Swiss-Prot Accession No. P19121, RecName: Full= Serum albumin; AltName: Full=Alpha-livetin; AltName: Allergen= Gal d 5; Flags: Precursor. Nov. 2, 2016. 5 pages.
UniProtKB/Swiss-Prot Accession No. P35747, RecName: Full= Serum albumin; AltName: Allergen=Equ c 3; Flags: Precursor. Nov. 2, 2016. 10 pages.
UniProtKB/Swiss-Prot Accession No. P49064. RecName: Full= Serum albumin; AltName: Allergen=Fel d 2; Flags: Precursor. Nov. 2, 2016. 7 pages.
UniProtKB/Swiss-Prot Accession No. P49065, RecName: Full= Serum albumin; Flags: Precursor. Nov. 2, 2016. 10 pages.
UniProtKB/Swiss-Prot Accession No. P49822, RecName: Full= Serum albumin; AltName: Allergen=Can f 3; Flags: Precursor. Nov. 2, 2016. 7 pages.
UniProtKB/Swiss-Prot Accession No. Q28522, RecName: Full= Serum albumin; Flags: Precursor. Nov. 2, 2016. 6 pages.
UniProtKB/Swiss-Prot Accession No. Q5XLE4, RecName: Full= Serum albumin; Flags: Precursor. Nov. 2, 2006. 6 pages.
UniProtKB/Swiss-Prot Accession No. Q6WDN9, Preproalbumin precursor. Nov. 28, 2006. 1 page.
UniProtKB/Swiss-Prot Accession No. Q95VB7, Albumin. Oct. 31, 2006. 1 page.
Valkonen et al., Effects of inactivation and constitutive expression of the unfolded-protein response pathway on protein production in the yeast *Saccharomyces cerevisiae*. Appl Environ Microbiol. Apr. 2003;69(4):2065-72.
Volkert et al., Deoxyribonucleic acid plasmids in yeasts. Microbiol Rev. Sep. 1989;53(3):299-317.
Volohonsky et al., A spectrophotometric assay of gamma-glutamylcysteine synthetase and glutathione synthetase in crude extracts from tissues and cultured mammalian cells. Chem Biol Interact. Apr. 20, 2002;140(1):49-65.
Watanabe et al., Purification and Characterization of gamma-Glutamylcysteine Synthetase of *Escherichia coli* B. Agric Biol Chem. 1986;50(8):1925-1930.
Wheeler et al., Glutathione regulates the expression of gamma-glutamylcysteine synthetase via the Met4 transcription factor. Molecular Microbiology. 2002;2:545-556.

(56) References Cited

OTHER PUBLICATIONS

WPI, Accession No. 2012-A72980, New delta-gamma-glutamylcyssteine synthetase 1 (gsh1) deletion mutant strain of *Saccaromyces cerevisiae* deposited under CCTCC No. M 2011130, useful for detecting toxicity of cadmium chloride and other heavy metals. 2 pages, (2017).

Xu et al., Effects of GSH1 and GSH2 Gene Mutation on Glutathione Synthetases Activity of *Saccharomyces cerevisiae*. Protein J. Aug. 2017;36(4):270-277.

Yamaguchi et al., Homology modeling and structural analysis of human gamma-glutamylcysteine ligase catalytic subunit for antitumor drug development. Journal of Biophysical Chemistry. 2012;3(3):238-248.

Yang et al., Interaction between the catalytic and modifier subunits of glutamate-cysteine ligase. Biochem Pharmacol. Jul. 15, 2007;74(2):372-81.

International Search Report and Written Opinion for Application No. PCT/EP2018/066344, dated Jul. 30, 2018, 14 pages.

International Search Report and Written Opinion for Application No. PCT/US2016/068239, dated Mar. 10, 2017, 12 pages.

Azzouz et al., Specific roles for the Ccr4-Not complex subunits in expression of the genome. RNA. Mar. 2009;15(3):377-83.

Blessing, The role of Not4 in cellular homeostasis during proliferation and differentiation in *Saccharomyces cerevisiae*. Dissertation zur Erlangung des akademischen Grades eines Doktors der Naturwissenschaften. 168 pages, (2018).

U.S. Appl. No. 15/593,549, filed May 12, 2017, U.S. Publication No. 2018-0009856, Abandoned.

U.S. Appl. No. 15/677,164, filed Aug. 15, 2017, U.S. Pat. No. 10,023,618, Issued.

U.S. Appl. No. 16/415,187, filed May 17, 2019, U.S. Publication No. 2020-0157155, Published.

U.S. Appl. No. 16/624,616, filed Dec. 19, 2019, U.S. Pat. No. 11,130,979, Issued.

\* cited by examiner

PROTEIN EXPRESSION STRAINS

REFERENCE TO RELATED APPLICATIONS

This application is a continuation of U.S. application Ser. No. 16/624,616, filed on Dec. 19, 2019, which is a U.S. national stage application filed under U.S.C. § 371, based on International Patent Application No. PCT/EP2018/066344, filed on Jun. 20, 2018, which claims priority to EP Application No. 17176932.6, filed on Jun. 20, 2017. The entire contents of each of the foregoing applications, including all drawings and sequence listings, are hereby incorporated herein by reference.

REFERENCE TO SEQUENCE LISTING

The instant application contains a Sequence Listing which has been submitted electronically in ASCII format and is hereby incorporated by reference in its entirety. Said ASCII copy, created on Sep. 1, 2021, is named 127042-11502_SeqListing.TXT and is 129,239 bytes in size.

FIELD OF THE INVENTION

This invention relates primarily to the development of fungal strains which express proteins at levels substantially higher than the parental strains.

BACKGROUND OF THE INVENTION

For some 30 years, desired heterologous proteins have been produced in microorganisms. However, having introduced the necessary coding sequence and obtained expression, much still remains to be done in order to optimise the process for commercial production. One area of interest concerns strain improvement, that is to say finding or making strains of the host microorganism which enable the protein to be made in higher yields or better purity, for example.

To increase the yield, once a good expression system has been devised, one might envisage trying to increase the copy number of the coding sequence, or to increase the quantity or stability of the mRNA, or to improve folding and/or secretion of the protein or to decrease the degradation of the protein. However, the desired effect of increased expression will only be seen if the limiting factor(s) is targeted.

Therefore, what is required is a host strain which allows the yield of a desired protein, such as a heterologous protein, to be increased.

The inventors have surprisingly identified that mutation of GSH1 in a fungal cell results in such an increased yield of heterologous protein.

The product of the GSH1 gene in *Saccharomyces cerevisiae* is γ-glutamylcysteine synthetase (Gsh1p). This enzyme catalyses the first, and rate-limiting, step in the synthesis of glutathione (L-γ-glutamylcysteinylglycine; GSH). The second step is catalysed by glutathione synthetase (Gsh2p). Glutathione is an essential molecule which has many important roles including protecting cells against oxidative stress, as a cofactor in several biosynthesis pathways and detoxification reactions, and maintenance of the yeast mitochondrial genome (Ayer et al (2010) Free Radical Biology & Medicine 49 1956-1968)). Yeast cells deleted for the GSH1 gene, unless grown in media containing glutathione, are hypersensitive to a range of stress conditions, such as oxidative conditions and exposure to heavy metals and they eventually undergo growth arrest (Spector et al (2001) The Journal of Biological Chemistry 276 (10) 7011-7016). Glutathione is also known to protect the nucleus at times of oxidative stress (Hatem et al (2014) Free Radical Biology & Medicine 67 103-114). Biterova and Barycki (2009) (The Journal of Biological Chemistry 284, 32700-32708) analyzed crystal structures of Ghs1 (also known as glutamate cysteine ligase) to investigate the mechanism of glutathione biosynthesis, and state that variants of human glutamate cysteine ligase have been observed (e. g. R127C, P158L, H370L and P414L).

Previously (PCT/US2016/068239), it was identified that mutation of NOT4 (also known as MOT2) results in an increased yield of heterologous protein produced in a host strain. The inventors have now identified that combining the NOT4 and GSH1 mutations surprisingly results in a further increase in yield.

Not4 is a ubiquitin-ligating enzyme and is part of the Ccr4-Not complex. The Ccr4-Not complex is conserved in eukaryotic cells, and in yeast the complex consists of 9 core subunits: Ccr4, Caf1, Caf40, Caf130, Not1, Not2, Not3, Not4 and Not5 (Collart, 2003, Global control of gene expression in yeast by the Ccr4-Not complex. *Gene* 313: 1-16; Bai et al, 1999, The CCR4 and Caf1 proteins of the Ccr4-Not complex are physically and functionally separated from Not2, Not4, and Not5. *Mol. Cell. Biol.* 19: 6642-6651). The complex has been proposed to function as a central switchboard that can interpret signals from the environment and coordinate all levels of gene expression to economically respond to the signal (Collart, 2012, The Ccr4-Not complex. *Gene* 492(1): 42-53). It is thought that Not proteins (Not1, Not2, Not3, Not4) are necessary for assembly of the RNA polymerase II complex, which suggests a global role in transcription regulation (Collart, 1994, Not1 (cdc39), Not2 (cdc36), Not3, and Not4 encode a global-negative regulator of transcription that differentially affects tata-element utilization. *Genes & Development* 8(5): 525-537; Collart, 2012, as cited above). A co-crystal structure suggested how the C-terminal region of Not4 wraps around a HEAT-repeat region of Not1, the scaffold protein in the Ccr4-Not complex (Bhaskar, 2015, Architecture of the ubiquitylation module of the yeast Ccr4-Not complex. *Structure* 23(5): 921-8).

SUMMARY OF THE INVENTION

The invention provides a fungal host cell having:
a. a modified Gsh1 protein or homolog thereof, and/or
b. a modified activity level of Gsh1 protein or homolog thereof, and/or
c. a modified GSH1 gene or homolog thereof, and/or
d. a modified level of expression of GSH1 gene or homolog thereof.

The invention also provides a fungal host cell further having:
e. a modified Not4 protein or homolog thereof, and/or
f. a modified activity level of Not4 protein or homolog thereof, and/or
g. a modified NOT4 gene or homolog thereof, and/or
h. a modified level of expression of NOT4 gene or homolog thereof.

The invention also provides a culture of fungal host cells containing a polynucleotide sequence encoding a desired protein, such as a heterologous protein, characterised in that the fungal host cells have a reduced activity level and/or expression level of Gsh1 protein of homolog thereof, and optionally further having a reduced activity level and/or expression level of Not4 protein or homolog thereof.

The invention further provides a method for producing a desired protein, such as a heterologous protein, from a fungal host cell.

The invention provides a method for modifying the production yield of a desired polypeptide from a fungal host cell.

The invention also provides a desired protein, such as a heterologous protein. Albumin or variant, fragment, and/or fusion thereof is a preferred desired protein.

The invention further provides a composition, such as a pharmaceutical composition, comprising the desired protein.

The invention also provides a method of treating a patient comprising administering an effective amount of the composition to the patient.

The invention further provides a method of preparing a fungal host cell having the above mentioned property or properties.

The invention also provides a Gsh1 protein or homolog thereof comprising at least 50% identity to SEQ ID NO: 2 and a mutation at a position corresponding to one or more positions selected from 47, 48, 49, 50, 51, 120, 121, 122, 123, 124, 125, 126, 127, 128, 129, 130, 409, 451, 452, 453, 454 and 455 of SEQ ID NO: 2.

The invention further provides a polynucleotide encoding a Gsh1 variant of the present invention.

Any embodiments described herein, including those described only in the examples and/or the Preferred Embodiments section, are intended to be able to combine with any other embodiments, unless explicitly disclaimed or the combination is improper.

DEFINITIONS

Figure 1:
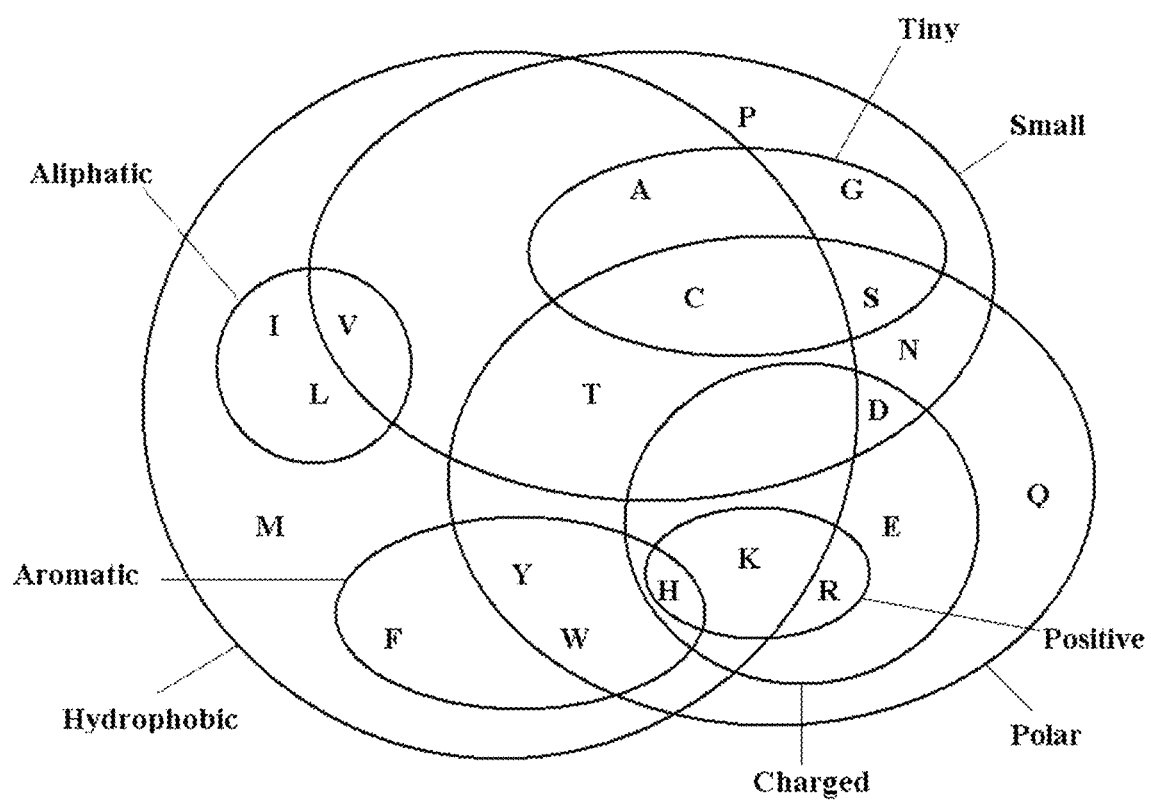
FIG. 1 is a Venn diagram showing the classes of and relationship between twenty amino acids.

Albumin: The term "albumin" means a protein having the same and/or very similar tertiary structure as human serum albumin (HSA) or HSA domains and has similar properties to HSA or the relevant domains. Similar tertiary structures are, for example, the structures of the albumins from the species mentioned under "parent albumin". Some of the major properties of albumin are i) its ability to regulate plasma volume (oncotic activity), ii) a long plasma half-life of around 19 days±5 days, iii) binding to gp60, also known as albondin iv) binding to FcRn, v) ligand-binding, e.g. binding of endogenous molecules such as acidic, lipophilic compounds including bilirubin, fatty acids, hemin and thyroxine (see also Table 1 of Kragh-Hansen et al, 2002, Biol. Pharm. Bull. 25, 695, hereby incorporated herein by reference), vi) binding of small organic compounds with acidic or electronegative features e.g. drugs such as warfarin, diazepam, ibuprofen and paclitaxel (see also Table 1 of Kragh-Hansen et al, 2002, Biol. Pharm. Bull. 25, 695, hereby incorporated herein by reference). Not all of these properties need to be fulfilled to characterize a protein or fragment as an albumin. If a fragment, for example, does not comprise a domain responsible for binding of certain ligands or organic compounds the variant of such a fragment will not be expected to have these properties either.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, pro-peptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression cassette: The term "expression cassette" means the polynucleotide encoding a polypeptide and the upstream and downstream control sequences that provide for its expression.

Expression host: The term "expression host" means any host cell that expresses a desired protein, particularly a heterologous protein.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (several) amino acids deleted from the amino and/or carboxyl terminus of a mature polypeptide and/or from an internal region of a mature polypeptide. Fragments may consist of one uninterrupted sequence derived from a polypeptide or may comprise two or more sequences derived from different parts of the polypeptide. With respect to albumin, a fragment may have a size of more than approximately 20 amino acid residues, preferably more than 30 amino acid residues, more preferred more than 40 amino acid residues, more preferred more than 50 amino acid residues, more preferred more than 75 amino acid residues, more preferred more than 100 amino acid residues, more preferred more than 200 amino acid residues, more preferred more than 300 amino acid residues, even more preferred more than 400 amino acid residues and most preferred more than 500 amino acid residues. In a preferred embodiment, a fragment corresponds to one or more of the albumin domains. Preferred albumin domains of the invention are domains having at least 70, 75, 80, 85, 90, 95, 96, 97, 98, 99, 99.5% or 100% identity to a HSA domain I consisting of amino acid residues 1 to 194±1 to 15 amino acids of SEQ ID NO: 10; at least 70, 75, 80, 85, 90, 95, 96, 97, 98, 99, 99.5% or 100% identity to HSA domain II consisting of amino acid residues 192 to 387±1 to 15 amino acids of SEQ ID NO: 10 and at least 70, 75, 80, 85, 90, 95, 96, 97, 98, 99, 99.5% or 100% identity to HSA domain III consisting of amino acid residues 381 to 585±1 to 15 amino acids of SEQ ID NO: 10 or a combination of one or more (several) of these domains, e.g. domain I and II, domain II and III or domain I and III fused together. No generally accepted convention for the exact borders of the albumin domains exists and the overlap in the above mentioned ranges and the allowance of a varying length of plus or minus 1, 2, 3, 4, 5, 6, 7, 8, 9, 10, 11, 12, 13, 14 or 15 from amino acids, preferably from 1 to 15 amino acids, more preferably from 1 to 10 amino acids, most preferably from 1 to 5 amino acids, at the N-terminal and/or C-terminal of the domains, allowing for a total variance in length of up to 30 amino acids, preferably up to 20 amino acids, more preferably up to 10 amino acids for each domain reflects this fact and that there may be some diverging opinions on the amino acid residues in the border between the domains belonging to one or the other domain. For the same reason, it may be possible to find references to the amino acid residues of albumin domains that diverge from the numbers above, however, the skilled person will appreciate how to identify the albumin domains based on the teaching in the literature and the teaching above. Corresponding domains of non-human albumins can be identified by alignment with HSA using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later, more preferably version 5.0.0 or later. The optional parameters used are gap open penalty of 10, gap extension penalty of 0.5, and the EBLOSUM62 (EMBOSS version of BLOSUM62) substitution matrix. Alternative alignment tools can also be used, for example MUSCLE as described herein. The domains may also be defined according to Dockal or Kjeldsen: Dockal et al (The Journal of Biological Chemistry, 1999, Vol. 274(41): 29303-29310) defines the domains of HSA as: Domain I: amino acids 1 to 197, Domain II: amino acids 189 to 385 of SEQ ID NO: 10, Domain III: amino acids 381 to 585 of SEQ ID NO: 10 Kjeldsen et al (Protein Expression and Purification, 1998, Vol 13: 163-169) defines the domains as: Domain I: amino acids 1 to 192, Domain II: amino acids 193 to 382, Domain III: amino acids 383 to 585. Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511.

Therefore, in this invention, the following domain definitions are preferred. The amino acid numbers correspond to those of SEQ ID NO: 10 (HSA). However, using these numbers, the skilled person can identify corresponding domains in other albumin sequences. Domain I may or may not start at amino acid 1 and may or may not end at any of amino acids 192, 193, 194, 195, 196 or 197, preferably any of amino acids 192, 194 or 197. Domain II may or may not start at amino acid 189, 190, 191, 192 or 193, preferably any of amino acids 189, 192 or 193, and may or may not end at amino acid 382, 383, 384, 385, 386 or 387, preferably any of amino acids 382, 285 or 387. Domain III may or may not start at amino acid 381, 382 or 383, preferably amino acid 381 or 383, and may or may not end at amino acid 585. Domains in non-human albumins may have the same or different amino acid lengths and/or residue numbers as HSA. For example, a multiple alignment or pair-wise alignment may be prepared using HSA and one or more (several) other albumins, fragments, derivatives, variants and/or fusions in order to identify domains corresponding to domains I, II and/or III of HSA.

Fusion partner: Throughout this specification, a fusion partner is a non-albumin moiety which may be genetically fused to an albumin or variant and/or fragment thereof.

Heterologous protein: a heterologous protein is one not naturally produced by the host cell and, preferably, does not include proteins such as selection markers (e.g. antibiotic resistance markers, auxotrophic selectable markers), chaperones, FLP, REP1, or REP2.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Mature polypeptide: The term "mature polypeptide" means a polypeptide in its final form following translation and any post-translational modifications, such as N-terminal processing, C-terminal truncation, glycosylation, phosphorylation, etc. The mature sequence of human albumin is provided in SEQ ID NO: 10, while an example of an immature form is provided in SEQ ID NO: 12.

Mature polypeptide coding sequence: The term "mature polypeptide coding sequence" means a polynucleotide that encodes a mature polypeptide. An example of a mature polypeptide coding sequence of human albumin is provided in SEQ ID NO: 9, while an example of a coding sequence for an immature form of human albumin is provided in SEQ ID NO: 11.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide, such that the control sequence directs expression of the coding sequence.

Parent or Parent Albumin: The term "parent" or "parent albumin" means an albumin to which an alteration is made to produce the albumin variants of the present invention. The parent may be a naturally occurring (wild-type) polypeptide or an allele thereof or a variant thereof. In a preferred embodiment, the parent albumin is a wild-type albumin, more preferably a wild-type albumin from *Homo sapiens* as disclosed in SEQ ID NO: 12 (UNIPROT: P02768.2) or the mature sequence thereof (SEQ ID NO: 10). Alternative wild-type albumins can be selected from the non-exhaustive list shown in Table 1.

TABLE 1

Wild-type albumins from various species.

| Common Name | Species | SwissProt or GenBank Accession No | % Identity to SEQ ID NO: 10* | Length (aa) |
|---|---|---|---|---|
| Human | *Homo sapiens* | P02768.2 | 100.0 | 609 |
| Chimpanzee | *Pan troglodytes* | XP_517233 (predicted sequence) | 98.8 | 609 |
| Sumatran Orangutan | *Pongo abelii* | Q5NVH5.2 | 98.5 | 609 |
| Macaque (Rhesus Monkey) | *Macaca mulatta* | Q28522.1 | 93.3 | 600 |
| Cat | *Felis catus* | P49064.1 | 81.9 | 608 |
| Dog | *Canis lupus familiaris* | P49822.3 | 80.0 | 608 |
| Donkey | *Equus asinus* | Q5XLE4.1 | 76.7 | 607 |
| Horse | *Equus caballus* | P35747.1 | 76.3 | 607 |
| Blood fluke | *Schistosoma mansoni* | Q95VB7 | 76.2 | 608 |
| Bovine | *Bos taurus* | P02769.4 (NP_851335.1) | 75.6 | 607 |
| Pig | *Sus scrota* | P08835.2 | 75.1 | 607 |
| Sheep | *Ovis aries* | P14639.1 | 75.0 | 607 |
| Goat | *Capra hircus* | ACF10391.1 | 74.8 | 607 |
| Rabbit | *Oryctolagus cuniculus* | P49065.2 | 74.3 | 608 |
| Mongolian Gerbil | *Meriones unguiculatus* | O35090.1 | 73.6 | 609 |
| Rat | *Rattus norvegicus* | P02770. 2. | 73.3 | 608 |
| Mouse | *Mus musculus* | P07724.3. | 72.3 | 608 |
| Guinea Pig | *Cavia porcellus* | Q6WDN9 | 72.1 | 608 |
| Chicken | *Gallus gallus* | P19121.2 | 47.0 | 615 |

*Sequence identity was calculated using the Needleman-Wunsch algorithm as implemented in the Needle program of EBLOSUM62 (EMBOSS suite of programs, version 6.1.0) using gap open penalty of 10, gap extension penalty of 0.5 as described herein.

Preferably the parent albumin is a mature albumin. In another embodiment, the parent albumin is at least 70%, more preferably 75%, more preferably at least 80%, more preferably at least 85%, even more preferably at least 90%, most preferably at least 95%, at least 96%, at least 97%, at least 98%, at least 99% at least 99.5% or at least 99.8% identical to SEQ ID NO: 10, and maintains at least one of the major properties of albumin or a similar tertiary structure as albumin, such as HSA. Major properties of albumin are summarized in Sleep, 2015, "Albumin and its application in drug delivery", Expert Opinion on Drug Delivery 12(5): 793-812 (incorporated herein by reference).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol*. 48: 443-453) as implemented in the Needle program of the EMBOSS package (EMBOSS: The European Molecular Biology Open Software Suite, Rice et al., 2000, *Trends Genet*. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of
Alignment−Total Number of Gaps in Alignment)

Variant: The term "variant" means a polypeptide derived from a parent polypeptide, e.g. albumin, comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. The altered polypeptide (variant) can be obtained through human intervention by modification of the polynucleotide sequence encoding the parental polypeptide, e.g. albumin. The variant albumin is preferably at least 70%, preferably at least 75%, more preferably at least 80%, more preferably at least 85%, even more preferably at least 90%, most preferably at least 95%, at least 96%, at least 97%, at least 98%, at least 99%, at least 99.5% or at least 99.8% identical to SEQ ID NO: 10 and may or may not maintain at least one of the major properties of the parent albumin or a similar tertiary structure such as HSA. Generally, variants or fragments of HSA will have at least 10% (preferably at least 50%, 60%, 70%, 80%, 90% or 95%) of HSA ligand binding activity (for example bilirubin-binding) and at least 50% (preferably at least 70%, 80%, 90% or 95%) of HSA's oncotic activity, weight for weight. Oncotic activity, also known as colloid osmotic pressure, of albumin, albumin variants or fragments of albumin may be determined by the method described by Hoefs, J. C. (1992) *Hepatology* 16:396-403 (incorporated herein by reference). Bilirubin binding may be measured by fluorescence enhancement at 527 nm relative to HSA. Bilirubin (1.0 mg) is dissolved in 50 microL of 1M NaOH and diluted to 1.0 mL with demineralised water. The bilirubin stock is diluted in 100 mM Tris-HCl pH8.5, 1 mM EDTA to give 0.6 nmol of bilirubin/mL in a fluorometer cuvette. Fluorescence is measured by excitation at 448 nm and emission at 527 nm (10 nm slit widths) during titration with HSA over a range of HSA:bilirubin ratios from 0 to 5 mol:mol. The variant may have altered binding affinity to FcRn and/or an altered plasma half-life when compared to the parent albumin.

With respect to a variant Gsh1 protein, the same principles apply, with the exception that activity is Gsh1 activity rather than albumin activity. The parent Gsh1 protein may have at least 50, 60, 70, 80 or 90% identity to SEQ ID NO: 2, more preferably 100% identity to SEQ ID NO: 2. The variant Gsh1 protein may have at least 50, 60, 70, 80, 85, 90, 95, 96, 97, 98, or at least 99% identity to SEQ ID NO: 2.

With respect to a variant Not4 protein, the same principles apply, with the exception that activity is Not4 activity rather than albumin activity. The parent Not4 protein may have at least 50, 60, 70, 80 or 90% identity to SEQ ID NO: 6, more preferably 100% identity to SEQ ID NO: 6. The variant Not4 protein may have at least 50, 60, 70, 80, 85, 90, 95, 96, 97, 98, or at least 99% identity to SEQ ID NO: 6.

The variant polypeptide sequence is preferably one which is not found in nature.

Vector: The term "vector" means a linear or circular DNA molecule that comprises a polynucleotide encoding a polypeptide and is operably linked to control sequences that provide for its expression. Vectors include plasmids. Vectors include expression vectors.

Wild-type: The term "wild-type" (WT) albumin means an albumin having the same amino acid sequence as the albumins naturally found in an animal or in a human being. SEQ ID NO: 10 is an example of a wild-type albumin from *Homo sapiens*. The "wild-type" human albumin (HSA) sequence is given by GenBank Accession number AAA98797.1 (Minghetti et al. "Molecular structure of the human albumin gene is revealed by nucleotide sequence within q11-22 of chromosome 4", J. Biol. Chem. 261 (15), 6747-6757 (1986), incorporated herein by reference). Examples of wild-type albumins are provided in Table 1 (above).

Conventions for Designation of Amino Acid Positions

For purposes of the present invention, the polypeptide disclosed in SEQ ID NO: 2 is used to determine the corresponding amino acid residue in a homolog of Gsh1 protein. The amino acid sequence of a homolog of Gsh1 protein is aligned with the polypeptide disclosed in SEQ ID NO: 2, and based on the alignment, the amino acid position number corresponding to any amino acid residue in the polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The same principles can be used in relation to Not4, based on SEQ ID NO: 6.

Identification of the corresponding amino acid residue in a homolog of Gsh1 protein can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters. The same principles can be used in relation to Not4, based on SEQ ID NO: 6.

In describing the polypeptides of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411 F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. As disclosed above, an insertion may be to the N-side ('upstream', 'X-1') or C-side ('downstream', 'X+1') of the amino acid occupying a position ('the named (or original) amino acid', 'X').

For an amino acid insertion to the C-side ('downstream', 'X+1') of the original amino acid ('X'), the following nomenclature is used: Original amino acid, position, original amino acid, inserted amino acid. Accordingly, the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
| --- | --- |
| 195 | 195 195a 195b |
| G | G - K - A |

For an amino acid insertion to the N-side ('upstream', 'X-1') of the original amino acid (X), the following nomenclature is used: Original amino acid, position, inserted amino acid, original amino acid. Accordingly, the insertion of lysine (K) before glycine (G) at position 195 is designated "Gly195LysGly" or "G195KG". An insertion of multiple amino acids is designated [Original amino acid, position, inserted amino acid #1, inserted amino acid #2; etc., original amino acid]. For example, the insertion of lysine (K) and alanine (A) before glycine at position 195 is indicated as "Gly195LysAlaGly" or "G195KAG". In such cases the inserted amino acid residue(s) are numbered by the addition of lower case letters with prime to the position number of the amino acid residue following the inserted amino acid residue(s). In the above example, the sequence would thus be:

| Parent: | Variant: |
| --- | --- |
| 195 | 195a' 195b' 195 |
| G | K - A - G |

Multiple alterations. Polypeptides comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

A first aspect of the invention provides a fungal host cell having:
 a. a modified Gsh1 protein or homolog thereof, and/or
 b. a modified level of activity of Gsh1 protein or homolog thereof, and/or
 c. a modified GSH1 gene or homolog thereof, and/or
 d. a modified level of expression of GSH1 gene or homolog thereof.

The modified Gsh1 protein may be modified relative to a reference Gsh1 protein such as a wild-type Gsh1 protein for example SEQ ID NO: 2. Preferably, the modified Gsh1 protein or homolog thereof has at least 50% identity to SEQ ID NO: 2, more preferably at least 55, 60, 65, 70, 75, 80, 85, 90, 95, 96, 97, 98, 99, 99.1, 99.2, 99.3, 99.4, 99.5, 99.6, 99.7, 99.8 or at least 99.9% identity to SEQ ID NO: 2. The modified Gsh1 protein or homolog thereof may or may not have at most 99.9, 99.8, 99.7, 99.6, 99.5, 99.4, 99.3, 99.2, 99.1, 99, 98, 97, 96, 95, 90, 85, 80, 75, 70, 65, or at most 60% identity to SEQ ID NO: 2. More preferably, the modified Gsh1 protein comprises or consists of SEQ ID NO: 4.

It is preferred that the modified level of Gsh1 protein or homolog thereof is a reduced expression level of Gsh1 protein or homolog thereof and/or a reduced activity level of Gsh1 protein or homolog thereof. Preferably the modified, e.g. reduced, level is relative to the level in a reference fungal host cell, such as a fungal host cell in which the Gsh1 protein comprises or consists of SEQ ID NO: 2. The Gsh1 protein of the reference fungal host may be a wild-type Gsh1 sequence, such as SEQ ID NO: 2. A suitable reference fungal host cell is *S. cerevisiae* S288C or *S. cerevisiae* DXY1. S288C has the genotype MATα SUC2 gal2 mal2 mel flo1 flo8-1 hap1 ho bio1 bio6. DXY1 has the genotype leu2-3, leu2-122, can1, pra1, ubc4, ura3:yap3 (Kerry-Williams et al. (1998) Yeast 14:161-169, incorporated herein by reference). Other suitable reference fungal host cells include cells which are identical to the host cell with the exception of the GSH1 gene or Gsh1 protein or homolog thereof. For example, the GSH1 gene of the reference may be wild-type (e.g. SEQ ID NO: 1) or the GSH1 gene of the reference may encode wild-type Gsh1 protein (e.g. SEQ ID NO: 2) or the Gsh1 protein encoded by the reference may be wild-type (e.g. SEQ ID NO: 2). Preferably, the host cell of the invention is identical to a parent strain with the exception of the GSH1 gene or Gsh1 protein or homolog thereof. A reference fungal host may also be referred to as a "corresponding" fungal host. A reference fungal host may be a parent fungal host.

A reduced level of Gsh1 protein and/or activity level of Gsh1 protein may be achieved, for example, by mutating or deleting the GSH1 gene, thus resulting in a mutated Gsh1 protein or homolog thereof or complete absence of Gsh1 protein or homolog thereof; by removing or changing the open reading frame of the gene; by mutating or changing control sequences of the GSH1 gene such as a promoter sequence and/or a terminator sequence; by blocking or reducing transcription of the GSH1 gene for example by introducing suitable interfering RNA such as antisense mRNA; by introducing, controlling or modifying suitable transcriptional activator genes or by introducing an agent which blocks activity level of Gsh1 protein or homolog thereof. Methods of measuring protein levels and protein activity are well known in the art.

The modified activity level of the Gsh1 protein or homolog thereof may be reduced, therefore resulting in from 0, 10, 20, 30, 40, 50, 60, 70, 80, 90, 95, 96, 97, or 98 to 10, 20, 30, 40, 50, 60, 70, 80, 90, 95, 96, 97, 98 or 99% of the activity level of Gsh1 protein or homolog thereof of a parent or reference fungal host cell, such as a wild-type fungal host cell. The modified, e.g. reduced, activity level of Gsh1 protein or homolog thereof in a fungal host cell may be relative to the activity level of Gsh1 protein or homolog thereof of a reference fungal host cell such as a parent fungal host cell or a wild-type fungal host cell as described above. Consequently, the activity level of Gsh1 protein or homolog thereof in the host cell may be at most 99% of the activity level of Gsh1 protein or homolog thereof in a reference fungal host cell, for example at most 98, 97, 96, 95, 90, 80, 70, 60, 50, 40, 30, 20, or at most 10% of the activity level of Gsh1 protein or homolog thereof in the reference fungal host cell. The activity level of Gsh1 protein or homolog thereof may be reduced to zero or substantially zero.

The modified expression level (amount) of Gsh1 protein or homolog thereof may be reduced, therefore resulting in from 0, 10, 20, 30, 40, 50, 60, 70, 80, 90, 95, 96, 97, 98 to 10, 20, 30, 40, 50, 60, 70, 80, 90, 95, 96, 97, 98, 99% of the expression level of Gsh1 protein or homolog thereof of the reference fungal host cell, such as a wild-type fungal host cell. The modified, e.g. reduced, expression level of Gsh1 protein or homolog thereof in a fungal host cell may be relative to the expression level of Gsh1 protein or homolog thereof of a reference fungal host cell such as a parent fungal host cell or a wild-type fungal host cell as described above. Consequently, the expression level of Gsh1 protein or homolog thereof in the host cell may be at most 99% of the expression level of Gsh1 protein or homolog thereof in a reference fungal host cell, for example at most 98, 97, 96, 95, 90, 80, 70, 60, 50, 40, 30, 20, or at most 10% of the expression level of Gsh1 protein or homolog thereof in the reference fungal host cell. The expression level of Gsh1 protein or homolog thereof may be reduced to zero or substantially zero.

The fungal host cell may lack a functional GSH1 gene or homolog thereof or Gsh1 protein or homolog thereof. For example, the fungal host cell may contain a modified GSH1 gene which may result in a reduced expression level of Gsh1 protein or homolog thereof, or in reduced activity level of Gsh1 protein or homolog thereof. The fungal host cell may lack a GSH1 gene or homolog thereof, for example due to deletion, and/or may lack Gsh1 protein or homolog thereof.

GSH1 activity may be measured by using an assay such as that disclosed by Volohonsky et al Chemico-Biological Interactions 140 (2002) 49-65 (incorporated herein by reference), particularly section 2.8.1. Gsh1 expression level may be measured for example by ELISA to determine the amount of protein or by quantitative RT-PCR to measure the RNA level.

The fungal host cell may have a modified Gsh1 protein or homolog thereof comprising a mutation at a position corresponding to a position selected from 47, 48, 49, 50, 51, 120, 121, 122, 123, 124, 125, 126, 127, 128, 129, 130, 409, 451, 452, 453, 454 and 455 of SEQ ID NO: 2, preferably a position selected from:

a position corresponding to any of positions 47, 48, 49, 50 and 51 of SEQ ID NO: 2, preferably corresponding to position 49;

a position corresponding to any of positions 120, 121, 122, 123, 124, 125, 126, 127, 128, 129 or 130 of SEQ ID NO: 2, preferably corresponding to position 123, 124, 125, 126 or 127, more preferably corresponding to position 125; or a position corresponding to position 409 of SEQ ID NO: 2;

a position corresponding to any of positions 451, 452, 453, 454 or 455 of SEQ ID NO: 2, preferably corresponding to position 453.

Most preferably, the fungal host cell has a modified Gsh1 protein or homolog thereof comprising a mutation at a position corresponding to position 125 of SEQ ID NO: 2.

The mutation may be a substitution, insertion and/or deletion at one or more (e.g. several) positions. Substitutions are preferred.

The fungal host cell may comprise a polynucleotide sequence encoding the modified Gsh1 protein or homolog thereof, for example SEQ ID NO: 3. Due to the degeneracy of the genetic code, other polynucleotide sequences can also encode suitable modified Gsh1 proteins or homologs thereof.

Amino acids fall into various well-known classes. Therefore, some amino acids are more closely related than others. As used herein, "conservative amino acid substitutions" refers to substitutions made within the same group, and which typically do not substantially affect protein function. By "conservative substitution" is intended within groups such as those shown by FIG. 1, this is a Venn diagram which provides one system by which conservation level can be visualized. Generally, substitutions of low conservation are those for which there are many boundaries (lines) between the starting amino acid and the resultant substitution. "Conservative amino acid substitution" includes a substitution made within the same group such as within:

aromatic amino acids: F, H, W, Y;
aliphatic amino acids: I, L, V;
hydrophobic amino acids: A, C, F, H, I, K, L, M, T, V, W, Y;
charged amino acids: D, E, H, K, R, for example:
positively charged amino acids: H, K, R; or
negatively charged amino acids: D, E;
polar amino acids: C, D, E, H, K, N, Q, R, S, T, W, Y;
small amino acids: A, C, D, G, N, P, S, T, V, for example:
tiny amino acids: A, C, G, S.

Alternatively, "conservative substitution" may be within the following groups:

amino acids having aliphatic side chains: G, A, V, L, I;
amino acids having aromatic side chains: F, Y, W;
amino acids having sulphur-containing side chains: C, M;
amino acids having aliphatic hydroxyl side chains: S, T;
amino acids having basic side chains: K, R, H;
acidic amino acids and their amide derivatives: D, E, N, Q.

Substitutions may be made by techniques known in the art, such as by site-directed mutagenesis as disclosed in U.S. Pat. No. 4,302,386 (incorporated herein by reference).

Non-conservative amino substitutions may refer to substitutions made from one group to another group for example from the group having aromatic side chains to the group having aliphatic side chains.

The fungal host cell may comprise a modified Gsh1 protein or homolog thereof in which, relative to SEQ ID NO: 2, the mutation is a substitution to an amino acid, preferably a non-conserved amino acid, selected from A, C, D, E, F, G, H, I, K, L, M, N, P, Q, R, S, T, V, W and Y.

The mutation at a position corresponding to position 125 of SEQ ID NO: 2 may be a substitution from the native amino acid, such as R, to a non-native amino acid such as to A, C, D, E, F, G, H, I, L, M, N, P, Q, S, T, V, W or Y, preferably to C, D, E or G, more preferably to G. The substitution may be from a positively charged amino acid to an aliphatic, aromatic, hydrophobic, small, tiny, polar or negatively charged amino acid, preferably a negatively charged amino acid to a tiny amino acid. A particularly preferred substitution is from R to G. Substitution to K is less preferred.

The mutation at a position corresponding to position 49 of SEQ ID NO: 2 may be a substitution from the native amino acid, such as D, to a non-native amino acid such as A, C, F, G, H, I, K, L, M, N, P, Q, R, S, T, V, W or Y, preferably to H, K or R, more preferably to K or R. The substitution may be from a negatively charged amino acid to a positively charged amino acid. Substitution to E is less preferred.

The mutation at a position corresponding to position 409 of SEQ ID NO: 2 may be a substitution from the native amino acid, such as H, to a non-native amino acid such as A, C, D, E, F, G, I, K, L, M, N, P, Q, R, S, T, V, W or Y, preferably to A, I, L, V, M, F, W, Y, more preferably to A, I, L, V, most preferably to L. The substitution may be from an aromatic amino acid to an aliphatic amino acid. A particularly preferred substitution is from H to L.

The mutation at a position corresponding to position P453 of SEQ ID NO: 2 may be a substitution from the native amino acid, such as P, to a non-native amino acid such as A, C, D, E, F, G, H, I, K, L, M, N, Q, R, S, T, V, W or Y, preferably to A, I, L, V, M, F, W Y, more preferably to A, I, L, V, most preferably to L. The substitution may be from an aromatic amino acid to an aliphatic amino acid. A particularly preferred substitution is from P to L.

A preferred modified Gsh1 protein includes a mutation at a position corresponding to R125 of SEQ ID NO: 2.

A preferred modified Gsh1 protein comprises or consists of SEQ ID NO: 4, i.e. which includes the mutation R125G. Such a modified Gsh1 protein may be provided using a nucleotide sequence encoding a Gsh1 protein (e.g. SEQ ID NO: 1), the nucleotide sequence including the single nucleotide polymorphism (SNP) A373G may be provided using, for example SEQ ID NO: 3.

Alternatively, the modified level may be an increased level. An increased level or increased activity level of Gsh1 protein or homolog thereof is likely to decrease the yield of desired protein (such as a heterologous protein). Such a decreased yield may be desirable when, for example, the desired protein is detrimental to the viability of the host cell. An increased level may be at least 101, 102, 103, 104, 105, 110, 120, 130, 140, 150, 175, or 200% of the level in a reference host such as a parent host.

Position R125 is proposed to be involved in a salt bridge interaction with position D49. Mutation of either amino acid could be used to disrupt this interaction. Mutating R125 to D or E, or D49 to R or K could result in electrostatic repulsion effects which would be expected to destabilise the interaction between positions 125 and 49. However, mutation of R125 to K and/or D49 to E (glutamate) may maintain the interaction.

The Gsh1 protein may be exogenous to the host cell or may be endogenous to the host cell. When the Gsh1 protein is exogenous to the host cell, the host cell may maintain or lack a Gsh1 protein that is endogenous to the host cell.

The fungal host according to the first aspect of the invention may in addition have:
- a modified Not4 protein or homolog thereof, and/or
- a modified level of activity of Not4 protein or homolog thereof, and/or
- a modified NOT4 gene or homolog thereof, and/or
- a modified level of expression of NOT4 gene or homolog thereof.

NOT4 is also known as MOT2. The modified Not4 protein may be modified relative to a reference Not4 protein such as a wild-type Not4 protein, for example SEQ ID NO: 6. Preferably, the modified Not4 protein or homolog thereof has at least 70% identity to SEQ ID NO: 6, more preferably at least 75, 80, 85, 90, 95, 96, 97, 98, 99, 99.1, 99.2, 99.3, 99.4, 99.5, 99.6, 99.7, 99.8 or at least 99.9% identity to SEQ ID NO: 6. The modified Not4 protein or homolog thereof may or may not have at most 99.9, 99.8, 99.7, 99.6, 99.5, 99.4, 99.3, 99.2, 99.1, 99, 98, 97, 96, 95, 90, 85, 80, 75, 70, 65, or at most 60% identity to SEQ ID NO: 6. More preferably, the modified Not4 protein comprises or consists of SEQ ID NO: 8.

It is preferred that the modified level of Not4 protein or homolog thereof is a reduced expression level of Not4 protein or homolog thereof or a reduced activity level of Not4 protein or homolog thereof. Preferably the modified, e.g. reduced, level is relative to the level in a reference fungal host cell, such as a fungal host cell in which the Not4 protein comprises or consists of SEQ ID NO: 6. The Not4 protein of the reference fungal host may be a wild-type Not4 sequence, such as SEQ ID NO: 6. A suitable reference fungal host cell is S. cerevisiae S288C or S. cerevisiae DXY1, as described above. Other suitable reference fungal host cells include cells which are identical to the host cell with the exception of the NOT4 gene or Not4 protein or homolog thereof. For example, the NOT4 gene of the reference may be wild-type (e.g. SEQ ID NO: 5) or the NOT4 gene of the reference may encode wild-type Not4 protein (e.g. SEQ ID NO: 6) or the Not4 protein encoded by the reference may be wild-type (e.g. SEQ ID NO: 6). Preferably, the host cell of the invention is identical to a parent strain with the exception of the NOT4 gene or Not4 protein or homolog thereof. A reference fungal host may also be referred to as a "corresponding" fungal host. A reference fungal host may be a parent fungal host.

A reduced level of Not4 protein or activity level of Not4 protein may be achieved, for example, by mutating or deleting the NOT4 gene, thus resulting in a mutated Not4 protein or homolog thereof or complete absence of Not4 protein or homolog thereof; by removing or changing the open reading frame of the gene, by mutating or changing control sequences of the NOT4 gene such as a promoter sequence and/or a terminator sequence; by blocking or reducing transcription of the NOT4 gene for example by introducing suitable interfering RNA such as antisense mRNA, by introducing, controlling or modifying suitable transcriptional activator genes or by introducing an agent which blocks activity level of Not4 protein or homolog thereof. Methods of measuring protein levels are well known in the art.

The modified activity level of the Not4 protein or homolog thereof may be reduced, therefore resulting in from 0, 10, 20, 30, 40, 50, 60, 70, 80 or 90 to 10, 20, 30, 40, 50, 60, 70, 80, 90, 95, 96, 97, or 98% of the activity level of Not4 protein or homolog thereof of a parent or reference fungal host cell, such as a wild-type fungal host cell. The modified, e.g. reduced, activity level of Not4 protein or homolog thereof in a fungal host cell may be relative to the activity level of Not4 protein or homolog thereof of a reference fungal host cell such as a parent fungal host cell or a wild-type fungal host cell as described above. Consequently, the activity level of Not4 protein or homolog thereof in the host cell may be at most 99% of the activity level of Not4 protein or homolog thereof in a reference fungal host cell, for example at most 98, 97, 96, 95, 90, 80, 70, 60, 50, 40, 30, 20, or at most 10% of the activity level of Not4 protein or homolog thereof in the reference fungal host cell. The activity level of Not4 protein or homolog thereof may be reduced to zero or substantially zero.

The modified expression level (amount) of Not4 protein or homolog thereof may be reduced, therefore resulting in from 0, 10, 20, 30, 40, 50, 60, 70, 80 or 90 to 10, 20, 30, 40, 50, 60, 70, 80, 90, 95, 96, 97, or 98% of the expression level of Not4 protein or homolog thereof of the reference fungal host cell, such as a wild-type fungal host cell. The modified, e.g. reduced, expression level of Not4 protein or homolog thereof in a fungal host cell may be relative to the expression level of Not4 protein or homolog thereof of a reference fungal host cell such as a parent fungal host cell or a wild-type fungal host cell as described above. Consequently, the expression level of Not4 protein or homolog thereof in the host cell may be at most 99% of the expression level of Not4 protein or homolog thereof in a reference fungal host cell, for example at most 98, 97, 96, 95, 90, 80, 70, 60, 50, 40, 30, 20, or at most 10% of the expression level of Not4 protein or homolog thereof in the reference fungal host cell. The expression level of Not4 protein or homolog thereof may be reduced to zero or substantially zero.

The fungal host cell may lack a functional NOT4 gene or homolog thereof or Not4 protein or homolog thereof. For example, the fungal host cell may contain a modified NOT4 gene which may result in a reduced expression level of Not4 protein or homolog thereof, or in reduced activity level of Not4 protein or homolog thereof. The fungal host cell may lack a NOT4 gene or homolog thereof, for example due to deletion, and/or may lack Not4 protein or homolog thereof.

Not4 expression level may be measured for example by ELISA to determine the amount of protein or by quantitative RT-PCR to measure the RNA level.

The modified Not4 protein, or homolog thereof, may be mutated so that its interaction with Nott protein, or homolog thereof, is altered. For example, the N-terminal region of Not4 protein, or homolog thereof, may be mutated, such as the α-helix containing amino acids corresponding to positions 426 to 439 of SEQ ID NO: 6.

Therefore, the invention also provides a fungal host cell further having a Not4 protein or homolog thereof which has a weaker interaction, such as hydrophobic interaction, with Nott than the interaction between a wild-type Not4 protein (e.g. SEQ ID NO: 6) and a wild-type Nott protein (e.g. SEQ ID NO: 13).

The fungal host cell may have a modified Not4 protein or homolog thereof comprising a mutation at a position corresponding to a position selected from 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469 or 470 of SEQ ID NO: 6, preferably a position selected from:

a position corresponding to 426, 427, 428, 429, 430, 431, 432, 433, 434, 435, 436, 437, 438, or 439 of SEQ ID NO: 6, preferably position 429, 430, 434, or 437, most preferably position 429;

a position corresponding to 460, 461, 462, 463, 464, 465, 466, 467, 468, 469 or 470 of SEQ ID NO: 6, preferably position 463, 464, or 466; or a position corresponding to 438, 439, 440, 441, 442, 443, 444, 445, 446, 447, 448, 449, 450, 451, 452, 453, 454, 455, or 456 of SEQ ID NO: 6, preferably position 442, 445, 447 or 452.

The mutation may be a substitution, insertion and/or deletion at one or more (e.g. several) positions. Substitutions are preferred.

The fungal host cell may comprise a polynucleotide sequence encoding the modified Not4 protein or homolog thereof, for example SEQ ID NO: 7. Due to the degeneracy of the genetic code, other polynucleotide sequences can also encode suitable modified Not4 proteins or homologs thereof.

The fungal host cell may comprise a modified Not4 protein or homolog thereof in which, relative to SEQ ID NO: 6, the mutation is a substitution to an amino acid, preferably a non-conserved amino acid, selected from A, C, D, E, F, G, H, I, K, L, M, N, P, Q, R, S, T, V, W and Y.

The mutation at a position corresponding to position 429 of SEQ ID NO: 6 may be a substitution from the native amino acid, such as F, to a non-native amino acid such as A, C, D, E, F, G, H, I, K, L, M, N, P, Q, R, S, T, V, W, or Y, preferably to G, A, V, L, or I, more preferably to V, L or I, most preferably to I. The substitution may be to a non-conserved amino acid. The substitution may be to an aliphatic amino acid. A particularly preferred substitution is from F to I.

The mutation at a position corresponding to position 430 of SEQ ID NO: 6 may be a substitution from the native amino acid, such as L, to any non-native amino acid such as A, C, D, E, F, G, H, I, K, L, M, N, P, Q, R, S, T, V, W, or Y. The substitution may be to a non-conserved amino acid.

The mutation at a position corresponding to position 434 may be a substitution from the native amino acid, such as L, to any non-native amino acid such as A, C, D, E, F, G, H, I, K, L, M, N, P, Q, R, S, T, V, W, or Y. The substitution may be to a non-conserved amino acid.

The mutation at a position corresponding to position 437 of SEQ ID NO: 6 may be a substitution from the native amino acid, such as L, to any non-native amino acid such as A, C, D, E, F, G, H, I, K, L, M, N, P, Q, R, S, T, V, W, or Y. The substitution may be to a non-conserved amino acid.

A preferred modified Not4 protein includes a mutation at a position corresponding to F429 of SEQ ID NO: 6.

A preferred modified Not4 protein comprises or consists of SEQ ID NO: 8, i.e. which includes the mutation F429I. Such a modified Not4 protein may be provided using a nucleotide sequence encoding a Not4 protein (e.g. SEQ ID NO: 5), the nucleotide sequence including the SNP T1285A, for example SEQ ID NO: 7.

Alternatively, the modified level may be increased. An increased level or increased activity of Not4 protein or homolog thereof is likely to decrease the yield of desired protein (such as a heterologous protein). Such a decreased yield may be desirable when, for example, the desired protein is detrimental to the viability of the host cell. An increased level may be at least 101, 102, 103, 104, 105, 110, 120, 130, 140, 150, 175, or 200% of the level in a reference host such as a parent host.

The Not4 protein may be exogenous to the host cell or may be endogenous to the host cell. When the Not4 protein is exogenous to the host cell, the host cell may maintain or lack a Not4 protein that is endogenous to the host cell.

The fungal host may have both (1) a modified level of Gsh1 protein or homolog thereof and/or a modified level of activity of Gsh1 protein or homolog thereof, and/or a modified GSH1 gene or homolog thereof, and/or a modified level of expression of GSH1 gene or homolog thereof and (2) a modified level of Not4 protein or homolog thereof and/a modified level of activity of Not4 protein or homolog thereof, and/or a modified NOT4 gene or homolog thereof, and/or a modified level of expression of NOT4 gene or homolog thereof. Preferably, the fungal host has (1) a reduced level of Gsh1 protein or homolog thereof or reduced level of activity of Gsh1 protein or homolog thereof and/or a reduced level of expression of GSH1 gene or homolog thereof and (2) a reduced level of Not4 protein or homolog thereof or reduced level of activity of Not4 protein or homolog thereof and/or a reduced level of expression of NOT4 gene or homolog thereof. Alternatively, the fungal host may have (1) a reduced level of Gsh1 protein or homolog thereof or reduced level of activity of Gsh1 protein or homolog thereof and/or a reduced level of expression of GSH1 gene or homolog thereof and (2) an increased level of Not4 protein or homolog thereof or increased level of activity of Not4 protein or homolog thereof and/or an increased level of expression of NOT4 gene or homolog thereof. Alternatively, the fungal host may have (1) an increased level of Gsh1 protein or homolog thereof or increased level of activity of Gsh1 protein or homolog thereof and/or an increased level of expression of GSH1 gene or homolog thereof and (2) a reduced level of Not4 protein or homolog thereof or reduced level of activity of Not4 protein or homolog thereof and/or a reduced level of expression of NOT4 gene or homolog thereof. The same options apply with respect to expression levels of GSH1 and NOT4. 'Increased' and 'reduced' are as described herein.

Preferably the modified, e.g. reduced, level of Gsh1 is relative to the level in a reference fungal host cell, such as a fungal host cell in which the Gsh1 protein comprises or consists of SEQ ID NO: 2 and the modified e.g. reduced, level of Not4 is relative to the level in a reference fungal host cell, such as a fungal host cell in which the Not4 protein comprises or consists of SEQ ID NO: 6. The Gsh1 protein of the reference fungal host may be a wild-type Gsh1 sequence, such as SEQ ID NO: 2. The Not4 protein of the reference fungal host may be a wild-type Not4 sequence, such as SEQ ID NO: 6. A suitable reference fungal host cell is *S. cerevisiae* S288C or *S. cerevisiae* DXY1 as described above. Other suitable reference fungal host cells include cells which are identical to the host cell with the exception of the GSH1 gene or Gsh1 protein or homolog thereof and the NOT4 gene or Not4 protein or homolog thereof. For example, the GSH1 gene of the reference may be wild-type (e.g. SEQ ID NO: 1) or the GSH1 gene of the reference may encode wild-type Gsh1 protein (e.g. SEQ ID NO: 2) or the Gsh1 protein encoded by the reference may be wild-type (e.g. SEQ ID NO: 2). The NOT4 gene of the reference may be wild-type (e.g. SEQ ID NO: 5) or the NOT4 gene of the reference may encode wild-type Not4 protein (e.g. SEQ ID NO: 6) or the Not4 protein encoded by the reference may be wild-type (e.g. SEQ ID NO: 6). Preferably, the host cell of the invention is identical to a parent strain with the exception of the GSH1 gene or Gsh1 protein or homolog thereof and the NOT4 gene or Not4 protein or homolog thereof. A reference fungal host may also be referred to as a "corresponding" fungal host. A reference fungal host may be a parent fungal host.

The fungal host cell may be a recombinant fungal host cell.

The fungal host cell may be a yeast or a filamentous fungus. "Fungi" as used herein includes the phyla Ascomycota, Basidiomycota, Chytridiomycota, and Zygomycota (as defined by Hawksworth et al., in, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No: 9, 1980, pages 1 to 27).

In a more preferred aspect, the yeast host cell is a *Candida, Hansenula, Kluyveromyces, Pichia, Saccharomyces, Schizosaccharomyces,* or *Yarrowia* cell.

In a more preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis* or a *Yarrowia lipolytica* cell. A *Saccharomyces cerevisiae* host is particularly preferred.

The *S. cerevisiae* host may or may not comprise one or more of the following genotypic features: leu2-3, leu2-122, can1, pra1, ubc4, ura3, yap3::URA3, lys2, hsp150::LYS2, pmt1::URA3 (as defined in WO2014/138371, incorporated herein by reference), for example *S. cerevisiae* BXP10. Preferably the *S. cerevisiae* host includes MATa.

The *S. cerevisiae* host may or may not comprise one or more of the following genotype, MATa, leu2-3, leu2-112, ubc4, ura3, yap3::URA3, lys2, hsp150::LYS2; with PDI1, URA3 and Ylplac211 integrated at the PDI1 locus (Finnis et al 2010, Microbial Cell Factories 9:87), for example *S. cerevisiae* DP9.

The *S. cerevisiae* host may or may not comprise one or more of the following genotype, MATα, leu2, pep4-3, for example *S. cerevisiae* MT302/28B as described in Finnis et al 1993, Eur. J. Biochem, 212: 201-210.

The *S. cerevisiae* host may or may not comprise the following genotype: MATα, SUC2, gal2, mal2, mel, flo1, flo8-1, hap1, ho, bio1, bio6 (Mortimer and Johnston (1986) Genetics 113:35-43), for example *S. cerevisiae* S288C.

A preferred *S. cerevisiae* host strain comprises or consists of all of MATa, leu2-3, leu2-122, can1, pra1, ubc4, ura3, yap3::URA3, lys2, hsp150::LYS2, and pmt1::URA3.

Another preferred *S. cerevisiae* host comprises or consists of all of: MATa, leu2-3, leu2-112, ubc4, ura3, yap3::URA3, lys2, hsp150::LYS2, with PDI1, URA3 and Ylplac211 integrated at the PDI1 locus.

Another preferred *S. cerevisiae* host comprises or consists of all of: MATa, SUC2, gal2, mal2, mel, flo1, flo8-1, hap1, ho, bio1, bio6.

Another preferred *S. cerevisiae* host comprises or consists of all of: MATα, leu2, pep4-3.

The host may be polyploid, diploid or halpoid. A haploid or diploid yeast host is preferred, preferably haploid.

The host mating type may be, for example, MATa or MATα (Mat-alpha). Preferably the *S. cerevisiae* host contains a plasmid encoding human albumin or variant, fragment and/or fusion thereof.

"Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Preferred filamentous fungal host cells may or may not include *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* or *Trichoderma.*

The fungal host cell, may comprise a nucleotide sequence encoding a desired protein. Preferably, the desired protein is a heterologous protein. A heterologous protein is one not naturally produced by the host cell and, preferably, does not include proteins such as selectable markers, for example antibiotic resistance markers or auxotrophic markers, chaperones, FLP or FRT.

The fungal host cell may be an expression host. The fungal host cell may comprise an expression cassette for example encoding a desired protein such as a heterologous protein. The expression cassette may be, for example within a vector such as a plasmid. The fungal host cell may comprise an expression vector.

The desired protein may or may not be a plant or animal protein or variant thereof. The desired protein may, or may not, comprise the sequence of albumin, a monoclonal antibody, an etoposide, a serum protein (such as a blood clotting factor), antistasin, a tick anticoagulant peptide, transferrin, lactoferrin, endostatin, angiostatin, collagens, immunoglobulins or immunoglobulin-based molecules or fragment of either (e.g. a Small Modular ImmunoPharmaceutical™ ("SMIP") or dAb, Fab' fragments, F(ab')2, scAb, scFv or scFv fragment), a Kunitz domain protein (such as those described in WO03/066824 (incorporated herein by reference), with or without albumin fusions), interferons, interleukins, IL-10, IL-11, IL-2, interferon α (alpha) species and sub-species, interferon β (beta) species and sub-species, interferon γ (gamma) species and sub-species, leptin, CNTF, $CNTF_{Ax15}$, IL-1-receptor antagonist, erythropoietin (EPO) and EPO mimics, thrombopoietin (TPO) and TPO mimics, prosaptide, cyanovirin-N, 5-helix, T20 peptide, T1249 peptide, HIV gp41, HIV gp120, urokinase, prourokinase, tPA, hirudin, platelet derived growth factor, parathyroid hormone, proinsulin, insulin, glucagon, glucagon-like peptides such as exendin-4, GLP-1 or GLP-2, insulin-like growth factor, calcitonin, growth hormone, transforming growth factor β (beta), tumour necrosis factor, G-CSF, GM-CSF, M-CSF, FGF, coagulation factors in both pre and active forms, including but not limited to plasminogen, fibrinogen, thrombin, pre-thrombin, pro-thrombin, von Willebrand's factor, $alpha_1$-antitrypsin, plasminogen activators, Factor VII, Factor VIII, Factor IX, Factor X and Factor XIII, nerve growth factor, LACI, platelet-derived endothelial cell growth factor (PD-ECGF), glucose oxidase, serum cholinesterase, aprotinin, amyloid precursor protein, inter-alpha trypsin inhibitor, antithrombin III, apo-lipoprotein species, Protein C, Protein S, a metabolite, an antibiotic, or a variant or fragment of any of the above.

Preferably the variant has at least 70, 75, 80, 85, 90, 91, 92, 93, 94, 95, 96, 97, 98, or 99% identity to one or more of the proteins disclosed above.

A preferred desired protein may or may not be a serum protein such as an albumin or variant, fragment and/or fusion thereof. Preferably, the albumin has from 60, 65, 70, 75, 80, 85, 90, 95, 96, 97, 98, 98.2, 98.4, 98.6, 98.8, 99, 99.2, 99.3, 99.4, 99.5, 99.6, 99.7, 99.8, or 99.9 to 70, 75, 80, 85, 90, 95, 96, 97, 98, 98.2, 98.4, 98.6, 98.8, 99, 99.2, 99.3, 99.4, 99.5, 99.6, 99.7, 99.8, 99.9, or 100% sequence identity to SEQ ID NO: 10. Most preferably, the albumin comprises or consists of SEQ ID NO: 10.

The albumin variant, fragment and/or fusion thereof may or may not comprise from 1, 2, 3, 4, 5, 6, 7, 8, 9, 10, 11, 12, 13, 14, 15, 16, 17, 18, or 19 to 2, 3, 4, 5, 6, 7, 8, 9, 10, 11, 12, 13, 14, 15, 16, 17, 18, 19 or 20 mutations relative to SEQ ID NO: 10. Preferred albumin variants comprises from 1 to 10 mutations relative to SEQ ID NO: 10, more preferably from 1 to 5 mutations. Preferred mutations include substitutions.

The albumin variant, fragment and/or fusion thereof may or may not comprise A, C, D, E, F, G, H, I, L, M, N, P, Q, R, S, T, V, W or Y at a position corresponding to position K573 of SEQ ID NO: 10, more preferably a P, H, W or Y at a position corresponding to position K573 of SEQ ID NO: 10. Particularly preferred albumin variants have at least 95% identity to SEQ ID NO: 10 (more preferably at least 96, 97, 98 or 99% identity) and comprise P at a position corresponding to 573 of SEQ ID NO: 10.

The albumin variant, fragment and/or fusion thereof may or may not comprise A, C, D, F, G, H, I, K, L, M, N, P, Q, R, S, T, V, W or Y at a position corresponding to position E492 of SEQ ID NO: 10, more preferably a G, D, F, H, M or R at a position corresponding to position E492 of SEQ ID NO: 10, even more preferably a G or D at a position corresponding to position E492 of SEQ ID NO: 10. Particularly preferred albumin variants have at least 95% identity to SEQ ID NO: 10 (more preferably at least 96, 97, 98 or 99% identity) and comprise G at a position corresponding to E492 of SEQ ID NO: 10.

The albumin variant, fragment and/or fusion thereof may or may not comprise A, C, D, E, F, G, H, I, L, M, N, P, Q, R, S, T, V, W or Y at a position corresponding to position K574 of SEQ ID NO: 10, more preferably a H, G, D, F, N, S or Y at a position corresponding to position K574 of SEQ ID NO: 10, even more preferably a D, F, G or H at a position corresponding to position K574 of SEQ ID NO: 10. Particularly preferred albumin variants have at least 95% identity to SEQ ID NO: 10 (more preferably at least 96, 97, 98 or 99% identity) and comprise H at a position corresponding to K574 of SEQ ID NO: 10.

The albumin variant, fragment and/or fusion thereof may or may not comprise A, C, D, E, F, G, H, I, K, L, M, N, P, R, S, T, V, W or Y at a position corresponding to position Q580 of SEQ ID NO: 10, more preferably a K or R at a position corresponding to position Q580 of SEQ ID NO: 10. Particularly preferred albumin variants have at least 95% identity to SEQ ID NO: 10 (more preferably at least 96, 97, 98 or 99% identity) and comprise K at a position corresponding to Q580 of SEQ ID NO: 10.

Preferred albumin variants may or may not comprise mutations at one or more positions selected to those corresponding to positions 492, 573, 574 and 580, for example the substitutions described above. For example, the albumin variant may comprise or consist of SEQ ID NO: 45.

Other preferred albumin variants, fragments and/or fusions thereof include those disclosed in WO2011/051489, WO2011/124718, WO2012/059486, WO2012/150319, WO2014/072481, WO2013/135896, WO2015/036579, WO2010/092135, WO2013/075066, WO2014/179657, WO2009/126920, WO2010/059315, WO2011/103076, WO2012/112188, WO2015/063611 and WO 2017/029407 or fragments of fusions thereof (each incorporated herein by reference).

The albumin may or may not be a fragment of an albumin or variant thereof.

The albumin variant, fragment and/or fusion thereof may have a binding affinity to FcRn that is stronger or weaker (and, preferably, is stronger) than that of the parent albumin, fragment and/or fusion thereof.

The albumin variant, fragment and/or fusion thereof may have a KD to FcRn (e.g. shFcRn) that is lower than the corresponding KD for HSA or conjugate thereof to. Preferably, the KD for the albumin variant, fragment and/or fusion thereof is less than 0.9×KD for HSA to FcRn, more preferred less than 0.5×KD for HSA to FcRn, more preferred less than 0.1×KD for HSA to FcRn, even more preferred less than 0.05×KD for HSA to FcRn, even more preferred less than 0.02×KD for HSA to FcRn, even more preferred less than 0.01×KD for HSA to FcRn and most preferred less than 0.001×KD for HSA to FcRn (where × means 'multiplied by'). A lower KD corresponds to a stronger binding affinity.

The albumin variant, fragment and/or fusion thereof may have a KD to FcRn that is higher than the corresponding KD for HSA or conjugate thereof to FcRn. Preferably, the KD for the albumin variant, fragment and/or fusion thereof is more than 2×KD for HSA to FcRn, more preferred more than 5×KD for HSA to FcRn, more preferred more than 10×KD for HSA to FcRn, even more preferred more than 25×KD for HSA to FcRn, most preferred more than 50×KD for HSA to FcRn. The albumin variant, fragment and/or fusion thereof may be a null binder to FcRn. A higher KD corresponds to a weaker binding affinity.

When determining and/or comparing KD, one or more (e.g. several) (and preferably all) of the following parameters may be used:

Instrument: Biacore 3000 instrument (GE Healthcare)

Flow cell: CM5 sensor chip

FcRn: human FcRn, preferably soluble human FcRn, optionally coupled to a tag such as Glutathione S Transferase (GST) or Histidine (His), most preferably His such as 6 histidine residues at the C-terminus of the beta-2-microglobulin.

Quantity of FcRn: 1200-2500 RU

Coupling chemistry: amine coupling chemistry (e.g. as described in the protocol provided by the manufacturer of the instrument).

Coupling method: The coupling may be performed by injecting 20 μg/ml of the protein in 10 mM sodium acetate pH 5.0 (GE Healthcare). Phosphate buffer (67 mM phosphate buffer, 0.15 M NaCl, 0.005% Tween 20) at pH 5.5 may be used as running buffer and dilution buffer. Regeneration of the surfaces may be done using injections of HBS-EP buffer (0.01 M HEPES, 0.15 M NaCl, 3 mM EDTA, 0.005% surfactant P20) at pH 7.4 (Biacore AB).

Quantity of injection of test molecule (e.g. HSA or variant) 20-0.032 μM.

Flow rate of injection: constant, e.g. 30 μl/ml.

Temperature of injection: 25° C.

Data evaluation software: BIAevaluation 4.1 software (BIAcore AB).

The albumin variant, fragment and/or fusion thereof may have a plasma half-life that is longer or shorter, preferably longer, than that of the parent albumin, fragment and/or fusion thereof.

Plasma half-life is ideally determined in vivo in suitable individuals. However, since it is time consuming and expensive and inevitably there are ethical concerns connected with doing experiments in animals or man, it is desirable to use an in vitro assay for determining whether plasma half-life is extended or reduced. It is known that the binding of albumin to its receptor (FcRn) is important for plasma half-life and the correlation between receptor binding and plasma half-life is that a higher affinity of albumin to its receptor leads to longer plasma half-life. Thus, for the invention, a higher affinity of albumin to FcRn is considered indicative of an increased plasma half-life and a lower affinity of albumin to its receptor is considered indicative of a reduced plasma half-life.

The binding of albumin to its receptor FcRn may be described using the term affinity and the expressions "stronger" or "weaker". Thus, it should be understood that, a molecule having a higher affinity to FcRn than the affinity of HSA to FcRn is considered to bind more strongly to FcRn than HSA binds to FcRn and a molecule having a lower affinity to FcRn than the affinity of HSA to FcRn is considered to bind more weakly to FcRn than HSA binds to FcRn. The term 'binding coefficient' can be used instead of the term 'binding affinity'.

The terms "longer plasma half-life" or "shorter plasma half-life" and similar expressions are understood to be in relationship to the corresponding parent or reference or corresponding albumin molecule. Thus, a longer plasma half-life with respect to a variant albumin of the invention means that the variant has longer plasma half-life than that of the corresponding albumin having the same sequences except for the alteration(s) described herein.

The albumin or variant, and/or fragment thereof may or may not be genetically fused to a fusion partner. Preferably, the fusion partner is a non-albumin protein. The fusion partner may be fused at the N' or C' terminus of the albumin. There may or may not be one or more spacer amino acids located between the albumin moiety and the partner moiety. Fusion partners may be inserted within the albumin sequence. The fusion partner may be at least 5 amino acids long, for example at least 5, 10, 15, 20, 25, 30, 35, 40, 50, 60, 70, 80, 90 or at least 100 amino acids long. The fusion partner may or may not have a maximum length of from 35, 30, 40, 50, 60, 70, 80, 90, 100, 125, 150, 175, 200, 300, 400, 500, 600, 700, 800, 900 or 1000 amino acids long. The fusion protein may comprise one or more fusion partners, for example fused at the N' or C' terminus of albumin or inserted within the albumin sequence. The fusion protein may comprise one or more (e.g. several, such as 2, 3, 4 or 5) copies of the same fusion partner or two or more different partners. The fusion partner may be selected from desired or heterologous proteins as disclosed above.

A preferred fusion protein may comprise a polypeptide having GLP-1 activity such as those described in WO2014/138371 (incorporated herein by reference, with particular reference to pages 13, 14, 26, 34 to 37). For example, a preferred fusion protein may comprise HSA (SEQ ID NO: 10), or a variant (for example SEQ ID NO: 45) and/or fragment of HSA genetically fused in series to one copy of a GLP analog (e.g. SEQ ID NO: 14 or 51) or HSA (SEQ ID NO: 10), or a variant (for example SEQ ID NO: 45) and/or fragment of HSA genetically fused in series to a tandem repeat of a GLP analog (e.g. SEQ ID NO: 15, 52 or 53). For example, the fusion protein may comprise or consist of SEQ ID NO: 16 (albiglutide).

Particularly suitable fungal host cells for the production of albumins, variants, fragments and/or fusions thereof include, but are not limited to, *Aspergillus* (WO06/066595), *Kluyveromyces* (Fleer, 1991, Bio/technology 9: 968-975), *Pichia* (Kobayashi, 1998, Therapeutic Apheresis 2: 257-262) and *Saccharomyces* (Sleep, 1990, Bio/technology 8: 42-46)), each incorporated herein by reference.

The desired protein (such as a heterologous protein) may or may not be a secreted protein. Therefore, the protein encoded by the host cell may or may not comprise a signal peptide (which in some literature may also be referred to as a "leader sequence"). Typically, the signal peptide sequence is cleaved from the protein during secretion from the host cell, therefore the resultant (mature) protein does not comprise a signal peptide sequence. Examples of suitable signal peptide sequences are provided below. A signal peptide may or may not comprise a pro-peptide.

Alternatively, the desired protein may or may not be intracellular.

The desired protein may or may not be encoded by a plasmid.

The desired protein may or may not be encoded by chromosomal nucleic acid.

Suitable plasmids include 2-micron family plasmids such as those described in WO2006/067511 (incorporated herein by reference, with particular emphasis on the section titled "The 2 μm-family plasmids:" on pages 46 to 61). Such plasmids, collectively termed "2 μm-family plasmids", include pSR1, pSB3 and pSB4 from *Zygosaccharomyces rouxii* (formerly classified as *Zygosaccharomyces bisporus*), plasmids pSB1 and pSB2 from *Zygosaccharomyces bailii*, plasmid pSM1 from *Zygosaccharomyces fermentati*, plasmid pKD1 from *Kluyveromyces drosphilarum*, an un-named plasmid from *Pichia membranaefaciens* ("pPM1") and the 2 μm plasmid (such as shown in FIG. 1 of WO2006/067511) and variants (such as Scp1, Scp2 and Scp3) from *Saccharomyces cerevisiae* (Volkert, et al., 1989, *Microbiological Reviews* 53: 299; Murray et al., 1988, *J. Mol. Biol.* 200: 601; Painting, et al., 1984, *J. Applied Bacteriology* 56: 331).

A 2 μm-family plasmid typically comprises at least three open reading frames ("ORFs") that each encodes a protein that functions in the stable maintenance of the 2 μm-family plasmid as a multicopy plasmid. The proteins encoded by the three ORFs can be designated FLP, REP1 and REP2. Where a 2 μm-family plasmid comprises not all three of the ORFs encoding FLP, REP1 and REP2 then ORFs encoding the missing protein(s) should be supplied in trans, either on another plasmid or by chromosomal integration.

A preferred plasmid is the 2 μm plasmid from *S. cerevisiae*, preferably encoding a desired protein such as a heterologous protein.

The Gsh1 protein, Not4 protein and/or the desired, e.g. heterologous, protein may be encoded by a nucleotide sequence operably linked to one or more control sequences that direct the expression of the coding sequence in a suitable host cell under conditions compatible with the control sequences.

The polynucleotide may be manipulated in a variety of ways to provide for expression of a polypeptide. Manipulation of the polynucleotide prior to its insertion into a vector may be desirable or necessary depending on the expression vector. The techniques for modifying polynucleotides utilizing recombinant DNA methods are known in the art.

The control sequence may be a promoter, a polynucleotide which is recognized by a host cell for expression of the polynucleotide. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO96/00787), *Fusarium venenatum* amyloglucosidase (WO00/56900), *Fusarium venenatum* Daria (WO00/56900), *Fusarium venenatum* Quinn (WO00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, supra.

The control sequence may also be a transcription terminator, which is recognized by a host cell to terminate transcription. The terminator sequence is operably linked to the 3'-terminus of the polynucleotide encoding the polypeptide. Any terminator that is functional in the host cell may be used.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader sequence is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polypeptide-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Preferred signal peptides for yeast host cells, for example yeast host cells for the production of albumin, or variant, fragment and/or fusion thereof, include:

a signal peptide obtained from the gene for *Saccharomyces cerevisiae* alpha-factor, a signal peptide obtained from the gene for *Saccharomyces cerevisiae* invertase, a signal peptide obtained from the gene for *Saccharomyces cerevisiae* KEX2 e.g. comprising or consisting of SEQ ID NO: 17 or a modified KEX2 signal peptide sequence e.g. comprising or consisting of SEQ ID NO: 18.

Particularly preferred signal peptides include:

a signal peptide comprising a fusion of the mating factor alpha signal peptide sequence and the human albumin signal peptide sequence as taught in WO90/01063 (incorporated herein by reference), an example of such a signal peptide sequence is provided in SEQ ID NO: 19;

a signal peptide comprising the pentapeptide motif of SEQ ID NO: 20, wherein the pentapeptide motif is located in the hydrophobic domain of the signal peptide sequence, for example from positions −10 to −25 of an immature protein, where position −1 refers to the amino acid of the signal peptide sequence which is immediately adjacent the N-terminus of the first amino acid of the mature sequence, or for signal peptide sequences comprising a pro-peptide position −1 refers to the amino acid of the signal peptide sequence which is immediately adjacent the N-terminus of the first amino acid of the pro-peptide, examples of such signal peptide sequences are disclosed in WO2004/009819 (incorporated herein by reference);

an albumin signal peptide which is modified to comprise the pentapeptide motif of SEQ ID NO: 20, the pentapeptide motif may be located in the hydrophobic domain of the signal peptide sequence, an example of such a modified signal peptide sequence is provided in SEQ ID NO: 21. The pentapeptide motif may be inserted into an invertase signal peptide to generate a modified invertase signal peptide, examples of modified invertase signal peptides are provided in SEQ ID NO: 41 and SEQ ID NO: 42; or an albumin signal peptide which is modified to comprise the pentapeptide motif of SEQ ID NO: 20 and comprises a pro-peptide at the C' terminus of the signal peptide sequence, the pentapeptide motif may be located in the hydrophobic domain of the signal peptide sequence, examples of such a modified signal peptide sequence are provided in SEQ ID NO: 22, SEQ ID NO: 23 and SEQ ID NO: 24.

Signal peptides comprising of or consisting of SEQ ID NO: 19, SEQ ID NO: 24 and SEQ ID NO: 42 are especially preferred, for example for expression of albumin or a variant, fragment and/or fusion thereof.

Other useful signal peptide coding sequences are described by Romanos et al., 1992, supra.

The control sequence may also be a pro-peptide coding sequence that encodes a pro-peptide positioned at the N-terminus of a polypeptide. The resultant polypeptide is known as a proenzyme or pro-polypeptide (or a zymogen in some cases). A pro-polypeptide is generally inactive and can be converted to an active polypeptide by catalytic or autocatalytic cleavage of the pro-peptide from the pro-polypeptide. The pro-peptide coding sequence may be obtained from the genes for *Saccharomyces cerevisiae* alpha-factor.

Where both signal peptide and pro-peptide sequences are present, the pro-peptide sequence is positioned next to the N-terminus of the polypeptide and the signal peptide sequence is positioned next to the N-terminus of the pro-peptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. In yeast, the ADH2 system or GAL1 system may be used. In filamentous fungi, the *Aspergillus nigerglucoamylase* promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

The host strain may or may not express or overexpress one or more chaperone proteins such as those described in WO2005/061718, WO2006/067511, WO2006/136831 or WO2014/138371, all incorporated herein by reference. For example, the host strain may or may not overexpress one or more of: AHA1, CCT2, CCT3, CCT4, CCT5, CCT6, CCT7, CCT8, CNS1, CPR3, CPRE, ERO1, EUG1, FM01, HCH1, HSP10, HSP12, HSP104, HSP26, HSP30, HSP42, HSP60, HSP78, HSP82, JEM1, MDJ1, MDJ2, MPD1, MPD2, PDI1, PFD1, ABC1, APJ1, ATP11, ATP12, BTT1, CDC37, CPR7, HSC82, KAR2, LHS1, MGE1, MRS11, NOB1, ECM10, SSA1, SSA2, SSA3, SSA4, SSC1, SSE2, SIL1, SLS1, ORM1, ORM2, PERI, PTC2, PSE1, UBI4 and HAC1 or a truncated intronless HAC1 (Valkonen et al., 2003, *Applied Environ. Micro.*, 69: 2065), as well as TIM9, PAM18 (also known as TIM14) and TCP1 (also known as CCT1) or a variant thereof. Overexpression of PDI1 (SEQ ID NO: 25) or variant or fragment thereof and/or ERO1 (SEQ ID NO: 26) or variant or fragment thereof is preferred. Over-expression includes increasing the expression of the chaperone by at least 25, 50, 75, 100, 200, 300, 400, 500% relative to the native level expression of the chaperone in the host cell. Over-expression may correspond to an increase in chaperone amount, or an increase in chaperone activity. Overexpression may be achieved by increasing the copy number of the gene encoding the chaperone, for example by providing a host cell comprising 2, 3, 4, 5, 6, 7, 8, 9, 10 or more copies of the gene. Preferably the variant chaperone has at least 70, 75, 80, 85, 90, 91, 92, 93, 94, 95, 96, 97, 98 or 99% sequence identity to the chaperone. Preferably the variant maintains the functional activity of the chaperone.

The host cell may or may not comprise at least one heterologous nucleic acid encoding a protease or a fragment and/or variant thereof. The host cell may or may not comprise at least one nucleic acid encoding a protease such as a calcium dependent serine protease such as killer expression protease (Kex2p) or a fragment and/or variant thereof. Preferably the protease variant or fragment is functional, for example have the ability to cleave polypeptides at the carboxyl end of the recognition sequence Arg-Arg/X or Lys-Arg/X. A KEX2 nucleotide sequence may comprise or consist of SEQ ID NO: 27, a Kex2p protein may comprise or consist of SEQ ID NO: 28. Variants of KEX2 and Kex2p may have at least 70, 75, 80, 85, 90, 95, 96, 97, 98, or 99% identity to SEQ ID NO: 27 and SEQ ID NO: 28, respectively. KEX2 may or may not be overexpressed.

A preferred host cell, most preferably *S. cerevisiae*, overexpresses PDI1 and/or ERO1 and comprises at least one nucleic acid encoding Kex2p.

The nucleotide sequences encoding the Gsh1 protein, Not4 protein, or homolog thereof, and desired proteins can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare polypeptides.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO95/17413; or WO95/22625. Other methods that can be used include error-prone PCR, phage display (e.g., Lowman et al., 1991, *Biochemistry* 30: 10832-10837; U.S. Pat. No. 5,223,409; WO92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

A second aspect of the invention provides a culture of fungal host cells containing a polynucleotide sequence encoding a desired protein, such as a heterologous protein, characterised in that the fungal host cells have a modified, such as reduced, activity level of Gsh1 protein or homolog thereof and/or a modified, such as reduced, expression level of Gsh1 protein or homolog thereof.

The culture of fungal host cells according to the second aspect of the invention may additionally have a modified, such as reduced, activity level of Not4 protein or homolog thereof and/or a modified, such as reduced, expression level of Not4 protein or homolog thereof. The fungal host cells according to the second aspect of the invention are as described for the first aspect of the invention.

Alternatively, the second aspect of the invention provides a culture of fungal host cells containing a polynucleotide sequence encoding a desired protein, such as a heterologous protein, characterised in that the fungal host cells have an increased activity level of Gsh1 protein or homolog thereof and/or an increased expression level of Gsh1 protein or homolog thereof. This may be useful for the production of a desired protein that is detrimental to the viability of the host. The fungal host cells according to this alternative second aspect of the invention are as described for the first aspect of the invention.

The second aspect of the invention also provides a culture of fungal host cells containing a polynucleotide sequence encoding a desired protein, such as a heterologous protein, characterised in that the fungal host cells have (i) an increased activity level of Gsh1 protein or homolog thereof and/or an increased expression level of Gsh1 protein or homolog thereof and (ii) an increased activity level of Not4 protein or homolog thereof and/or an increased expression level of Not4 protein or homolog thereof. This may be useful for the production of a desired protein that is detrimental to the viability of the host. The fungal host cells according to this alternative second aspect of the invention are as described for the first aspect of the invention.

The method may comprise culturing in the presence of glutathione. This is particularly useful when the fungal host lacks a functional Gsh1 protein, for example due to mutation or deletion. It may also be useful when the fungal host cell contains a functional or partially functional Gsh1 protein. Glutathione may be present in the fermentation media at at least 0.05 mM, for example from about 0.05, 0.1, 0.2, 0.3, 0.4, 0.5, 0.6, 0.7, 0.8, 0.9, 1, 2, 3, 4, 5, 10, 20, 30, 40, 50, 60, 70, 80, 90, 100, 150, 200, 250, 300, 350, 400, 450 mM to about 0.1, 0.2, 0.3, 0.4, 0.5, 0.6, 0.7, 0.8, 0.9, 1, 2, 3, 4, 5, 10, 20, 30, 40, 50, 60, 70, 80, 90, 100, 150, 200, 250, 300, 350, 400, 450, 500 mM, preferably from about 0.5 to about 50 mM, more preferably from about 1 to about 10 mM, more preferably from about 3 to about 7 mM, most preferably at about 5 mM.

A third aspect of the invention provides a method for producing a desired protein, such as a heterologous protein, from a fungal host cell, the method comprising providing a fungal host cell according to the first aspect of the invention or a culture according to the second aspect of the invention and culturing the fungal host cell or culture to produce the desired protein. The method may be used to modify the production yield of a desired polypeptide from a fungal host cell. In some cases, it may be desirable to increase the production yield of one or more proteins. In other cases, it may be desirable to decrease the production yield of one or more proteins, such as proteins that may be toxic to the host cell.

The desired protein may or may not be secreted from the host cell, a secreted protein is preferred.

The host cells may be cultivated in a nutrient medium suitable for production of the desired protein using methods known in the art. For example, the cell may be cultivated by shake flask cultivation, or small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation may take place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). Preferred media include MW11D as described in Example 5. If the desired protein is secreted into the nutrient medium, the desired protein may be recovered directly from the medium. If the desired protein is not secreted, it may be recovered from cell lysates.

The culturing may be at small or large scale, for example microtiter plate scale (e.g. from 10 to 500 microliter culture volume media), shake flask scale (e.g. from 5 to 1000 milliliter (mL) culture volume), or fermenter or equivalent systems scale (e.g. at least from 5 mL culture volume, more preferably at least 1, 2, 3, 4 or 5 liter (L), more preferably at least 10, 50, 100 L, for example at least 500, 1000, 2000, 3000, 4000, 5000, 6000, 7000, 8000, 9000, 10000, 20000, 30000 L culture volume).

The culturing may be at a pH suitable for the host cell. For *S. cerevisiae*, preferably the pH is from 5 to 7, for example from 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, or 6.9 to 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9 or 7. A preferred pH range is about 6.0 to about 6.4.

The culturing may be at a temperature of from about 20° C. to about 35° C., for example from about 20, 21, 22, 23, 24, 25, 26, 27, 28, 29, 30, 31, 32, 33, 34° C. to about 21, 22, 23, 24, 25, 26, 27, 28, 29, 30, 31, 32, 33, 34 or 35° C., preferably from about 28 to about 32° C., more preferably about 30° C.

The culturing may or may not involve agitation, for example rotating of the culture vessel or by use of an agitator within the culture vessel. Agitation is preferred.

The desired protein may be detected using methods known in the art that are specific for the desired protein. These detection methods include, but are not limited to, use of specific antibodies, or high performance liquid chromatography (HPLC).

A preferred HPLC is gel permeation HPLC (GP-HPLC). Suitable equipment includes a LC2010 HPLC system (Shimadzu) equipped with UV detection under Shimadzu VP7.3 client server software control. Injections of 75 μL may be made onto a 7.8 mm id×300 mm length TSK G3000SWXL column (Tosoh Bioscience), with a 6.0 mm id×40 mm length TSK SW guard column (Tosoh Bioscience). Samples may be chromatographed in 25 mM sodium phosphate, 100 mM sodium sulfate, 0.05% (w/v) sodium azide, pH 7.0 at 1 mL·min$^{-1}$, with a run time of 20 minutes. Samples may be quantified by UV detection at 280 nm, by peak area, relative to a recombinant human albumin standard of known concentration (e.g. 10 mg/mL) and corrected for their relative extinction coefficients.

Optionally, the method comprises recovering the desired protein, for example isolating the desired protein from the host cell or host cell culture, e.g. cell media or cell lysate.

The desired protein may be recovered using methods known in the art. For example, the desired protein may be recovered from the nutrient medium by conventional procedures including, but not limited to, collection, centrifugation, filtration, extraction, spray-drying, evaporation, or precipitation.

Optionally, the method comprises purifying the desired protein. The desired protein may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure desired proteins.

In an alternative aspect, the desired protein is not recovered, but rather a host cell of the present invention expressing the desired protein is used as a source of the desired protein.

The step of purifying the desired protein (such as a desired heterologous protein) from the cultured host cell or the culture medium optionally comprises cell immobilization, cell separation and/or cell breakage, but always comprises at least one other purification step different from the step or steps of cell immobilization, separation and/or breakage.

Cell immobilization techniques, such as encasing the cells using calcium alginate bead, are known in the art. Similarly, cell separation techniques, such as centrifugation, filtration (e.g. cross-flow filtration), expanded bed chromatography and the like are known in the art. Likewise, methods of cell breakage, including beadmilling, sonication, enzymatic exposure and the like are known in the art.

The at least one other purification step may be any other step suitable for protein purification known in the art. For example purification techniques for the recovery of recombinantly expressed albumin have been disclosed in: WO2010/128142, affinity purification using an albumin specific ligand such as 2-chloro-4,6-di(2'-sulphoanilino)-S-triazine, WO92/04367, removal of matrix-derived dye; EP464590, removal of yeast-derived colorants; EP319067, alkaline precipitation and subsequent application of the albumin to a lipophilic phase; and WO96/37515, U.S. Pat. No. 5,728,553 and WO00/44772, which describe complete purification processes; all of which are incorporated herein by reference.

Desired proteins other than albumin may be purified from the culture medium by any technique that has been found to be useful for purifying such proteins.

Suitable methods include ammonium sulfate or ethanol precipitation, acid or solvent extraction, anion or cation exchange chromatography, phosphocellulose chromatography, hydrophobic interaction chromatography, affinity chromatography, hydroxylapatite chromatography, lectin chromatography, concentration, dilution, pH adjustment, diafiltration, ultrafiltration, high performance liquid chromatography ("HPLC"), reverse phase HPLC, conductivity adjustment and the like.

Optionally, the method may comprise purifying the isolated protein to a commercially or industrially acceptable level of purity. By commercially or industrially acceptable level of purity, we include the provision of the protein at a concentration of at least 0.01 g·L$^{-1}$, 0.02 g·L$^{-1}$, 0.03 g·L$^{-1}$, 0.04 g·L$^{-1}$, 0.05 g·L$^{-1}$, 0.06 g·L$^{-1}$, 0.07 g·L$^{-1}$, 0.08 g·L$^{-1}$, 0.09 g·L$^{-1}$, 0.1 g·L$^{-1}$, 0.2 g·L$^{-1}$, 0.3 g·L$^{-1}$, 0.4 g·L$^{-1}$, 0.5 g·L$^{-1}$, 0.6 g·L$^{-1}$, 0.7 g·L$^{-1}$, 0.8 g·L$^{-1}$, 0.9 g·L$^{-1}$, 1 g·L$^{-1}$, 2 g·L$^{-1}$, 3 g·L$^{-1}$, 4 g·L$^{-1}$, 5 g·L$^{-1}$, 6 g·L$^{-1}$, 7 g·L$^{-1}$, 8 g·L$^{-1}$, 9 g·L$^{-1}$, 10 g·L$^{-1}$, 15 g·L$^{-1}$, 20 g·L$^{-1}$, 25 g·L$^{-1}$, 30 g·L$^{-1}$, 40 g·L$^{-1}$, 50 g·L$^{-1}$, 60 g·L$^{-1}$, 70 g·L$^{-1}$, 80 g·L$^{-1}$, 90 g·L$^{-1}$, 100 g·L$^{-1}$, 150 g·L$^{-1}$, 200 g·L$^{-1}$, 250 g·L$^{-1}$, 300 g·L$^{-1}$, 350 g·L$^{-1}$, 400 g·L$^{-1}$, 500 g·L$^{-1}$, 600 g·L$^{-1}$, 700 g·L$^{-1}$, 800 g·L$^{-1}$, 900 g·L$^{-1}$, 1000 g·L$^{-1}$, or more. By commercially or industrially acceptable level of purity, we include the provision of the isolated protein in which other material (for example, one or more (e.g. several) contaminants) are present at a level of less than 50%, 40%, 30%, 20%, 10%, 5%, 4%, 3%, 2%, 1%, 0.5%, 0.1%, 0.01%, 0.001%, 0.0001%, 0.00001%, or 0.000001% and, most preferably at a level of 0%.

The protein may be provided at a concentration of at least 0.01 g·L$^{-1}$, 0.02 g·L$^{-1}$, 0.03 Oil, 0.04 g·L$^{-1}$, 0.05 Oil, 0.06 g·L$^{-1}$, 0.07 g·L$^{-1}$, 0.08 g·L$^{-1}$, 0.09 g·L$^{-1}$, 0.1 g·L$^{-1}$, 0.2 g·L$^{-1}$, 0.3 g·L$^{-1}$, 0.4 g·L$^{-1}$, 0.5 g·L$^{-1}$, 0.6 g·L$^{-1}$, 0.7 g·L$^{-1}$, 0.8 Oil, 0.9 g·L$^{-1}$, 1 g·L$^{-1}$, 2 g·L$^{-1}$, 3 g·L$^{-1}$, 4 g·L$^{-1}$, 5 g·L$^{-1}$, 6 g·L$^{-1}$, 7 g·L$^{-1}$, 8 g·L$^{-1}$, 9 g·L$^{-1}$, 10 g·L$^{-1}$, 15 g·L$^{-1}$, 20 g·L$^{-1}$, 25 g·L$^{-1}$, 30 g·L$^{-1}$, 40 g·L$^{-1}$, 50 g·L$^{-1}$, 60 g·L$^{-1}$, 70 g·L$^{-1}$, 80 g·L$^{-1}$, 90 g·L$^{-1}$, 100 g·L$^{-1}$, 150 g·L$^{-1}$, 200 g·L$^{-1}$, 250 g·L$^{-1}$, 300 g·L$^{-1}$, 350 g·L$^{-1}$, 400 g·L$^{-1}$, 500 g·L$^{-1}$, 600 g·L$^{-1}$, 700 g·L$^{-1}$, 800 g·L$^{-1}$, 900 g·L$^{-1}$, 1000 g·L$^{-1}$, or more.

It is preferred that the desired protein is purified to achieve a pharmaceutically acceptable level of purity. A protein has a pharmaceutically acceptable level of purity if it is essentially pyrogen free and can be administered in a pharmaceutically efficacious amount without causing medical effects not associated with the activity of the protein.

Optionally, the method further comprises formulating the desired protein with a therapeutically acceptable carrier or diluent thereby to produce a therapeutic product suitable for administration to a human or an animal.

The resulting desired protein may, or may not, be used for any of its known utilities, which, in the case of albumin, include intra venous (i.v.) administration to patients to treat severe burns, shock and blood loss, supplementing culture media, and as an excipient in formulations of other proteins.

Although it is possible for a therapeutically, diagnostically, industrially, domestically or nutritionally useful desired protein obtained by a process of the invention to be presented or administered alone, it is preferable to present it as a formulation (such as a pharmaceutical formulation, particularly in the case of therapeutically and/or diagnostically useful proteins), together with one or more acceptable carriers or diluents. The carrier(s) or diluent(s) must be "acceptable" in the sense of being compatible with the desired protein and, where the formulation is intended for administration to a recipient, then not deleterious to the recipient thereof. Typically, the carriers or diluents will be water or saline which will be sterile and pyrogen free.

Optionally the thus formulated protein will be presented in a unit dosage form, such as in the form of a tablet, capsule, injectable solution or the like.

Optionally, the method further comprises providing the desired protein in unit dosage form.

A fourth aspect of the invention provides a method for increasing the yield of a desired protein (such as a heterologous protein) comprising the method according to the third aspect of the invention.

The fourth aspect of the invention also provides use of a host cell according to the first aspect of the invention or a culture according to the second aspect of the invention to increase the yield of a desired protein (such as a heterologous protein).

Yield refers to the amount of product, for example desired protein, in solution, for example culture broth or cell lysis mixture. Yield may be expressed in relative terms, e.g. the yield from a reference host strain being 100%. When comparing host strains, it is preferred that the yield is measured under a defined set of conditions. Absolute yield may be expressed as nanograms per microliter (ng/μL) or grams per liter (g/L). Yield may alternatively be expressed as rate of specific cellular productivity ($Y_{PXT}$).

Preferably, the yield of the desired protein is at least 2% higher than the yield (g/L or $Y_{PXT}$) from a reference fungal host cell such as a fungal host cell having a wild-type Gsh1 protein, such as SEQ ID NO: 2, more preferably at least 3, 4, 5, 6, 7, 8, 9, 10, 12.5, 15, 17.5, 20, 22.5, 25, 27.5, 30, 35, 40, 45, or at least 50% higher. A preferred reference fungal host cell has a Gsh1 protein of SEQ ID NO: 2.

Preferably, the yield of the desired protein is at least 2% higher than the yield (g/L or $Y_{PXT}$) from a reference fungal host cell such as a fungal host cell having a wild-type Not4 protein, such as SEQ ID NO: 6, more preferably at least 3, 4, 5, 6, 7, 8, 9, 10, 12.5, 15, 17.5, 20, 22.5, 25, 27.5, 30, 35, 40, 45, or at least 50% higher. A preferred reference fungal host cell has a Not4 protein of SEQ ID NO: 6.

Preferably, the yield of the desired protein is at least 2% higher than the yield (g/L or $Y_{PXT}$) from a reference fungal host cell such as a fungal host cell having a wild-type Gsh1 protein, such as SEQ ID NO: 2, and a wild-type Not4 protein, such as SEQ ID NO: 6, more preferably at least 3, 4, 5, 6, 7, 8, 9, 10, 12.5, 15, 17.5, 20, 22.5, 25, 27.5, 30, 35, 40, 45, or at least 50% higher. A preferred reference fungal host cell has a Gsh1 protein of SEQ ID NO: 2 and a Not4 protein of SEQ ID NO: 6.

The desired protein may be as described for the first aspect of the invention, especially an albumin or variant, fragment and/or fusion thereof.

A fifth aspect of the invention provides a desired protein (such as a heterologous protein) produced by the method according to the third or fourth aspect of the invention.

The invention also provides a composition, such as a pharmaceutical composition, comprising the desired protein of the fifth aspect of the invention. The pharmaceutical composition may comprise one or more pharmaceutically acceptable carriers such as those approved by a regulatory authority such as the US Food and Drug Administration or European Medicines Agency. The invention further provides a method of treating a patient comprising administering an effective amount of the pharmaceutical composition to the patient.

A sixth aspect of the invention provides a method of preparing a fungal host cell according to the first aspect of the invention or a culture according to the second aspect of the invention. The method comprises genetically modifying a (parent) fungal host cell to modify the resultant Gsh1 protein or homolog thereof, to modify, e.g. reduce, the activity level of Gsh1 protein or homolog thereof, to modify a GSH1 gene or homolog thereof or a control sequence thereof or to modify the expression level of a GSH1 gene or homolog thereof. Optionally, the method may also comprise genetically modifying the (parent) fungal host cell to modify the resultant Not4 protein or homolog thereof, to modify, e.g. reduce, the activity level of Not4 protein or homolog thereof, to modify a NOT4 gene or homolog thereof or a control sequence thereof or to modify the expression level of a NOT4 gene or homolog thereof. Mutations, deletions and modification of activity and/or expression levels may be as described for the first, second, and third aspects of the invention. Methods for engineering host cells are known in the art. As an alternative to genetic modification of the host cell, the level of Gsh1 protein or activity may be modified by addition of an inhibitor or enhancer to the growth media. Likewise, an alternative to genetic modification of the host cell, the level of Not4 protein or activity may be modified by addition of an inhibitor or enhancer to the growth media.

A seventh aspect of the invention provides a Gsh1 protein, or homolog thereof, comprising at least 50% identity to SEQ ID NO: 2 and a mutation at a position corresponding to one or more positions selected from 47, 48, 49, 50, 51, 120, 121, 122, 123, 124, 125, 126, 127, 128, 129, 130, 409, 451, 452, 453, 454 and 455 of SEQ ID NO: 2, preferably a position selected from (a) 57 to 51; (b) 120 to 130; (c) 409 or (d) 451 to 455. A mutation at a position corresponding to position 125 of SEQ ID NO: 2 is particularly preferred.

The Gsh1 protein according to the seventh aspect of the invention may be as described in relation to the first aspect of the invention. Preferably the Gsh1 protein comprises or consists of SEQ ID NO: 4. The Gsh1 protein of the seventh aspect of the invention may or may not be an isolated protein.

An eighth aspect of the invention provides a polynucleotide encoding a Gsh1 variant of the present invention, such as a variant of SEQ ID NO: 2 which results in a lower level of Gsh1 protein expression, or homolog thereof, and/or a lower activity level of Gsh1 protein, or homolog thereof, than a host cell encoding a wild-type Gsh1 protein such as SEQ ID NO: 2, or homolog thereof. Such Gsh1 proteins are described in the first to sixth aspects of the invention.

A preferred polynucleotide encodes a Gsh1 protein with the mutation R125G (SEQ ID NO: 4), an example of such a polynucleotide sequence is provided by SEQ ID NO: 3.

For example, the present invention also relates to nucleic acid constructs comprising a polynucleotide encoding a Gsh1 variant of the present invention operably linked to one or more control sequences that direct the expression of the coding sequence in a suitable host cell under conditions compatible with the control sequences. Suitable control sequences are described in the first to seventh aspects of the invention.

The nucleic acid construct may additionally comprise a polynucleotide encoding a Not4 variant of the present invention operably linked to one or more control sequences that direct the expression of the coding sequence in a suitable host cell under conditions compatible with the control sequences. Suitable control sequences are described in the first to sixth aspects of the invention.

The polynucleotide(s) may be located on a vector or in the genome of the host cell.

Consequently, the present invention also relates to recombinant vectors comprising a polynucleotide encoding a Gsh1 variant of the present invention, a promoter, and transcriptional and translational stop signals. Optionally, the vector further comprises a polynucleotide encoding a Not4 variant of the present invention, a promoter, and transcriptional and translational stop signals. The Gsh1 may be encoded on the same polynucleotide (e.g. vector) or on a different polynucleotide (e.g. vector) to Not4. The invention also relates to vectors comprising a polynucleotide encoding Gsh1 and one or more (e.g. several) control sequences which cause the level of Gsh1 or Gsh1 activity to be modified, for example reduced. Optionally, the polynucleotides (e.g. vectors) further comprise a polynucleotide encoding Not4 and one or more (e.g. several) control sequences which cause the level of Not4 or Not4 activity to be modified, for example reduced. The various nucleotide and control sequences may be joined together to produce a recombinant vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the vector, the coding sequence is located in the vector so that the coding sequence is operably linked with the appropriate control sequences for expression.

The recombinant vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permits selection of transformed, transfected, transduced, or the like cells. A selectable marker is a gene, the product of which provides for biocide or viral resistance, resistance to heavy metals, prototrophy to auxotrophs, and the like.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2-micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO00/24883). Isolation of the AMA1 gene and construction of plasmids or vectors comprising the gene can be accomplished according to the methods disclosed in WO00/24883.

More than one copy of a polynucleotide of the present invention may be inserted into a host cell to increase production of a desired protein. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant vectors of the present invention are known to one skilled in the art (see, e.g., Sambrook et al., 1989, Molecular Cloning, A Laboratory Manual, 2d edition, Cold Spring Harbor, N.Y.).

PREFERRED EMBODIMENTS

1. A fungal host cell having a modified:
   a. Gsh1 protein or homolog thereof, and/or
   b. activity level or expression level of Gsh1 protein or homolog thereof, and/or
   c. GSH1 gene or homolog thereof, and/or
   d. level of expression of GSH1 gene or homolog thereof.
2. The fungal host cell of embodiment 1, wherein the modified level is a reduced level.
3. The fungal host cell of embodiment 1, wherein the modified level is an increased level.
4. The fungal host cell of any preceding embodiment, wherein the modified level is relative to the level of a reference fungal host cell, such as:
   a. a fungal host cell in which the Gsh1 protein or homolog thereof is a wild-type Gsh1 protein or homolog thereof,
   b. a fungal host cell in which the Gsh1 protein comprises or consists of SEQ ID NO: 2,
   c. S. cerevisiae S288C or
   d. S. cerevisiae DXY1.
5. The fungal host of any of embodiments 1 to 4 having a modified:
   e. Not4 protein or homolog thereof, and/or
   f. activity level or expression level of Not4 protein or homolog thereof, and/or
   g. NOT4 gene or homolog thereof, and/or
   h. level of expression of NOT4 gene or homolog thereof,
6. The fungal host cell of embodiment 5, wherein the modified level is a reduced level.
7. The fungal host cell of embodiment 5, wherein the modified level is an increased level.
8. The fungal host cell of embodiment 5 or 6, wherein the modified level is relative to the level of a reference fungal host cell, such as:
   a. a fungal host cell in which the Not4 protein or homolog thereof is a wild-type Not4 protein or homolog thereof,
   b. a fungal host cell in which the Not4 protein comprises or consists of SEQ ID NO: 6,
   c. S. cerevisiae S288C or
   d. S. cerevisiae DXY1.
9. The fungal host cell according to any preceding embodiment, comprising a nucleotide sequence encoding a desired protein such as heterologous protein.
10. The fungal host cell according to embodiment 9 in which the desired protein is selected from albumin, a monoclonal antibody, an etoposide, a serum protein (such as a blood clotting factor), antistasin, a tick anticoagulant peptide, transferrin, lactoferrin, endostatin, angiostatin, collagens, immunoglobulins or immunoglobulin-based molecules or fragment of either (e.g. a Small Modular ImmunoPharmaceutical™ ("SMIP") or dAb, Fab' fragments, F(ab')2, scAb, scFv or scFv fragment), a Kunitz domain protein (such as those described in WO03/066824 (incorporated herein by reference), with or without albumin fusions), interferons, interleukins, IL-10, IL-11, IL-2, interferon α (alpha) species and sub-species, interferon β (beta) species and sub-species, interferon γ (gamma) species and sub-species, leptin, CNTF, $CNTF_{Ax15}$, IL-1-receptor antagonist, erythropoietin (EPO) and EPO mimics, thrombopoietin (TPO) and TPO mimics, prosaptide, cyanovirin-N, 5-helix, T20 peptide, T1249 peptide, HIV gp41, HIV gp120, urokinase, prourokinase, tPA, hirudin, platelet derived growth factor, parathyroid hormone, proinsulin, insulin, glucagon, glucagon-like peptides such as exendin-4, GLP-1 or GLP-2, insulin-like growth factor, calcitonin, growth hormone, transforming growth factor β (beta), tumour necrosis factor, G-CSF, GM-CSF, M-CSF, FGF, coagulation factors in both pre and active forms, including but not limited to plasminogen, fibrinogen, thrombin, pre-thrombin, pro-thrombin, von Willebrand's factor, $alpha_1$-antitrypsin, plasminogen activators, Factor VII, Factor VIII, Factor IX, Factor X and Factor XIII, nerve growth factor, LACI, platelet-derived endothelial cell growth factor (PD-ECGF), glucose oxidase, serum cholinesterase, aprotinin, amyloid precursor protein, inter-alpha trypsin inhibitor, antithrombin III, apo-lipoprotein species, Protein C, Protein S, a metabolite, an antibiotic, or a variant or fragment of any of the above.
11. The fungal host cell according to embodiment 9 or 10 in which the desired protein comprises or consists of an albumin, variant, fragment and/or fusion thereof.
12. The fungal host cell according to embodiment 11 in which the albumin or variant, fragment and/or fusion thereof has at least 70% identity to SEQ ID NO: 10.
13. The fungal host cell according to embodiment 11 in which the albumin or variant, fragment and/or fusion thereof has at least 75, 80, 85, 90, 91, 92, 93, 95, 96, 97, 98 or 99% identity to SEQ ID NO: 10.
14. The fungal host cell according to embodiment 13 in which the albumin or variant, fragment and/or fusion thereof has at least 70% identity to SEQ ID NO: 10, preferably at least 75, 80, 85, 90, 91, 92, 93, 95, 96, 97, 98 or 99% identity to SEQ ID NO: 10, and comprises A, C, D, E, F, G, H, I, L, M, N, P, Q, R, S, T, V, W or Y at a position corresponding to K573 of SEQ ID NO: 10.
15. The fungal host cell according to embodiment 14 in which albumin or variant, fragment and/or fusion thereof comprises a P, H, W or Y at a position corresponding to K573 of SEQ ID NO: 10.
16. The fungal host cell according to embodiment 15 in which the albumin variant, fragment and/or fusion thereof has at least 98% identity to SEQ ID NO: 10, and comprises a P at a position corresponding to K573 of SEQ ID NO: 10.
17. The fungal host cell according to any of embodiments 13 to 16 in which the albumin or variant, fragment and/or fusion thereof has at least 70% identity to SEQ ID NO: 10, preferably at least 75, 80, 85, 90, 91, 92, 93, 95, 96, 97, 98 or 99% identity to SEQ ID NO: 10, and comprises A, C, D, F, G, H, I, K, L, M, N, P, Q, R, S, T, V, W or Y at a position corresponding to E492 of SEQ ID NO: 10.
18. The fungal host cell according to embodiment 17 in which albumin or variant, fragment and/or fusion thereof comprises a G, D, F, H, M or R at a position corresponding to E492 of SEQ ID NO: 10.

19. The fungal host cell according to embodiment 18 in which the albumin variant, fragment and/or fusion thereof has at least 98% identity to SEQ ID NO: 10, and comprises a G or D at a position corresponding to E492 of SEQ ID NO: 10.

20. The fungal host cell according to embodiment 19 in which the albumin variant, fragment and/or fusion thereof has at least 98% identity to SEQ ID NO: 10, and comprises a G at a position corresponding to E492 of SEQ ID NO: 10.

21. The fungal host cell according to any of embodiments 13 to 20 in which the albumin or variant, fragment and/or fusion thereof has at least 70% identity to SEQ ID NO: 10, preferably at least 75, 80, 85, 90, 91, 92, 93, 95, 96, 97, 98 or 99% identity to SEQ ID NO: 10, and comprises A, C, D, E, F, G, H, I, L, M, N, P, Q, R, S, T, V, W or Y at a position corresponding to K574 of SEQ ID NO: 10.

22. The fungal host cell according to embodiment 21 in which albumin or variant, fragment and/or fusion thereof comprises a H, G, D, F, N, S or Y at a position corresponding to K574 of SEQ ID NO: 10.

23. The fungal host cell according to embodiment 22 in which the albumin variant, fragment and/or fusion thereof has at least 98% identity to SEQ ID NO: 10, and comprises a D, F, G or H at a position corresponding to K574 of SEQ ID NO: 10.

24. The fungal host cell according to embodiment 23 in which the albumin variant, fragment and/or fusion thereof has at least 98% identity to SEQ ID NO: 10, and comprises an H at a position corresponding to K574 of SEQ ID NO: 10.

25. The fungal host cell according to any of embodiments 13 to 24 in which the albumin or variant, fragment and/or fusion thereof has at least 70% identity to SEQ ID NO: 10, preferably at least 75, 80, 85, 90, 91, 92, 93, 95, 96, 97, 98 or 99% identity to SEQ ID NO: 10, and comprises A, C, D, E, F, G, H, I, K, L, M, N, P, R, S, T, V, W or Y at a position corresponding to Q580 of SEQ ID NO: 10.

26. The fungal host cell according to embodiment 25 in which albumin or variant, fragment and/or fusion thereof comprises a K or R at a position corresponding to Q580 of SEQ ID NO: 10.

27. The fungal host cell according to embodiment 26 in which the albumin variant, fragment and/or fusion thereof has at least 98% identity to SEQ ID NO: 10, and comprises a K at a position corresponding to K573 of SEQ ID NO: 10.

28. The fungal host cell according to any of embodiments 13 to 26 in which the albumin fusion comprises the albumin variant of SEQ ID NO: 45.

29. The fungal host cell according to any of embodiments 13 to 26 in which the albumin variant comprises or consists of SEQ ID NO: 45.

30. The fungal host cell according to any of embodiments 11 to 29 in which the fusion comprises a fusion partner which is not albumin or a variant or a fragment or fusion thereof.

31. The fungal host cell according to any of embodiments 12 to 30 in which the fusion comprises a fusion partner selected from monoclonal antibody, an etoposide, a serum protein (such as a blood clotting factor), antistasin, a tick anticoagulant peptide, transferrin, lactoferrin, endostatin, angiostatin, collagens, immunoglobulins or immunoglobulin-based molecules or fragment of either (e.g. a Small Modular ImmunoPharmaceutical™ ("SMIP") or dAb, Fab' fragments, F(ab')2, scAb, scFv or scFv fragment), a Kunitz domain protein (such as those described in WO03/066824 (incorporated herein by reference), interferons, interleukins, IL-10, IL-11, IL-2, interferon α (alpha) species and sub-species, interferon β (beta) species and sub-species, interferon γ (gamma) species and sub-species, leptin, CNTF, $CNTF_{Ax15}$, IL-1-receptor antagonist, erythropoietin (EPO) and EPO mimics, thrombopoietin (TPO) and TPO mimics, prosaptide, cyanovirin-N, 5-helix, T20 peptide, T1249 peptide, HIV gp41, HIV gp120, urokinase, prourokinase, tPA, hirudin, platelet derived growth factor, parathyroid hormone, proinsulin, insulin, glucagon, glucagon-like peptides such as exendin-4, GLP-1 or GLP-2, insulin-like growth factor, calcitonin, growth hormone, transforming growth factor β (beta), tumour necrosis factor, G-CSF, GM-CSF, M-CSF, FGF, coagulation factors in both pre and active forms, including but not limited to plasminogen, fibrinogen, thrombin, pre-thrombin, pro-thrombin, von Willebrand's factor, $alpha_1$-antitrypsin, plasminogen activators, Factor VII, Factor VIII, Factor IX, Factor X and Factor XIII, nerve growth factor, LACI, platelet-derived endothelial cell growth factor (PD-ECGF), glucose oxidase, serum cholinesterase, aprotinin, amyloid precursor protein, inter-alpha trypsin inhibitor, antithrombin III, apo-lipoprotein species, Protein C, Protein S, a metabolite, an antibiotic, or a variant or fragment of any of the above.

32. The fungal host cell according to embodiment 30 or 31 in which the fusion partner comprises or consists of a glucagon-like protein or analog thereof.

33. The fungal host cell according to embodiment 32 in which the fusion partner comprises or consists of SEQ ID NO: 14, SEQ ID NO: 15, SEQ ID NO: 51, or SEQ ID NO: 52.

34. The fungal host cell according any of embodiments 9 to 33 in which the desired protein comprises or consists of SEQ ID NO: 16.

35. The fungal host cell according to any preceding embodiment in which the modified activity level and/or expression level of Gsh1 protein or homolog thereof is relative to the activity level or expression level of Gsh1 protein or homolog thereof of a parent fungal host cell such as a wild-type fungal host cell.

36. The fungal host cell according to embodiment 35, in which the activity level and/or expression level of Gsh1 protein or homolog thereof is reduced to no more than 99% of the activity level or expression level of Gsh1 protein or homolog thereof of the parent fungal host cell.

37. The fungal host cell according to embodiment 36, in which the activity level and/or expression level of Gsh1 protein or homolog thereof is reduced to no more than 95% of the activity level or expression level of Gsh1 protein or homolog thereof of the parent fungal host cell.

38. The fungal host cell according to embodiment 37, in which the activity level and/or expression level of Gsh1 protein or homolog thereof is reduced to no more than 90% of the activity level or expression level of Gsh1 protein or homolog thereof of the parent fungal host cell.

39. The fungal host cell according to embodiment 38, in which the activity level and/or expression level of Gsh1 protein or homolog thereof is reduced to no more than 80% of the activity level or expression level of Gsh1 protein or homolog thereof of the parent fungal host cell.

40. The fungal host cell according to embodiment 39, in which the activity level and/or expression level of Gsh1 protein or homolog thereof is reduced to no more than 70% of the activity level or expression level of Gsh1 protein or homolog thereof of the parent fungal host cell.

41. The fungal host cell according to embodiment 40, in which the activity level and/or expression level of Gsh1 protein or homolog thereof is reduced to no more than 60% of the activity level or expression level of Gsh1 protein or homolog thereof of the parent fungal host cell.

42. The fungal host cell according to embodiment 41 in which the activity level and/or expression level of Gsh1 protein or homolog thereof is reduced to no more than 50% of the activity level or expression level of Gsh1 protein or homolog thereof of the parent fungal host cell.

43. The fungal host cell according to embodiment 42, in which the activity level and/or expression level of Gsh1 protein or homolog thereof is reduced to no more than 40% of the activity level or expression level of Gsh1 protein or homolog thereof of the parent fungal host cell.

44. The fungal host cell according to embodiment 43, in which the activity level and/or expression level of Gsh1 protein or homolog thereof is reduced to no more than 30%, preferably not more than 20%, of the activity level or expression level of Gsh1 protein or homolog thereof of the parent fungal host cell.

45. The fungal host cell according to embodiment 44, in which the activity level and/or expression level of Gsh1 protein or homolog thereof is reduced to substantially 0% of the activity level or expression level of Gsh1 protein or homolog thereof of the parent fungal host cell.

46. The fungal host cell according to any preceding embodiment, in which the host cell lacks a functional GSH1 gene or homolog thereof or functional Gsh1 protein or homolog thereof.

47. The fungal host cell according to any preceding embodiment, in which the host cell lacks a GSH1 gene or homolog thereof or Gsh1 protein or homolog thereof.

48. The fungal host cell according to any preceding embodiment in which the Gsh1 protein or homolog thereof comprises a mutation at position corresponding to a position selected from 47, 48, 49, 50, 51, 120, 121, 122, 123, 124, 125, 126, 127, 128, 129, 130, 409, 451, 452, 453, 454 and 455 of SEQ ID NO: 2.

49. The fungal host cell according to embodiment 48 in which the position corresponds to R125 of SEQ ID NO: 2.

50. The fungal host cell according to embodiment 48 or 49 in which the position corresponds to H409 of SEQ ID NO: 2.

51. The fungal host cell according to any of embodiments 48 to 50 in which the position corresponds to P453 of SEQ ID NO: 2.

52. The fungal host cell according to any of embodiments 48 to 51 in which the mutation is a substitution, preferably to a non-conserved amino acid.

53. The fungal host cell according to embodiment 52 in which the mutation at a position corresponding to position 125 of SEQ ID NO: 2 is a substitution to A, C, D, E, F, G, H, I, L, M, N, P, Q, S, T, V, W or Y, preferably to C, D, E or G, more preferably to G.

54. The fungal host cell according to any of embodiments 48 to 53 in which the mutation at a position corresponding to position 125 of SEQ ID NO: 2 is from a positively charged amino acid to an aliphatic, aromatic, hydrophobic, small, tiny, polar or negatively charged amino acid, preferably a negatively charged amino acid to a tiny amino acid.

55. The fungal host cell according to any of embodiments 48 to 54 in which the mutation at a position corresponding to position D49 of SEQ ID NO: 2 is a substitution to A, C, F, G, H, I, K, L, M, N, P, Q, R, S, T, V, W or Y, preferably to H, K or R, more preferably to K or R.

56. The fungal host cell according to any of embodiments 48 to 55 in which the mutation at a position corresponding to position 49 of SEQ ID NO: 2 is from a negatively charged amino acid to a positively charged amino acid.

57. The fungal host cell according to any of embodiments 48 to 56 in which the mutation at a position corresponding to position H409 of SEQ ID NO: 2 is a substitution to A, C, D, E, F, G, I, K, L, M, N, P, Q, R, S, T, V, W or Y, preferably to A, I, L, V, M, F, W, Y, more preferably to A, I, L, V, most preferably to L.

58. The fungal host cell according to any of embodiments 48 to 57 in which the mutation at a position corresponding to position H409 of SEQ ID NO: 2 is from an aromatic amino acid to an aliphatic amino acid.

59. The fungal host cell according to any of embodiments 48 to 58 in which the mutation at a position corresponding to position P453 of SEQ ID NO: 2 is a substitution to A, C, D, E, F, G, H, I, K, L, M, N, Q, R, S, T, V, W or Y, preferably to A, I, L, V, M, F, W, Y, more preferably to A, I, L, V, most preferably to L.

60. The fungal host cell according any of embodiments 48 to 59 in which the mutation at a position corresponding to position P453 of SEQ ID NO: 2 is from an aromatic amino acid to an aliphatic amino acid.

61. The fungal host cell according to any preceding embodiment in which the Gsh1 protein comprises or consists of SEQ ID NO: 4.

62. The fungal host cell according to any preceding embodiment comprising a modified GSH1 gene, for example a polynucleotide encoding SEQ ID NO: 4.

63. The fungal host cell according to any of embodiments 5 to 62 in which the modified activity level or expression level of Not4 protein or homolog thereof is relative to the activity level or expression level of Not4 protein or homolog thereof of a parent fungal host cell such as a wild-type fungal host cell.

64. The fungal host cell according to embodiment 63, in which the activity level and/or expression level of Not4 protein or homolog thereof is reduced to no more than 90% of the activity level and/or expression level of Not4 protein or homolog thereof of the parent fungal host cell.

65. The fungal host cell according to embodiment 64, in which the activity level and/or expression level of Not4 protein or homolog thereof is reduced to no more than 80% of the activity level and/or expression level of Not4 protein or homolog thereof of the parent fungal host cell.

66. The fungal host cell according to embodiment 65, in which the activity level and/or expression level of Not4 protein or homolog thereof is reduced to no more than 70% of the activity level and/or expression level of Not4 protein or homolog thereof of the parent fungal host cell.

67. The fungal host cell according to embodiment 66, in which the activity level and/or expression level of Not4 protein or homolog thereof is reduced to no more than 60% of the activity level and/or expression level of Not4 protein or homolog thereof of the parent fungal host cell.

68. The fungal host cell according to embodiment 67, in which the activity level and/or expression level of Not4 protein or homolog thereof is reduced to no more than 50% of the activity level and/or expression level of Not4 protein or homolog thereof of the parent fungal host cell.

69. The fungal host cell according to embodiment 68, in which the activity level and/or expression level of Not4 protein or homolog thereof is reduced to no more than 40% of the activity level and/or expression level of Not4 protein or homolog thereof of the parent fungal host cell.

70. The fungal host cell according to embodiment 69, in which the activity level and/or expression level of Not4 protein or homolog thereof is reduced to no more than 30% of the activity level and/or expression level of Not4 protein or homolog thereof of the parent fungal host cell.

71. The fungal host cell according to embodiment 70, in which the activity level and/or expression level of Not4 protein or homolog thereof is reduced to no more than 20% of the activity level and/or expression level of Not4 protein or homolog thereof of the parent fungal host cell.

72. The fungal host cell according to embodiment 71, in which the activity level and/or expression level of Not4 protein or homolog thereof is reduced to substantially 0% of the activity level and/or expression level of Not4 protein or homolog thereof of the parent fungal host cell.

73. The fungal host cell according to any of embodiments 5 to 72, in which the host cell lacks a functional NOT4 gene or homolog thereof or functional Not4 protein or homolog thereof.

74. The fungal host cell according to any of embodiments 5 to 73, in which the host cell lacks a NOT4 gene or homolog thereof or Not4 protein or homolog thereof.

75. The fungal host cell according to any of embodiments 5 to 74, in which the NOT4 gene or homolog thereof or Not4 protein or homolog thereof is mutated to alter the interaction of the Not4 protein or homolog thereof with a Nott protein or homolog thereof.

76. The fungal host cell according to any of embodiments 5 to 75 in which the Not4 protein or homolog thereof comprises a mutation at position corresponding to a position selected from 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469 or 470 of SEQ ID NO: 6.

77. The fungal host cell according to embodiment 76 in which the position is selected from a position corresponding to 429, 430, 434, or 437 of SEQ ID NO: 6.

78. The fungal host cell according to embodiment 76 or 77 in which the position is selected from a position corresponding to 463, 464 or 466 of SEQ ID NO: 6.

79. The fungal host cell according to any of embodiments 76 to 78 in which the position is selected from a position corresponding to 442, 445, 447 or 452 of SEQ ID NO: 6.

80. The fungal host cell according to any of embodiments 76 to 79 in which the mutation is a substitution, preferably to a non-conserved amino acid.

81. The fungal host cell according to any of embodiments 76 to 80 in which the mutation at a position corresponding to position 429 of SEQ ID NO: 6 is a substitution to A, C, D, E, G, H, I, K, L, M, N, P, Q, R, S, T, V, W or Y, preferably to G, A, V, L or I, more preferably to I, L or V, most preferably to I.

82. The fungal host cell according to any of embodiments 76 to 81, in which the mutation at a position corresponding to position 429 of SEQ ID NO: 6 is a substitution from an aromatic amino acid to an aliphatic amino acid.

83. The fungal host cell according to any of embodiments 76 to 82 in which the Not4 protein comprises or consists of SEQ ID NO: 8.

84. The fungal host cell according to any preceding embodiment comprising a modified NOT4 gene, for example a polynucleotide encoding SEQ ID NO: 8.

85. The fungal host cell according to any preceding embodiment in which the host cell lacks a NOT4 gene or homolog thereof or Not4 protein or homolog thereof.

86. The fungal host cell according to any preceding embodiment, in which one or more of the following chaperones is overexpressed: AHA1, CCT2, CCT3, CCT4, CCT5, CCT6, CCT7, CCT8, CNS1, CPR3, CPRE, ERO1, EUG1, FM01, HCH1, HSP10, HSP12, HSP104, HSP26, HSP30, HSP42, HSP60, HSP78, HSP82, JEM1, MDJ1, MDJ2, MPD1, MPD2, PDI1, PFD1, ABC1, APJ1, ATP11, ATP12, BTT1, CDC37, CPR7, HSC82, KAR2, LHS1, MGE1, MRS11, NOB1, ECM10, SSA1, SSA2, SSA3, SSA4, SSC1, SSE2, SIL1, SLS1, ORM1, ORM2, PERI, PTC2, PSE1, UBI4 and HAC1 or a truncated intronless HAC1, TIM9, PAM18, TCP1 or a variant thereof.

87. The fungal host cell according to any preceding embodiment in which KEX2, or a variant or fragment thereof, is expressed or overexpressed.

88. The fungal host cell according to embodiment 86 or 87 in which PDI1 or a variant thereof is overexpressed or ERO1 or a variant thereof is overexpressed.

89. The fungal host cell according to embodiment 86 or 87 in which PDI1 or a variant thereof is overexpressed and ERO1 or a variant thereof are overexpressed.

90. The fungal host cell according to embodiment 86 or 87 in which PDI1 or a variant thereof is overexpressed and KEX2 or a variant thereof is expressed or overexpressed.

91. The fungal host cell according to embodiment 86 or 87 in which ERO1 or a variant thereof is overexpressed and KEX2 or a variant thereof is expressed or overexpressed.

92. The fungal host cell according to any of embodiments 86 to 91 in which PDI1 or a variant thereof is overexpressed and ERO1 or a variant thereof is overexpressed and KEX2 or a variant thereof is expressed or overexpressed.

93. The fungal host cell according to any preceding embodiment in which the fungal host is a yeast or a filamentous fungus.

94. The fungal host cell, according to any preceding embodiment, in which the host cell is a *Saccharomyces, Candida, Hansenula, Kluyveromyces, Pichia, Saccharomyces, Schizosaccharomyces,* or *Yarrowia*.

95. The fungal host cell according to embodiment 94 in which the *Saccharomyces* is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis*, preferably *Saccharomyces cerevisiae.*

96. A culture of fungal host cells containing a polynucleotide sequence encoding a desired protein, such as a heterologous protein, characterised in that the fungal host cells have a reduced activity level and/or expression level of Gsh1 protein or homolog thereof.

97. The culture of fungal host cells according to embodiment 96, having a reduced activity level and/or expression level of Not4 protein or homolog thereof.

98. The culture of fungal host cells of embodiment 96 or 97 in which the host cells are as defined in any of embodiments 1 to 95.

99. A method for producing a desired protein, such as a heterologous protein, from a fungal host cell comprising:
   a. providing a fungal host cell according to any of embodiments 1 to 94 or a culture according to any of embodiments 96 to 98,
   b. culturing the fungal host cell or culture to produce the desired protein,
   c. optionally recovering the desired protein,
   d. optionally purifying the desired protein,
   e. optionally formulating the desired protein with a therapeutically acceptable carrier or diluent thereby to produce a therapeutic product suitable for administration to a human or an animal, and
   f. optionally providing the desired protein in unit dosage form.

100. A method for increasing the yield of a desired protein (such as a heterologous protein) comprising:
   a. providing a fungal host cell (such as a yeast or a filamentous fungus) having a modified:

1. Gsh1 protein or homolog thereof, and/or
2. level of activity (preferably reduced) of Gsh1 protein or homolog thereof, and/or
3. GSH1 gene or homolog thereof, and/or
4. level of expression (preferably reduced) of GSH1 gene or homolog thereof, such as a fungal host cell according to any of embodiments 1 to 94, and b. culturing the host cell to produce the desired protein, and
c. optionally recovering the desired protein,
d. optionally purifying the desired protein,
e. optionally formulating the desired protein with a therapeutically acceptable carrier or diluent thereby to produce a therapeutic product suitable for administration to a human or an animal, and
f. optionally providing the desired protein in unit dosage form.

101. The method according to embodiment 99 or 100 in which the culturing is in the presence of glutathione.
102. The method according to embodiment 101 in which the glutathione is present at at least 0.05 mM.
103. The method according to embodiment 102 in which the glutathione is present at from about 0.05, 0.1, 0.2, 0.3, 0.4, 0.5, 0.6, 0.7, 0.8, 0.9, 1, 2, 3, 4, 5, 10, 20, 30, 40, 50, 60, 70, 80, 90, 100, 150, 200, 250, 300, 350, 400, 450 mM to about 0.1, 0.2, 0.3, 0.4, 0.5, 0.6, 0.7, 0.8, 0.9, 1, 2, 3, 4, 5, 10, 20, 30, 40, 50, 60, 70, 80, 90, 100, 150, 200, 250, 300, 350, 400, 450, 500 mM.
104. The method according to embodiment 103 in which the glutathione is present at from about 1 to about 10 mM.
105. The method according to embodiment 104 in which the glutathione is present at from about 3 to about 7 mM.
106. The method according to embodiment 105 in which the glutathione is present at about 5 mM.
107. The method according to any of embodiments 99 to 106 in which the yield of the desired protein is at least 2% higher than the yield from a reference fungal host cell such as a fungal host cell having a wild-type Gsh1 protein, such as SEQ ID NO: 2.
108. The method according to embodiment 107 in which the yield is at least 3, 4, 5, 6, 7, 8, 9, 10, 12.5, 15, 17.5, 20, 22.5, 25, 27.5, 30, 35, 40, 45, or at least 50% higher than the yield from a reference fungal host cell.
109. The method according to embodiment 107 or 108 in which the yield of the desired protein is at least 2% higher than the yield from a reference fungal host cell such as a fungal host cell having a Gsh1 protein of SEQ ID NO: 2.
110. The method according to embodiment 109 in which the yield is at least 3, 4, 5, 6, 7, 8, 9, 10, 12.5, 15, 17.5, 20, 22.5, 25, 27.5, 30, 35, 40, 45, or at least 50% higher than the yield from a reference fungal host cell.
111. The method according to any of embodiments 99 to 110, in which the fungal host cell has a modified:
1. Not4 protein or homolog thereof, and/or
2. level of activity (preferably reduced) of Not4 protein or homolog thereof, and/or
3. NOT4 gene or homolog thereof, and/or
4. level of expression (preferably reduced) of NOT4 gene or homolog thereof such as a fungal host cell according to any of embodiments 5 to 95.
112. The method according to embodiment 111 in which the yield of the desired protein is at least 2% higher than the yield from a reference fungal host cell such as a fungal host cell having a wild-type Not4 protein, such as SEQ ID NO: 6.
113. The method according to embodiment 112 in which the yield is at least 3, 4, 5, 6, 7, 8, 9, 10, 12.5, 15, 17.5, 20, 22.5, 25, 27.5, 30, 35, 40, 45, or at least 50% higher than the yield from a reference fungal host cell such as a fungal host cell having a wild-type Not4 protein, such as SEQ ID NO: 6.
114. The method according to any of embodiments 111 to 113 in which the yield of the desired protein is at least 2% higher than the yield from a reference fungal host cell such as a fungal host cell having a Gsh1 protein of SEQ ID NO: 2.
115. The method according to embodiment 114 in which the yield is at least 3, 4, 5, 6, 7, 8, 9, 10, 12.5, 15, 17.5, 20, 22.5, 25, 27.5, 30, 35, 40, 45, or at least 50% higher than the yield from a reference fungal host cell such as a fungal host cell having Gsh1 protein of SEQ ID NO: 2.
116. The method according to any of embodiments 111 to 115 in which the yield of the desired protein is at least 2% higher than the yield from a reference fungal host cell such as a fungal host cell having Gsh1 protein of SEQ ID NO: 2 and Not4 protein of SEQ ID NO: 6.
117. The method according to embodiment 116 in which the yield of the desired protein is at least 3, 4, 5, 6, 7, 8, 9, 10, 12.5, 15, 17.5, 20, 22.5, 25, 27.5, 30, 35, 40, 45, or at least 50% higher than the yield from a reference fungal host cell such as a fungal host cell having Gsh1 protein of SEQ ID NO: 2 and Not4 protein of SEQ ID NO: 6.
118. The method according to any of embodiments 99 to 117 in which the desired protein is selected from albumin, a monoclonal antibody, an etoposide, a serum protein (such as a blood clotting factor), antistasin, a tick anticoagulant peptide, transferrin, lactoferrin, endostatin, angiostatin, collagens, immunoglobulins or immunoglobulin-based molecules or fragment of either (e.g. a Small Modular ImmunoPharmaceutical™ ("SMIP") or dAb, Fab' fragments, F(ab')2, scAb, scFv or scFv fragment), a Kunitz domain protein (such as those described in WO03/066824 (incorporated herein by reference), with or without albumin fusions), interferons, interleukins, IL-10, IL-11, IL-2, interferon α (alpha) species and sub-species, interferon β (beta) species and sub-species, interferon γ (gamma) species and sub-species, leptin, CNTF, $CNTF_{Ax15}$, IL-1-receptor antagonist, erythropoietin (EPO) and EPO mimics, thrombopoietin (TPO) and TPO mimics, prosaptide, cyanovirin-N, 5-helix, T20 peptide, T1249 peptide, HIV gp41, HIV gp120, urokinase, prourokinase, tPA, hirudin, platelet derived growth factor, parathyroid hormone, proinsulin, insulin, glucagon, glucagon-like peptides such as exendin-4, GLP-1 or GLP-2, insulin-like growth factor, calcitonin, growth hormone, transforming growth factor β (beta), tumour necrosis factor, G-CSF, GM-CSF, M-CSF, FGF, coagulation factors in both pre and active forms, including but not limited to plasminogen, fibrinogen, thrombin, pre-thrombin, pro-thrombin, von Willebrand's factor, $alpha_1$-antitrypsin, plasminogen activators, Factor VII, Factor VIII, Factor IX, Factor X and Factor XIII, nerve growth factor, LACI, platelet-derived endothelial cell growth factor (PD-ECGF), glucose oxidase, serum cholinesterase, aprotinin, amyloid precursor protein, inter-alpha trypsin inhibitor, antithrombin III, apo-lipoprotein species, Protein C, Protein S, a metabolite, an antibiotic, or a variant or fragment of any of the above.
119. The method according to any of embodiments 99 to 118 in which the desired protein comprises or consists of an albumin or variant, fragment and/or fusion thereof.
120. The method according to embodiment 119 in which the albumin or variant, fragment and/or fusion thereof has at least 70% identity to SEQ ID NO: 10.

121. The method according to embodiment 120 in which the albumin or variant, fragment and/or fusion thereof has at least 75, 80, 85, 90, 91, 92, 93, 95, 96, 97, 98 or 99% identity to SEQ ID NO: 10.

122. The method according to embodiment 121 in which the albumin or variant, fragment and/or fusion thereof has at least 70% identity to SEQ ID NO: 10, preferably at least 75, 80, 85, 90, 91, 92, 93, 95, 96, 97, 98 or 99% identity to SEQ ID NO: 10, and comprises an A, C, D, E, F, G, H, I, L, M, N, P, Q, R, S, T, V, W or Y at a position corresponding to K573 of SEQ ID NO: 10.

123. The method according to embodiment 122 in which the albumin or variant, fragment and/or fusion thereof comprises a P, H, W or Y at a position corresponding to K573 of SEQ ID NO: 10.

124. The method according to embodiment 123 in which the albumin or variant, fragment and/or fusion thereof has at least 98% identity to SEQ ID NO: 10, and comprises a P at a position corresponding to K573 of SEQ ID NO: 10.

125. The method according to any of embodiments 119 to 124 in which the fusion comprises a fusion partner which is a not albumin or a variant, fragment and/or fusion thereof.

126. The method according to any of embodiments 120 to 125 in which the fusion comprises a fusion partner selected from monoclonal antibody, an etoposide, a serum protein (such as a blood clotting factor), antistasin, a tick anticoagulant peptide, transferrin, lactoferrin, endostatin, angiostatin, collagens, immunoglobulins or immunoglobulin-based molecules or fragment of either (e.g. a Small Modular ImmunoPharmaceutical™ ("SMIP") or dAb, Fab' fragments, F(ab')2, scAb, scFv or scFv fragment), a Kunitz domain protein (such as those described in WO03/066824 (incorporated herein by reference), interferons, interleukins, IL-10, IL-11, IL-2, interferon α (alpha) species and sub-species, interferon β (beta) species and sub-species, interferon γ (gamma) species and sub-species, leptin, CNTF, $CNTF_{Ax15}$, IL-1-receptor antagonist, erythropoietin (EPO) and EPO mimics, thrombopoietin (TPO) and TPO mimics, prosaptide, cyanovirin-N, 5-helix, T20 peptide, T1249 peptide, HIV gp41, HIV gp120, urokinase, prourokinase, tPA, hirudin, platelet derived growth factor, parathyroid hormone, proinsulin, insulin, glucagon, glucagon-like peptides such as exendin-4, GLP-1 or GLP-2, insulin-like growth factor, calcitonin, growth hormone, transforming growth factor β (beta), tumour necrosis factor, G-CSF, GM-CSF, M-CSF, FGF, coagulation factors in both pre and active forms, including but not limited to plasminogen, fibrinogen, thrombin, pre-thrombin, pro-thrombin, von Willebrand's factor, $alpha_1$-antitrypsin, plasminogen activators, Factor VII, Factor VIII, Factor IX, Factor X and Factor XIII, nerve growth factor, LACI, platelet-derived endothelial cell growth factor (PD-ECGF), glucose oxidase, serum cholinesterase, aprotinin, amyloid precursor protein, inter-alpha trypsin inhibitor, antithrombin III, apo-lipoprotein species, Protein C, Protein S, a metabolite, an antibiotic, or a variant or fragment of any of the above.

127. The method according to embodiment 126 in which the fusion partner comprises or consists of a glucagon-like protein or analog thereof.

128. The method according to embodiment 127 in which the fusion partner comprises or consists of SEQ ID NO: 14, SEQ ID NO: 15, SEQ ID NO: 51, or SEQ ID NO: 52.

129. The method according to any of embodiments 118 to 128 in which the desired protein comprises or consists of SEQ ID NO: 16.

130. The method according to any of embodiments 99 to 129 in which the host cell is cultured at a scale of at least 1 L.

131. The method according to embodiment 130 in which the host cell is cultured at a scale of at least 2 L.

132. The method according to embodiment 131 in which the host cell is cultured at a scale of at least 5 L.

133. The method according to embodiment 132 in which the host cell is cultured at a scale of at least 10 L.

134. The method according to embodiment 133 in which the host cell is cultured at a scale of at least 1000 L.

135. The method according to embodiment 134 in which the host cell is cultured at a scale of at least 5000 L.

136. The method according to any of embodiments 99 to 135 in which the desired protein is secreted from the fungal host cell.

137. The method according to embodiment 136 in which the desired protein results from an immature protein comprising a signal peptide.

138. The method according to embodiment 137 in which the signal peptide comprises or consists of SEQ ID NO: 17, SEQ ID NO: 18, SEQ ID NO: 19, SEQ ID NO: 21, SEQ ID NO: 22, SEQ ID NO: 23, SEQ ID NO: 24, SEQ ID NO: 41 or SEQ ID NO: 42 or a signal peptide comprising the pentapeptide motif of SEQ ID NO: 20.

139. The method according to embodiment 138 in which the signal peptide comprises or consists of SEQ ID NO: 19.

140. The method according to embodiment 138 in which the signal peptide comprises or consists of SEQ ID NO: 24.

141. The method according to embodiment 138 in which the signal peptide comprises or consists of SEQ ID NO: 42.

142. The method according to any of embodiments 99 to 135 in which the desired protein is intracellular.

143. A desired protein (such as a heterologous protein) produced by the method according to any of embodiments 99 to 142.

144. The desired protein according to embodiment 143 for prophylaxis, therapy or diagnosis.

145. A composition, such as a pharmaceutical composition, comprising the desired protein according to embodiment 143 or 144 and a pharmaceutically acceptable carrier.

146. A method of treatment comprising administering the desired protein of embodiment 143 or 144 or the composition of embodiment 145 to a patient.

147. A method of preparing a fungal host cell according to any of embodiments 1 to 95 or a culture according to any of embodiments 96 to 98, the method comprising genetically modifying a (parent) fungal host cell to reduce the expression level and/or activity level of Gsh1 protein or homolog thereof.

148. The method according to embodiment 147, further comprising genetically modifying a (parent) fungal host cell to reduce the expression level and/or activity level of Not4 protein or homolog thereof.

149. Use of a means to reduce the expression level and/or activity level of Gsh1 protein or homolog thereof in a fungal host cell to increase the yield of a desired protein (such as a heterologous protein) from the fungal host cell, for example: by mutating or deleting the GSH1 gene, thus resulting in a mutated Gsh1 protein or homolog thereof or complete absence of Gsh1 protein or homolog thereof; by removing or changing the open reading frame of the gene; by mutating or changing control sequences of the GSH1 gene such as a promoter sequence and/or a terminator sequence; by blocking or reducing transcription of the GSH1 gene for example by introducing suitable interfering RNA such as antisense mRNA, by introducing, controlling or modifying suitable transcriptional activator genes or by introducing an agent which blocks activity level of Gsh1 protein or homolog thereof.

150. Use of a means to reduce the expression level and/or activity level of Gsh1 protein or homolog thereof and to reduce the activity level of Not4 protein or homolog thereof in a fungal host cell to increase the yield of a desired protein (such as a heterologous protein) from the fungal host cell, for example: by mutating or deleting the GSH1 gene and mutating or deleting the NOT4 gene, thus resulting in a mutated Gsh1 protein or homolog thereof or complete absence of Gsh1 protein or homolog thereof and resulting in a mutated Not4 protein or homolog thereof or complete absence of Not4 protein or homolog thereof; by removing or changing the open reading frame of the gene; by mutating or changing control sequences of the GSH1 and/or NOT4 gene such as a promoter sequence and/or a terminator sequence; by blocking or reducing transcription of the GSH1 and/or NOT4 gene for example by introducing suitable interfering RNA such as antisense mRNA; by introducing, controlling or modifying suitable transcriptional activator genes or by introducing an agent which blocks activity level of Gsh1 protein or homolog thereof and/or Not4 protein or homolog thereof.
151. A Gsh1 protein or homolog thereof, comprising at least 50% identity to SEQ ID NO: 2 and a mutation at a position corresponding to one or more positions selected from 47, 48, 49, 50, 51, 120, 121, 122, 123, 124, 125, 126, 127, 128, 129, 130, 409, 451, 452, 453, 454 and 455 of SEQ ID NO: 2.
152. The Gsh1 protein, or homolog thereof, according to embodiment 151 in which the position corresponds to R125 of SEQ ID NO: 2.
153. The Gsh1 protein, or homolog thereof, according to embodiment 151 or 152 in which the position corresponds to H409 of SEQ ID NO: 2.
154. The Gsh1 protein, or homolog thereof, according to any of embodiments 151 to 153 in which the position corresponds to P453 of SEQ ID NO: 2.
155. The Gsh1 protein, or homolog thereof, according to any of embodiments 151 to 154 in which the mutation is a substitution, preferably to a non-conserved amino acid.
156. The Gsh1 protein, or homolog thereof, according to any of embodiments 152 to 155 in which the mutation at a position corresponding to position R125 of SEQ ID NO: 2 is a substitution to A, C, D, E, F, G, H, I, L, M, N, P, Q, S, T, V, W or Y, preferably to C, D, E or G, more preferably to G.
157. The Gsh1 protein, or homolog thereof, according to any of embodiments 151 to 156 in which the mutation at a position corresponding to position R125 of SEQ ID NO: 2 is a substitution from a positively charged amino acid to an aliphatic, aromatic, hydrophobic, small, tiny, polar or negatively charged amino acid, preferably a negatively charged amino acid to a tiny amino acid.
158. The Gsh1 protein, or homolog thereof, according to any of embodiments 151 to 157 in which the mutation at a position corresponding to position D49 of SEQ ID NO: 2 is a substitution to A, C, F, G, H, I, K, L, M, N, P, Q, R, S, T, V, W or Y, preferably to H, K or R, more preferably to K or R.
159. The Gsh1 protein, or homolog thereof, according to any of embodiments 151 to 158 in which the mutation at a position corresponding to position 49 of SEQ ID NO: 2 is from a negatively charged amino acid to a positively charged amino acid.
160. The Gsh1 protein, or homolog thereof, according to any of embodiments 151 to 159 in which the mutation at a position corresponding to position H409 of SEQ ID NO: 2 is a substitution to A, C, D, E, F, G, I, K, L, M, N, P, Q, R, S, T, V, W or Y, preferably to A, I, L, V, M, F, W, Y, more preferably to A, I, L, V, most preferably to L.
161. The Gsh1 protein, or homolog thereof, according to any of embodiments 151 to 160 in which the mutation at a position corresponding to position H409 of SEQ ID NO: 2 is from an aromatic amino acid to an aliphatic amino acid.
162. The Gsh1 protein, or homolog thereof, according to any of embodiments 151 to 161 in which the mutation at a position corresponding to position P453 of SEQ ID NO: 2 is a substitution to A, C, D, E, F, G, H, I, K, L, M, N, Q, R, S, T, V, W or Y, preferably to A, I, L, V, M, F, W, Y, more preferably to A, I, L, V, most preferably to L.
163. The Gsh1 protein, or homolog thereof, according to any of embodiments 151 to 162 in which the mutation at a position corresponding to position P453 of SEQ ID NO: 2 is from an aromatic amino acid to an aliphatic amino acid.
164. The Gsh1 protein, or homolog thereof, according to any of embodiments 151 to 163 comprising or consisting of SEQ ID NO: 4.

The invention is now described with reference to the following non-limiting examples:

EXAMPLES

Example 1: Mutation of the *Saccharomyces cerevisiae* GSH1 Gene

*S. cerevisiae* DP9 has the genotype cir⁰ MATa, leu2-3, leu2-112 ubc4 ura3 yap3::URA3 lys2 hsp150:LYS2 with PDI1, URA3 and YIplac211 integrated at the PDI1 locus (Finnis et al, 2010, Microbial Cell Factories 9: 87). The inventors observed that *S. cerevisiae* DP9 (when transformed with an albumin-encoding plasmid) was able to produce recombinant human albumin at a higher yield than predecessor strains e.g. *S. cerevisiae* DB1. Characterisation of *S. cerevisiae* DP9 revealed a SNP in the GSH1 gene. To establish whether this SNP contributed to the improved protein yield of *S. cerevisiae* DP9, the SNP (A373G) was reverted to the wild-type (i.e. A at position 373) as described below. Consequently, the mutant Gsh1 protein (G125) was also reverted to wild-type (R125). The wild-type GSH1 gene and Gsh1 protein are provided in SEQ ID NO: 1 and SEQ ID NO: 2, respectively. The mutant (i.e. containing the SNP) GSH1 gene and Gsh1 protein are provided in SEQ ID NO: 3 and SEQ ID NO: 4, respectively.

The *S. cerevisiae* GSH1 gene is located on chromosome X. The SNP (A373G) in the mutant GSH1 gene was reverted to wild type by the process of integrating a fragment into the GSH1 locus, which changed base 373G to A, thus reverting the mutant Gsh1 protein (G at position 125) to wild-type Gsh1 protein (R at position 125).

This was achieved by first amplifying, by PCR, a suitable selection marker (KanMX) with DNA primers which included DNA sequences at their 5' ends, identical to regions upstream of the GSH1 open reading frame. The PCR primers were MBP267 and MBP268. KanMX confers resistance to geneticin (G418).

Primer MBP267:
(SEQ ID NO: 29)
5'-ATACTATTGTAATTCAAAAAAAAAAAGCGAATCTTCCCATGCCTGT
TGCTGCTCTTGAATGGCGACAGCCTATTGCCCCAGTGTTCCCTCAACAA
CCTTGCGTACGCTGCAGGTCG-3'

Primer MBP268:
(SEQ ID NO: 30)
5'-ACAGTTGTAGTCACGTGCGCGCCATGCTGACTAATGGCAGCCGTCG
TTGGGCAGAAGAGAATTAGTATGGTACAGGATACGCTAATTGCGCTCCA
ACTACATCGATGAATTCGAGCTCG-3'

Figure 2:
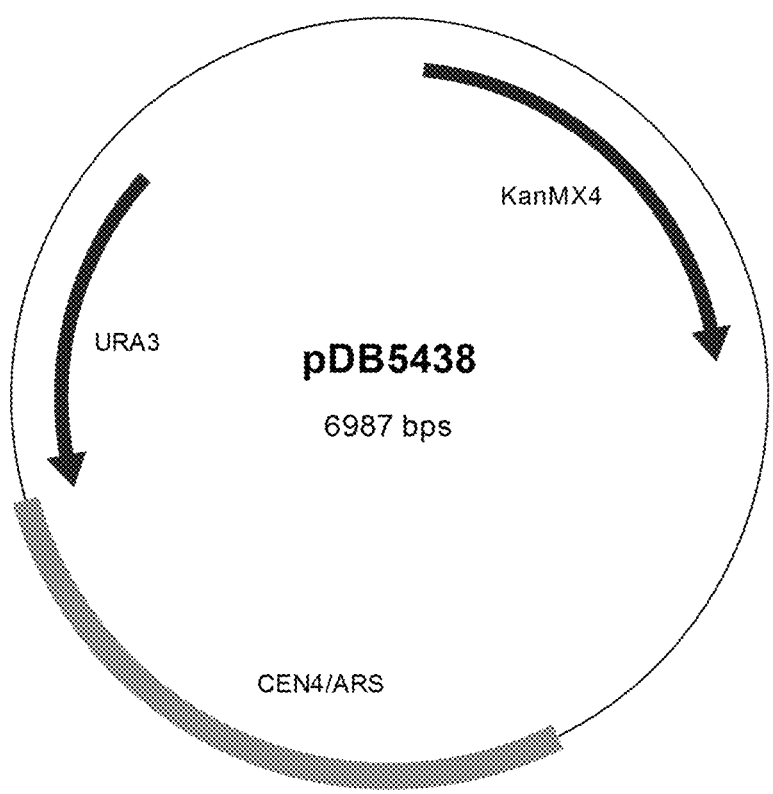
FIG. 2 shows the construction of plasmid pDB5438.

PCR was performed to amplify the KanMX gene from the plasmid pDB5438 (FIG. 2). Conditions were as follows: 100 ng plasmid pDB5438, 0.5 µM of each primer, 0.2 µM dNTPs, initial denaturation for 30 seconds at 98° C., then 35 cycles with 98° C. for 10 seconds, annealing at 62° C. for 30 seconds, extension at 72° C. for 2 minutes, followed by a final extension at 72° C. for 4 minutes, and cooling to 4° C., using an Applied Biosystems 2720 Thermal Cycler and a NEB Q5 Hot Start High-Fidelity DNA Polymerase PCR kit (M0493S), total reaction volume 50 µL, according to the manufacturer's instructions.

The product, 5'-GSH1 5'UTR-KanMX-GSH1 5'UTR-3', was analysed by gel electrophoresis and was found to be of the expected size, approximately 1.7 kb. The amplified PCR product was purified. The purified product was used to transform a *S. cerevisiae* strain which was wild-type for GSH1 (i.e SEQ ID No: 1). Transformation was done using a Sigma Yeast Transformation kit according to the manufacturer's instructions, except that after the step where the transformation mix is centrifuged, the pellet was re-suspended in 0.5 mL YEPD medium, and then transferred to a shake flask containing 4.5 mL YEPD. YEPD (g/L): 10 g Bacto™ Yeast Extract Technical, 20 g Bacto™ Peptone, 20 g Glucose.

The shake flask was incubated for 16 hours at 30° C. with shaking (200 rpm). The culture was centrifuged at 3,000 revolutions per minute (rpm) for 5 minutes and the supernatant decanted. Then the pellet was washed in 1M sorbitol and then re-suspended in 0.5 ml 1M sorbitol. About 100 µl was then plated onto freshly prepared G418 agar plates (300 µg/ml G418 final concentration) and incubated face-down at 30° C. for four days. The G418 agar plates were prepared as follows: 0.17 g yeast nitrogen base (without $(NH_4)_2SO_4$ and without amino acids), 0.1 g glutamic acid (monosodium salt, Sigma G-1626) and 0.069 g CSM-Leu powder were dissolved in 100 ml $H_2O$ (sterile water for irrigation—nonpyrogenic, hypotonic) and filter-sterilised. Then 1.5 g Bacto agar was added and the bottle was heated in a steamer for one hour and then cooled to 55° C. in a water bath. 0.6 ml 50 mg/ml Geneticin (G418) and 4 mL sterile 50% dextrose (w/v) were added and mixed. Aliquots of the mixture were poured into petri dishes to set.

Genomic DNA was extracted from G418 resistant transformants and used as a template in a second PCR, using primers MBP288 and MBP289, to amplify a 5'-GSH1 5'UTR-KanMX-GSH1 5'UTR-GSH1 ORF fragment (SEQ ID NO: 31) containing the GSH1 5'UTR with KanMX gene inserted, and the 5' part of the GSH1 ORF (up to base 422)

Primer MBP288:
(SEQ ID NO: 32)
5'-GATTTTATCGGTCAAAGG-3'

Primer MBP289:
(SEQ ID NO: 33)
5'-CTATCTTGTCTCGCATATTC-3'

Figure 3:
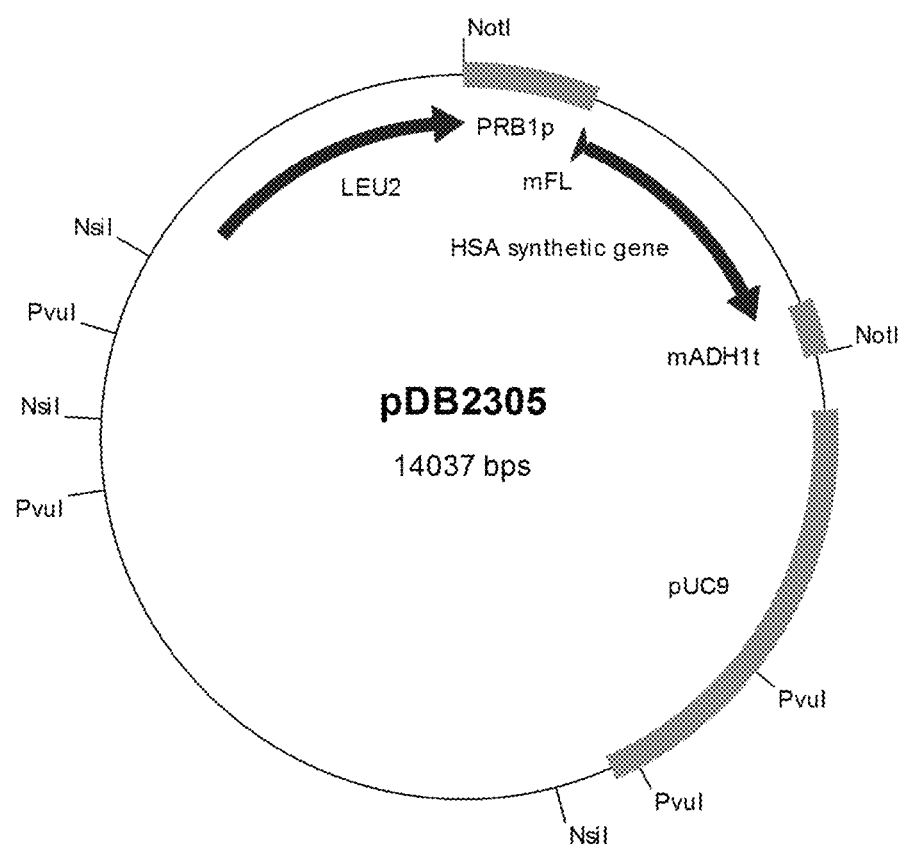
FIG. 3 shows the construction of plasmid pDB2305, "HSA" means recombinant human albumin, "mFL" is a leader sequence.

The PCR materials, method and conditions were as described above, except that 1 µl genomic DNA was used, the annealing temperature was 55° C. and the extension time was 3 minutes in each cycle and finally 7 minutes. The product was analysed by gel electrophoresis and was found to be of the expected size, approximately 2.9 kb. The amplified PCR products were purified using a QIAGEN QIAquick PCR Purification kit according to the manufacturer's instructions. The purified product was used to transform DP9 [pDB2305] (FIG. 3) using the transformation method described above. *S. cerevisiae* DP9 is a strain containing the GSH1 SNP (A373G which results in R125G). pDB2305 is a plasmid for the expression of human albumin (FIG. 3). The outgrowth and selection on G418 agar plates were as described above. Genomic DNA was extracted from resistant colonies, and PCR was used to amplify a 546 bp fragment that covered the region from 100 bp upstream of ORF to base 446 of ORF, using primers MBP290 and MBP292. The same PCR kit and conditions were used except the cycling steps were changed to an initial denaturation of 98° C. for 1 minute, followed by 35 cycles of 98° C. for 10 seconds, annealing at 61° C. for 20 seconds, and extension at 72° C. for 2.5 minutes and then a final extension at 72° C. for 7 minutes.

Primer MBP290:
(SEQ ID NO: 34)
5'-TCTCGAGTCACTTGTAGAAG-3'

Primer MBP292:
(SEQ ID NO: 35)
5'-GAGCCCACATGCAAGTT-3'

The products were cleaned using the Qiagen QIAquick 96 PCR Purification kit. A Life Technologies Big Dye Terminator v3.1 Cycle Sequencing kit was used for the sequencing of the products according to the manufacturer's instructions, using 50 µL total reaction volumes, with ~50 ng of the cleaned products as template and 4 µL of 1 µM primer MBP291. The conditions were as following: Initial denaturation 96° C. 1 minute then 25 cycles with denaturation 96° C. for 10 seconds, annealing 50° C. for 5 seconds, elongation 60° C. for 4 minutes and finally cooling to 4° C. The sequencing reactions were precipitated and resuspended in HiDi (Applied Biosystems) and analysed on an Applied Biosystems 3130xl Genetic Analyser.

Primer MBP291:
(SEQ ID NO: 36)
5'-GTAGGGTGGTTTAGAGTATC-3'

The sequencing analysis showed that one transformant had the wild type A at position 373 (R125), this strain was named PRG13 [pDB2305]. Two transformants still had the G at position 373 (G125), these strains were named PSG10 [pDB2305] and PSG11 [pDB2305]. These three transformants were cultured in a 48-well microtiter plate (MTP), containing 0.5 mL BMMD (0.17% (w/v) yeast nitrogen base without amino acid and ammonium sulphate (Difco), 37.8 mM ammonium sulphate, 36 mM citric acid, 126 mM disodium hydrogen orthophosphate pH6.5, 2% (w/v) glucose, adjusted to pH 6.5 with NaOH) in each well. The MTP was incubated at 30° C. in a humidity chamber with shaking (200 rpm) for 72 hours. Then 50 µL cell culture from each well was transferred into three wells in a new 48-well MTP containing 0.45 mL BMMD in each well. The new MTP was incubated at 30° C. in a humidity chamber with shaking (200 rpm) for 96 hours.

The supernatant was isolated by centrifugation and recombinant albumin productivity was determined by GP-HPLC analysis using a LC2010 HPLC system (Shimadzu) equipped with UV detection under Shimadzu VP7.3 client server software control. Injections of 75 µL were made onto a 7.8 mm id×300 mm length TSK G3000SWXL column (Tosoh Bioscience), with a 6.0 mm id×40 mm length TSK SW guard column (Tosoh Bioscience). Samples were chromatographed in 25 mM sodium phosphate, 100 mM sodium sulphate, 0.05% (w/v) sodium azide, pH 7.0 at 1 mL·min$^{-1}$, with a run time of 20 minutes. Samples were quantified by UV detection at 280 nm, by peak area, relative to a recombinant human albumin standard of known concentration (10 mg/mL) and corrected for their relative extinction coefficients.

As shown in Table 2, the presence of the SNP resulted in a 21% increase in average albumin yield.

TABLE 2

Albumin productivity in PRG13 [pDB2305] compared with PSG10 [pDB2305] and PSG11 [pDB2305]

|  | WT GSH1 (PRG13 [pDB2305]) | GSH1 with SNP A373G (PSG10 [pDB2305] and PSG11 [pDB2305]) |
|---|---|---|
| Albumin (relative yield) | 100% ± 3.91% | 121% ± 5.58 |

P value (t-test): 8.89E−05

Figure 4:
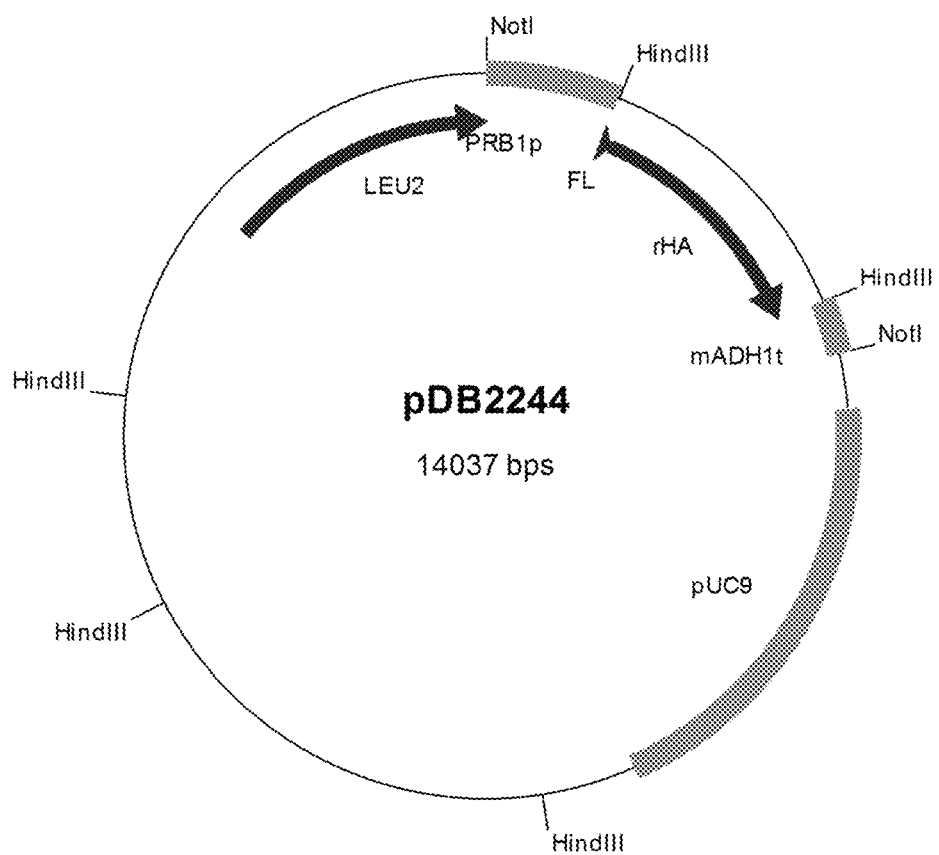
FIG. 4 shows the construction of plasmid pDB2244, "rHA" means recombinant human albumin, "FL" is a leader sequence.

The work was repeated in a further *S. cerevisiae* strain. Briefly, the same transformation procedure was performed on *S. cerevisiae* strain BXP10 [pDB2244] (FIG. 4), in order to revert the GSH1 SNP to wild-type. pDB2244 is a plasmid which expresses human albumin. the strains were grown in shake flask, approximately 10 mL of growth media in a 50 ml flask, incubated with shaking at 200 rpm at 30° C. The yield of albumin from a transformant still containing the SNP, i.e. BSG3 [pDB2244], was compared with the yield of albumin from a transformant with the SNP converted to wild-type i.e. BRG5 [pDB2244]. BXP10 has the genotype MATa, leu2-3, leu2-122, cant, prat, ubc4, ura3, yap3::URA3, lys2, hsp150::LYS2, and pmt1::URA3.

As shown by Table 3, the presence of the SNP resulted in a 68% increase in albumin yield (three replicates for each strain).

TABLE 3

Albumin productivity in BRG5 [pDB2244] and BSG3 [pDB2244]

|  | BRG5 [pDB2244] (WT GSH1) | BSG3 [pDB2244] (GSH1 with SNP A373G |
|---|---|---|
| Albumin (relative yield) | 100% ± 7.84 | 168% ± 9.45 |

P value (t-test): 0.001

Example 2: Deletion of the *S. cerevisiae* GSH1 Gene Enhanced the Production of Recombinant Protein The GSH1 gene was deleted in the same two *S. cerevisiae* strains that were used in Example 1 for SNP reversion. The deletion was achieved by replacing the GSH1 gene with the marker KanMX. Consequently, the resultant strains were unable to produce any Gsh1 protein. In order to perform the deletion, the required DNA was ordered as a plasmid insert flanked by Acc65I restriction sites. The fragment of DNA consisted of the KanMX DNA flanked on the 5' end by 300 bp immediately upstream to the GSH1 ORF and on the 3' end by 300 bp immediately downstream to the GSH1 ORF (SEQ ID NO: 43). The plasmid was digested with Acc65I and the KanMX fragment purified from a Tris-acetate-EDTA (TAE) agarose gel using the QIAGEN gel extraction kit. This DNA was used to transform yeast strains DP9 [pDB2305] and BXP10 [pDB2244], where pDB2305 and pDB2244 are plasmids containing an expression cassette for human serum albumin. At the end of the transformation procedure the yeast cells were resuspended in YEPD media and grown overnight at 30° C. and 200 rpm. The following day they were plated on G418 plates (as described in Example 1), with L-glutathione added to 5 mM. Colonies were patched onto new plates (likewise with G418 and L-glutathione) and when the patches had grown, genomic DNA was extracted and PCRs performed using primers which would flank the junctions if the whole DNA fragment had integrated correctly. Three transformants were identified where GSH1 had been deleted in BXP10 (the transformants were named BDG1, BDG2 and BDG10) and one transformant where GSH1 had been deleted in DP9 (the transformant was named PDG14). These strains, together with the previously described strain with or without the SNP reversion, were cultured in 48 well plates in BMMD. The deletion strains were grown in wells supplemented with 5 mM L-glutathione and the other strains were cultured both with and without the L-glutathione. The supernatants were assayed by GP-HPLC to quantitate the expression levels of human serum albumin.

TABLE 4

Albumin productivity in BXP10-derived strains: BRG5 [pDB2244] (WT GSH1), BSG3 [pDB2244] (SNP) and BDG1 [pDB2244], BDG2 [pDB2244] and BDG10 [pDB2244] (ΔGSH1)

|  | Without L-glutathione | | | With L-glutathione | | |
|---|---|---|---|---|---|---|
|  | A | B | C | D | E | F |
|  | BRG5 [pDB2244] (WT GSH1) | BSG3 [pDB2244] (GSH1 with SNP) | BDG1 [pDB2244], BDG2 [pDB2244] and BDG10 [pDB2244] (all ΔGSH1) | BRG5 [pDB2244] (WT GSH1) | BSG3 [pDB2244] (GSH1 with SNP) | BDG1 [pDB2244], BDG2 [pDB2244] and BDG10 [pDB2244] (all ΔGSH1) |
| Strain(s) |  |  |  |  |  |  |
| Albumin (relative yield) | 100% ± 1.47 | 132% ± 5.70 | (not tested) | 100% ± 6.67 | 127% ± 6.84 | 137% ± 9.74 |

(1 standard deviation)
P value (t-test) deletion (grown with L-glutathione) compared to WT (grown without L-glutathione): 1.25E−08 (see Table 4, columns F and A)
P value (t-test) deletion compared to WT (both grown with L-glutathione): 8.90E−05 (see table 4, columns F and D)

As shown in Table 4, deletion of GSH1 in BXP10 [pDB2244], resulted in an increase in albumin yield when compared to the strain with wild-type GSH1. In addition, as has also been shown in Example 1, the presence of the SNP in GSH1 increased albumin yield when compared with the strain containing wild-type GSH1.

TABLE 5

Albumin productivity in DP9-derived strains: PRG13 [pDB2305] (WT GSH1), PSG10 [pDB2305] (GSH1 with SNP A373G) and PDG14 [pDB2305] (ΔGSH1)

|  | Without L-glutathione | | | With L-glutathione | | |
| --- | --- | --- | --- | --- | --- | --- |
|  | A<br>PRG13<br>[PDB2305]<br>(WT<br>GSH1) | B<br>PSG10<br>[PDB2305]<br>(GSH1<br>with SNP) | C<br>PDG14<br>[PDB2305]<br>(ΔGSH1) | D<br>PRG13<br>[PDB2305]<br>(WT<br>GSH1) | E<br>PSG10<br>[PDB2305]<br>(GSH1<br>with SNP) | F<br>PDG14<br>[PDB2305]<br>(ΔGSH1) |
| Albumin (relative yield) | 100% ± 5.30% | 130% ± 6.49% | 160% ± 8.63% | 100% ± 2.92% | 134% ± 5.47% | 160% ± 6.14% |

(1 standard deviation)
P value (t-test) deletion (grown with L-glutathione) compared to WT (grown without L-glutathione): 8.45895E−09 (see Table 5, columns F and A)
P value (t-test) deletion compared to WT (both grown with L-glutathione): 1.02983E−05 (see Table 5, columns F and D)

As shown in Table 5, deletion of GSH1 in DP9 [pDB2305], resulted in an increase in albumin yield when compared to the strain with the wild-type GSH1, and when compared with the strain with the GSH1 with SNP.

Example 3: Mutation of the GSH1 Gene Improves Albumin Fermentation Yield at 10 L Scale The BXP10 derived strains from Example 1 were grown at 10 liter scale in fermenters and the rate of specific cellular productivity ($Y_{PXT}$) yield was measured (Table 6). The fermentations were carried out in a manner similar to that described for Example 5.

TABLE 6

Albumin productivity in 10 liter fermentations in BXP10 derived strains

|  | BRG5 [pDB2244]<br>(WT GSH1) | BSG3 [pDB2244]<br>(GSH1 with SNP A373G) |
| --- | --- | --- |
| Albumin (relative yield, $Y_{PXT}$) (n = 6) | 100 | 104.61 |

An average increase of 4.6% was observed in the strain having GSH1 containing the SNP A373G (resulting in R125G), this was statistically significant. P-value=0.069

Example 4: The Positive Effect on Yield of Recombinant Protein from *S. cerevisiae* Provided by a Mutation in GSH1 is Further Enhanced by the Presence of a Mutation in NOT4

Previously (PCT/US2016/068239, incorporated herein by reference), it was identified that mutation of NOT4 (also known as MOT2) results in an increased yield of heterologous protein produced in a host strain.

In order to determine whether or not combining a mutation in NOT4 with a mutation in GSH1 further affects yield, one, both or neither mutations were complemented in host cells (by transformation with a plasmid containing a wild-type version of neither, one or both of the genes) resulting in a series of strains having phenotypes that approximate to:
(A) GSH1 containing SNP, and NOT4 containing SNP,
(B) GSH1 containing SNP, and wild-type NOT4,
(C) wild-type GSH1 and NOT4 containing SNP, and
(D) wild-type GSH1 and wild-type NOT4.

Heterologous protein yields were measured by GP-HPLC analysis of the supernatants of the cultures of the resulting strains.

Figure 5:
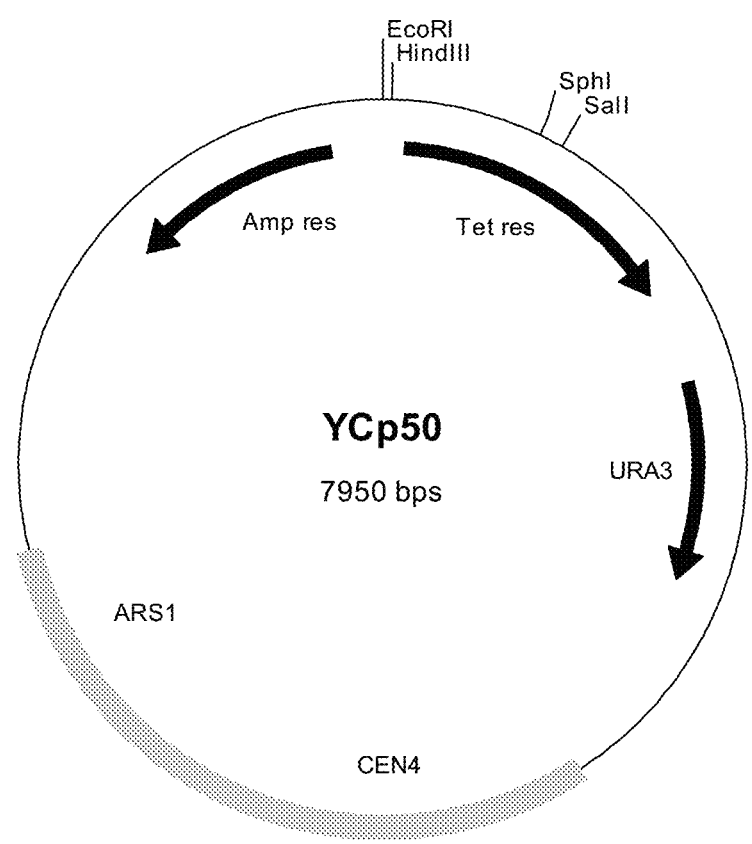
FIG. 5 shows the construction of plasmid YCp50.
Figure 6:
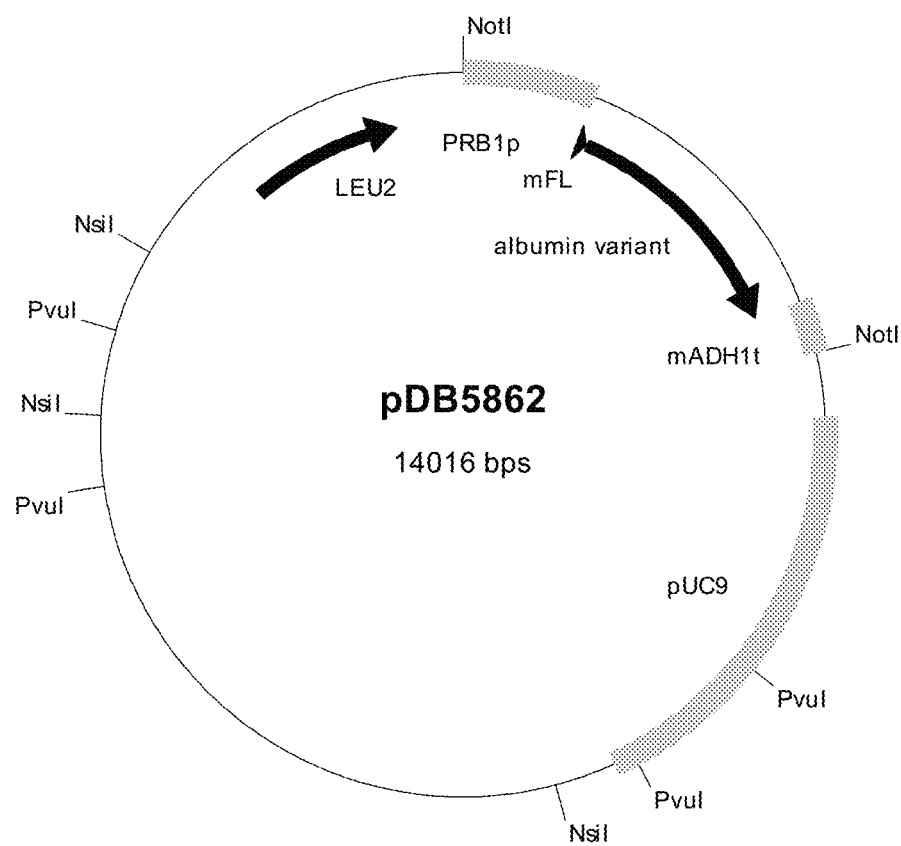
FIG. 6 shows the construction of plasmid pDB5862. "Albumin variant" is nucleic acid encoding SEQ ID NO: 45. "mFL" is a leader sequence.

To generate plasmids containing wild-type NOT4 and/or GSH1, PCRs were carried out with genomic DNA from yeast strain DB1. This strain has wild-type NOT4 and wild-type GSH1. Primer pairs (Table 7) were used to produce DNA containing the wild-type ORFs and upstream and downstream sequences of NOT4 and GSH1. The primers were designed to include restriction enzyme sites to allow cloning into the plasmid YCP50 (FIG. 5. and Rose et al., 1987, Gene, 60, 237-243). The PCRs were performed according to Table 8.

TABLE 7

PCR Primers

| Primer name | Sequence<br>(Underlined bases = restriction site) | Restriction site | SEQ ID NO: |
| --- | --- | --- | --- |
| MBP393 | 5'-TATTAT<u>GAATTC</u>AAATGTTGAGCCCGAAGACG-3' | EcoRI | 37 |
| MBP396 | 5'-TATTAT<u>AAGCTT</u>AAATTAGCGAAGCAGGTTCC-3' | HindIII | 38 |
| MBP397 | 5'-TATTAT<u>GCATGC</u>CACGTATTCTTGTGCACACG-3' | SphI | 39 |
| MBP406 | 5'-TATTAT<u>GTCGAC</u>TACCACCTACACCAATAAGC-3' | SalI | 40 |

TABLE 8

PCR conditions

| Target gene | Primers | Annealing temperature | Genomic region amplified by PCR |
|---|---|---|---|
| NOT4 | MBP393 + MBP396 | 64° C. | 385 bp upstream of ORF to 309 bp downstream |
| GSH1 | MBP397 + MBP406 | 62° C. | 596 bp upstream of ORF to 680 bp downstream |

The PCR conditions were as follows: 0.1 µg genomic DNA, 0.5 µM of each primer, 0.2 µM dNTPs, initial denaturation for 30 seconds at 98° C., then 35 cycles with 98° C. for 10 seconds, annealing at above temperature for 30 seconds, extension at 72° C. for 2 minutes, followed by a final extension at 72° C. for 4 minutes, and cooling to 4° C., using an Applied Biosystems 2720 Thermal Cycler and a NEB Q5 Hot Start High-Fidelity DNA Polymerase PCR kit (M0493S), total reaction volume 50 µL, according to the manufacturer's instructions. The products were analysed by gel electrophoresis and were found to be of the expected sizes, approximately 2.5 kb for NOT4 and approximately 3.3 kb for GSH1. The amplified PCR products were purified using a QIAGEN QIAquick PCR Purification kit according to the manufacturer's instructions.

Restriction enzyme digests were performed on the purified PCR products and on YCP50 plasmid. The restriction enzymes and buffers were from New England Biolabs (NEB) and the manufacturer's protocols were followed. The digests performed were: EcoRI+HindIII on the NOT4 PCR product, EcoRI+HindIII on YCP50, SphI+SalI on the GSH1 PCR product and SphI and SalI on YCP50. The buffer used was CutSmart buffer and the restriction enzymes were all the NEB High Fidelity ("HF") enzymes (i.e. EcoRI-HF etc). The digests were incubated for about 1.5 hours at 37° C. The digests of PCR products were purified by QIAGEN QIAquick PCR Purification kit and the YCP50 DNA was purified from a TAE agarose gel, using the QIAGEN QIAquick gel extraction kit, according to the manufacturer's instructions.

Each of the digested and purified PCR products was ligated to the YCP50 DNA which had been cut with the same enzymes. The ligations were performed using the NEB Quick ligation kit (M2200S) according to the manufacturer's instructions and using a molar ratio of 3:1 for PCR product:YCP50. One microliter of each ligation reaction was then used to transform NEB 5-alpha competent (high efficiency) *E. coli* cells (M29871) according to the manufacturer's instructions and the cells were plated onto LB ampicillin. Overnight cultures were grown from resulting colonies and QIAGEN QIAprep spin minipreps were performed. Restriction enzyme digests were performed to identify plasmids in which the cloning appeared to have been successful.

The YCP50-NOT4 plasmid was then digested with SphI+ SalI and the DNA purified from a TAE agarose gel, using the QIAGEN QIAquick gel extraction kit, according to the manufacturer's instructions. This DNA was ligated to GSH1 PCR product which had been digested with SphI+SalI and then purified using the QIAquick PCR purification kit. Again, the molar DNA ratio of insert to backbone was 3:1. NEB 5-alpha competent (high efficiency) cells were transformed (as above) and plasmid DNA prepared (as above). Correct plasmids were identified by restriction digests.

This resulted in three new plasmids: YCP50-NOT4, YCP50-GSH1 and YCP50-NOT4-GSH1. These, and YCP50 alone, were used to transform DYB7 ura3 [pDB2305] which contains plasmid pDB2305 for the expression of recombinant human serum albumin. DYB7 is described in Payne et al, (2008) Applied and Environmental Microbiology 74 (24) 7759-7766. The transformations were done using a Sigma Yeast Transformation kit according to the manufacturer's instructions, except after the step where the transformation mix is centrifuged, the pellet was re-suspended in 200 µl 1M sorbitol and then 100 µl was plated onto BMMD agar plates. The plates were incubated at 30° C. until colonies appeared.

Single colonies from each transformation were inoculated into wells of a 48 well microtiter plate, containing 0.5 ml BMMD per well. The plate was incubated at 30° C. and 200 rpm for 2 days and then an equal volume of 40% trehalose was mixed into each well and the plate stored at −80° C. At a later date, the plate was thawed and 50 µl transferred from each well to a well of a new plate containing 450 µl BMMD. This plate was incubated for 2 days at 30° C. and 200 rpm and then sub-cultured into another new plate (50 µl into 450 µl BMMD). This plate was incubated for 4 days. The plate was then centrifuged at 2000 rpm for 5 minutes and 200 µl supernatant from each was transferred to HPLC vials. The amounts of human serum albumin in the supernatants were quantitated by GP-HPLC as described in Example 1.

The new plasmids, YCP50-NOT4, YCP50-GSH1 and YCP50-NOT4-GSH1, were sequenced to confirm that they each contained the correct inserts. The sequencing was performed as described in the above examples, except that in this case 150 to 300 ng plasmid DNA was used for each reaction The relative albumin yields, measured by GP-HPLC analysis of culture supernatants, are shown in Table 9 (below).

TABLE 9

Albumin productivity in strains approximating to phenotypes containing combinations of GSH1 (SNP or wild-type) and NOT4 (SNP or wild-type)

| | Plasmids used for complementation | | | |
|---|---|---|---|---|
| | A YCP50 | B YCP50-NOT4 | C YCP50-GSH1 | D YCP50-NOT4-GSH1 |
| Resultant GSH1 status | SNP | SNP | WT* | WT* |
| Resultant NOT4 status | SNP | WT* | SNP | WT* |
| Albumin yield (relative) | 184% ± 4.88 | 177% ± 4.45 | 131% ± 4.59 | 100% ± 4.88 |
| P value (t test) compared to A | — | 1.10E-03 | 4.20E-17 | 1.87E-20 |

*Note that due to the method of construction of the strains analyzed in Table 9, the strains that contained a WT copy of the genes encoding GSH1 or NOT4 also contained the SNP versions (i.e. encoding Gsh1 R125G and Not4 F429I). The WT versions were on the plasmid and the SNP containing genes were in the genome. Due to complementation, the resultant phenotype approximates that of WT.

The yields are shown relative to (D), the strain in which there was complementation of both of the SNP-containing genes. It was seen that the NOT4 with SNP (C), resulted in a 31% increase in yield, the GSH1 with SNP (B) resulted in 77% increase in yield and the presence of both SNPs (A), resulted in 84% increase in yield. These complementation studies demonstrate that the GSH1 and NOT4 mutations positively affect albumin yield, and that when combined the yield is even further increased.

It is expected that such an increase in yield would also be observed at larger scale. This is because, Examples 1 and 2 demonstrate that mutation or deletion of GSH1 affects the yield of albumin produced from *S. cerevisiae* at small scale, Examples 3 and 5 demonstrate that this is also observed at 10 L scale and previous application PCT/US2016/068239 demonstrated that mutation or deletion of NOT4 affects the yield of albumin produced from *S. cerevisiae* at both small and 10 L scale.

Example 5: Mutation of the *S. cerevisiae* GSH1 Gene Enhanced Albumin Yield at 10 L Scale The productivity of *S. cerevisiae* strains DYB7 ura3 [pDB2305/YCp50-NOT4], DYB7 ura3 [pDB2305/YCp50-GSH1] and DYB7 ura3 [pDB2305/YCp50-NOT4-GSH1] for recombinant protein expression were assessed by growth in 10 L fermenter (Wigley et al, (2007) Genetic Engineering News. 27 (2): 40-42). The fermentation was as described in Example 1 of WO97/33973 (incorporated herein by reference) using MW11D medium, except that Wonderware Supervisory Control and Data Acquisition software was used instead of MFCS, prior to use the fermenter vessel was also subjected to a citric acid wash, the trace element stock comprised $Na_2MoO_4.2H_2O$ instead of $Na_2MoO_4.5H_2O$, the pH was adjusted to pH 6.2 with ammonia solution, initial introduction of sterile air into the vessel was at about 1.0 vvm (i.e. 1.0 liter) instead of 0.5 vvm, during the fermentation the airflow was increased in one step instead of two to maintain an airflow of approximately 1.0 vvm, the specific growth rate was approximately 0.06 $h^{-1}$ and the exponential constant (K) was kept at 0.06. "vvm" means gas volume flow per unit of liquid volume per minute.

The relative yields are shown (grams of product per liter) in Table 10.

TABLE 10

Productivity of albumin at 10 liter scale from DYB7 [pDB2305/YCp50-NOT4] and DYB7 [pDB2305/YCp50-NOT4-GSH1]

| Strain | GSH1 status | NOT4 status | % g/L |
|---|---|---|---|
| DYB7 ura3 [pDB2305/YCp50-NOT4-GSH1] | WT | WT | 100 |
| DYB7 ura3 [pDB2305/YCp50-NOT4] | SNP A373G | WT | 112 |

The yield of albumin is increased in a strain that has GSH1 containing a SNP compared with that of a strain that has a GSH1 phenotype that approximates wild-type.

Example 6: Mutation or Deletion of the *Saccharomyces cerevisiae* GSH1 Gene Enhanced the Expression of an Albumin Variant and Deletion of GSH1 Enhanced the Expression of an Albumin Fusion Protein (Albumin-IL-1 Ra) and scFv (vHvL)-FLAG The proteins being expressed in this example were (a) an albumin variant (SEQ ID NO: 45) containing 4 mutations relative to WT HSA (SEQ ID NO: 10), (b) IL-1 Ra genetically fused to the C-terminal of human serum albumin (SEQ ID NO: 47, "albumin-IL-1 Ra") and (c) the scFv, FITC8 (Evans et al 2010, Protein Expression and Purification 73:113-124, including references 16 and 17, all incorporated herein by reference) with a FLAG tag (DYKDDDDK, SEQ ID NO: 50) at its C-terminal (SEQ ID NO: 49).

Figure 7:
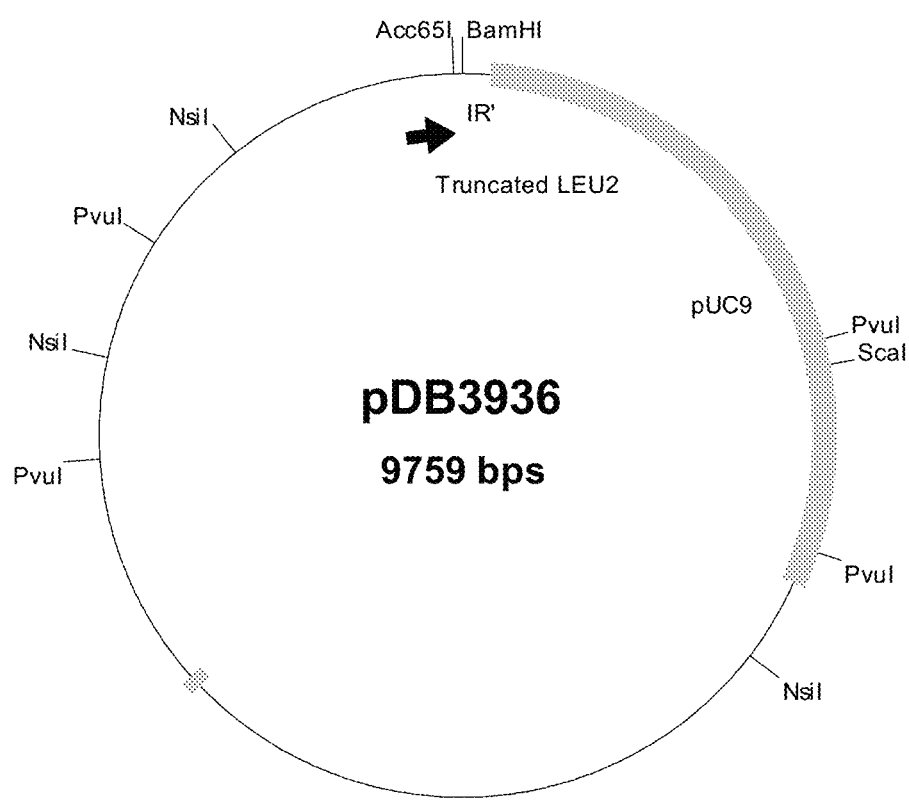
FIG. 7 shows the construction of plasmid pDB3936.
Figure 8:
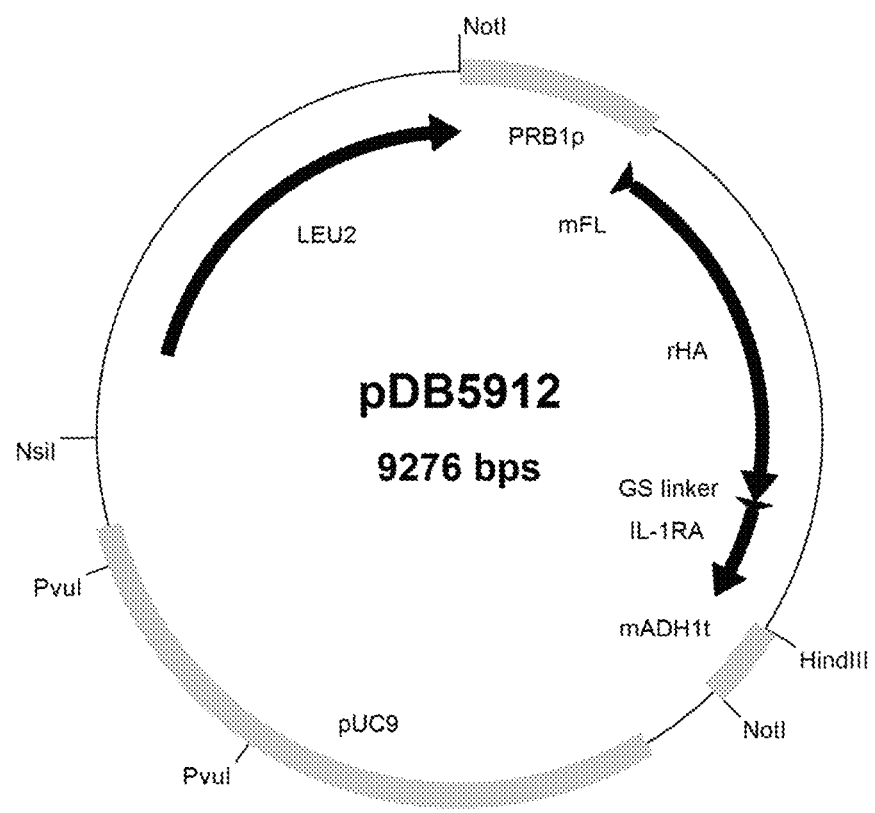
FIG. 8 shows the construction of plasmid pDB5912. "mFL" is a leader sequence.

In preparation for expression of albumin-IL-1 Ra, plasmid pDB3936 (FIG. 7) was cut with restriction enzymes Acc65I and BamHI and plasmid pDB5912 (containing an albumin-IL-1Ra expression cassette) was cut with enzymes NsiI and PvuI. A plasmid map for pDB5912 is provided in FIG. 8, the DNA sequence encoding albumin-IL-1Ra is shown in SEQ ID NO: 46. The restriction enzymes and buffers were from New England Biolabs. Both plasmid digests were purified using a Qiagen PCR purification kit following the manufacturer's instructions.

Figure 9:
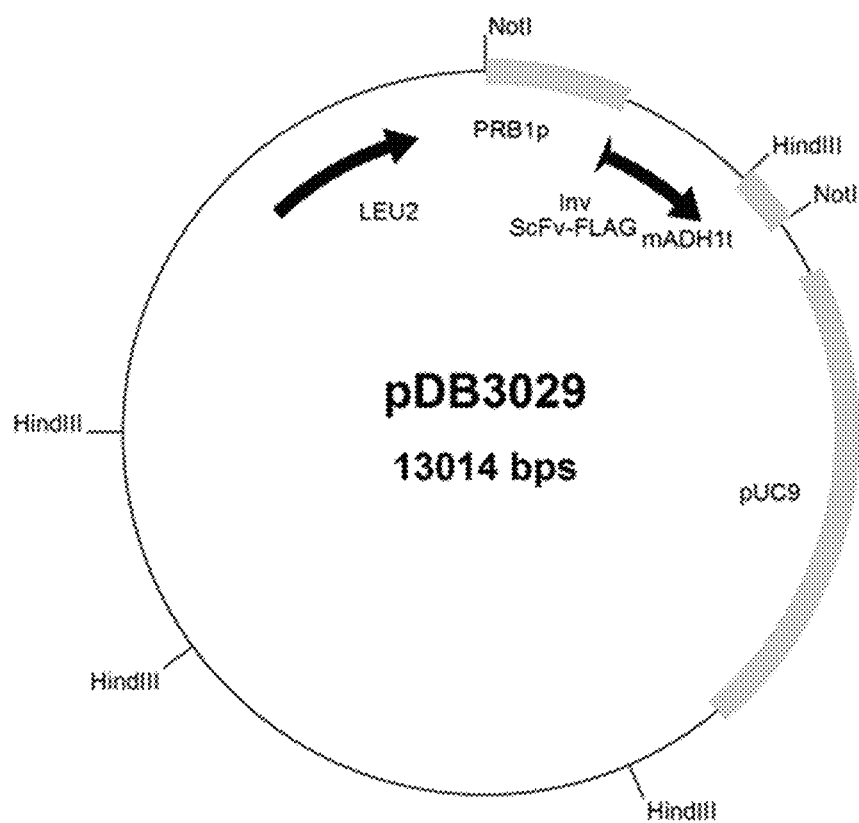
FIG. 9 shows the construction of plasmid pDB3029. "Inv" is a leader sequence.

The 3 strains, PDG14 [pDB2305], PSG11 [pDB2305] and PRG13 [pDB2305], were cultured in shake flasks in YEPD media and sub-cultured 3 times in order to cure them of the plasmid (pDB2305). Dilutions of the final cultures were plated onto YEPD and then single colonies from these plates were patched onto YEPD. The YEPD patches were transferred to BMMD+5 mM L-glutathione plates and incubated at 30° C.; a lack of growth on BMMD+5 mM L-glutathione identified the cells which had been cured of plasmid. The cured yeast strains were each transformed, using the Sigma Yeast Transformation kit according to the manufacturer's instructions, with plasmid pDB5862 (for expression of the albumin variant) (a plasmid map for pDB5862 is provided in FIG. 9, the DNA sequence encoding the albumin variant is shown in SEQ ID NO. 44), pDB3029 (for expression of scFv (vHvL)-FLAG) (a plasmid map for pDB3029 is provided in FIG. 9, the DNA sequence encoding scFv-FLAG is shown in SEQ ID NO: 48), or with the purified restriction digests of pDB3936 and pDB5912 (for expression of albumin-IL-1 RA from the gap-repaired plasmid pDB3936:GR: pDB5912). The cells were plated onto BMMD and incubated for 5 days at 30° C. Six transformants of each strain were cultured in a 48 well MTP containing 0.5 ml BMMD with 5 mM L-glutathione per well. The plate was incubated for 48 hours at 30° C. and 200 rpm in a humidity chamber. This plate was then sub-cultured by transferring 50 μl of each culture into 450 μl BMMD with 5 mM L-glutathione in a new plate. This plate was incubated for 96 hours.

The supernatant was isolated by centrifugation and recombinant protein productivity (for albumin variant, albumin-IL-1Ra or ScFv) was determined by GP-HPLC, as in Example 1.

As shown in Table 11, the presence of the SNP (A373G) or deletion, resulted in an increase in yield of albumin variant. The yield was 15% higher in the strain containing the SNP in GSH1 (PSG11) and 23% higher in the strain containing the deletion of GSH1 (PDG14), compared to the strain with wild-type GSH1 (PRG13).

TABLE 11

Albumin variant productivity in PRG13 [pDB5862], PSG11 [pDB5862] and PDG14 [pDB5862]

| | PRG13 [pDB5862] | PSG11 [pDB5862] | PPDG14 [pDB5862] |
|---|---|---|---|
| Albumin variant (relative yield) | 100% ± 19.74 | 115% ± 18.63 | 123% ± 20.34 |

P value (t-test) for SNP vs WT GSH1: P = 0.052
P value (t-test) for deletion vs WT GSH1: P = 0.011

As shown in Table 12, the presence of the deletion resulted in an increase in yield of albumin-IL-1Ra. The yield was 14% higher in the strain containing the deletion (PDG14), compared to the strain with wild-type GSH1 (PRG13).

TABLE 12

Albumin-IL-1Ra productivity in PRG13 [pDB3936:GR:pDB5912], PSG11 [pDB3936:GR:pDB5912] and PDG14 [pDB3936:GR:pDB5912]

| | PRG13 [pDB3936:GR:pDB5912] | PSG11 [pDB3936:GR:pDB5912] | PPDG14 [pDB3936:GR:pDB5912] |
|---|---|---|---|
| Albumin-IL-1Ra (relative yield) | 100% ± 20.69 | 88% ± 15.75 | 114 ± 17.37 |

P value (t-test) for SNP vs WT GSH1: P = 0.11
P value (t-test) for deletion vs WT GSH1: P = 0.049

As shown in Table 13, the presence of the deletion resulted in an increase in yield of ScFv-FLAG. The yield 38% higher in the strain containing the deletion of GSH1 (PDG14), compared to the strain with wild-type GSH1 (PRG13).

TABLE 13

ScFv (vHvL)-FLAG productivity in PRG13 [pDB3029], PSG11 [pDB3029] and PDG14 [pDB3029]

| | PRG13 [pDB3029] | PSG11 [pDB3029] | PDG14 [pDB3029] |
|---|---|---|---|
| ScFv (relative yield) | 100% ± 19.40 | 108% ± 19.77 | 138% ± 22.32 |

P value (t-test) for SNP vs WT GSH1: P = 0.33
P value (t-test) for deletion vs WT GSH1: P = 0.0009

---

The invention claimed is:

1. A method for producing a heterologous protein comprising:
 a. providing a fungal host cell having:
  1) a modified Gsh1 protein which has a reduced level of activity relative to the activity of a wild-type Gsh1 protein of an otherwise identical reference fungal host cell, and/or
  2) a reduced level of activity of Gsh1 protein relative to the activity of a wild-type Gsh1 protein of an otherwise identical reference fungal host cell, and/or
  3) a modified GSH1 gene which has a reduced level of activity relative to the activity of a wild-type GSH1 gene of an otherwise identical reference fungal host cell, and/or
  4) a reduced level of expression of GSH1 gene relative to the level of expression of a wild-type GSH1 gene of an otherwise identical reference fungal host cell, and
 b. culturing the host cell to produce the heterologous protein,
 wherein
  (i) the heterologous protein is a plant or animal protein, and/or
  (ii) the culturing is at a scale of at least 1 liter, and/or
  (iii) the method further comprises purifying the heterologous protein, and/or
  (iv) the method further comprises formulating the heterologous protein with a therapeutically acceptable carrier or diluent thereby to produce a therapeutic product suitable for administration to a human or an animal.

2. The method according to claim 1 for increasing the yield of the heterologous protein.

3. The method according to claim 1, wherein the fungal host cell is a yeast or a filamentous fungus.

4. The method according to claim 1, wherein the Gsh1 protein comprises a mutation at position corresponding to a position selected from 47, 48, 49, 50, 51, 120, 121, 122, 123, 124, 125, 126, 127, 128, 129, 130, 409, 451, 452, 453, 454 and 455 of SEQ ID NO: 2.

5. The method according to claim 4, wherein the mutation at a position corresponding to position 125 of SEQ ID NO: 2 is a substitution to C, D, E or G.

6. The method according to claim 1, wherein the Gsh1 protein comprises or consists of SEQ ID NO: 4.

7. The method according to claim 1, wherein the host cell lacks a GSH1 gene or Gsh1 protein.

8. The method according to claim 1, wherein the yield of the heterologous protein is at least 2% higher than the yield from a reference fungal host cell.

9. The method according to claim 1, wherein the reference fungal host cell has the Gsh1 protein of SEQ ID NO: 2.

10. The method according to claim 1, wherein the fungal host cell has a modified:
 1) Not4 protein, and/or
 2) level of activity of Not4 protein, and/or
 3) NOT4 gene, and/or
 4) level of expression of NOT4 gene.

11. The method according to claim 10, wherein the level of activity of the Not4 protein and/or the level of expression of the NOT4 gene is reduced.

12. The method according to claim 10, wherein the Not4 protein comprises a mutation at position corresponding to a position selected from 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469 or 470 of SEQ ID NO: 6.

13. The method according to claim 12, wherein the mutation at a position corresponding to position 429 of SEQ ID NO: 6 is a substitution to G, A, V, L or I.

14. The method according to claim 10, wherein the Not4 protein comprises or consists of SEQ ID NO: 8.

15. The method according to claim 10, wherein the host cell lacks a NOT4 gene or Not4 protein.

16. The method according to claim 10, wherein the yield of the heterologous protein is at least 2% higher than the yield from a reference fungal host cell having a wild-type Not4 protein.

17. The method according to claim 16, wherein the reference fungal host cell has a Not4 protein of SEQ ID NO: 6.

18. The method according to claim 10, wherein the yield of the heterologous protein is at least 2% higher than the yield from a reference fungal host cell having Gsh1 protein of SEQ ID NO: 2.

19. The method according to claim 1, wherein the yield of the heterologous protein is at least 2% higher than the yield from a reference fungal host cell having wild-type Gsh1 protein and wild-type Not4 protein.

20. The method according to claim 19 in which the reference fungal host cell has Gsh1 protein of SEQ ID NO: 2 and Not4 protein of SEQ ID NO: 6.

21. The method according to claim 1, wherein the heterologous protein comprises or consists of an albumin or variant, fragment and/or fusion thereof.

22. The method according to claim 1, wherein the host cell is cultured at a scale of at least 5L.

23. The method according to claim 1, further comprising recovering and/or purifying the heterologous protein.

24. The method according to claim 1, further comprising providing the heterologous protein in unit dosage form.

* * * * *

UNITED STATES PATENT AND TRADEMARK OFFICE
CERTIFICATE OF CORRECTION

PATENT NO. : 11,396,670 B2
APPLICATION NO. : 17/464991
DATED : July 26, 2022
INVENTOR(S) : Christopher John Arthur Finnis et al.

It is certified that error appears in the above-identified patent and that said Letters Patent is hereby corrected as shown below:

In the Specification

At Column 16, Line 52, replace "Nott" with --Not1--;

At Column 16, Line 60, replace "Nott" with --Not1--;

At Column 16, Line 61, replace "Nott" with --Not1--;

At Column 17, Line 54, replace "F4291" with --F429l--;

At Column 28, Line 16, replace "CPRE" with --CPR6--;

At Column 28, Line 16, replace "FM01" with --FMO1--;

At Column 28, Line 22, replace "PERI" with --PER1--;

At Column 33, Line 8, replace "0.03 Oil" with --0.03 g·L$^{-1}$--;

At Column 33, Line 8, replace "0.05 Oil" with --0.05 g·L$^{-1}$--;

At Column 33, Line 11, replace "0.8 Oil" with --0.8 g·L$^{-1}$--;

At Column 43, Line 19, replace "Nott" with --Not1--;

At Column 43, Line 63, replace "CPRE" with --CPR6--;

At Column 43, Line 63, replace "FM01" with --FMO1--;

At Column 43, Line 63, replace "FM01" with --FMO1--;

Signed and Sealed this
Tenth Day of January, 2023

Katherine Kelly Vidal
*Director of the United States Patent and Trademark Office*

At Column 44, Line 2, replace "PERI" with --PER1--;

At Column 53, Line 27, replace "cant, prat" with --can1, pra1--.

SEQUENCE LISTING

<160> NUMBER OF SEQ ID NOS: 52

<210> SEQ ID NO 1
<211> LENGTH: 2037
<212> TYPE: DNA
<213> ORGANISM: Saccharomyces cerevisiae

<400> SEQUENCE: 1

```
atgggactct tagctttggg cacgcctttg cagtggtttg agtctaggac gtacaatgaa      60
cacataaggg atgaaggtat cgagcagttg ttgtatattt tccaagctgc tggtaaaaga     120
gacaatgacc ctcttttttg gggagacgag cttgagtaca tggttgtaga ttttgatgat     180
aaggagagaa attctatgct cgacgtttgc catgacaaga tactcactga gcttaatatg     240
gaggattcgt ccctttgtga ggctaacgat gtgagttttc accctgagta tggccggtat     300
atgttagagg caacaccagc ttctccatat ttgaattacg tgggtagtta cgttgaggtt     360
aacatgcaaa aaagacgtgc cattgcagaa tataagctat ctgaatatgc gagacaagat     420
agtaaaaata acttgcatgt gggctccagg tctgtccctt tgacgctgac tgtcttcccg     480
aggatgggat gccccgactt tattaacatt aaggatccgt ggaatcataa aaatgccgct     540
tccaggtctc tgtttttacc cgatgaagtc attaacagac atgtcaggtt tcctaacttg     600
acagcatcca tcaggaccag gcgtggtgaa aaagtttgca tgaatgttcc catgtataaa     660
gatatagcta ctccagaaac ggatgactcc atctacgatc gagattggtt tttaccagaa     720
gacaaagagg cgaaactggc ttccaaaccg ggtttcattt atatggattc catgggtttt     780
ggcatgggct gttcgtgctt acaagtgacc tttcaggcac ccaatatcaa caaggcacgt     840
tacctgtacg atgcattagt gaattttgca cctataatgc tagccttctc tgccgctgcg     900
```

-continued

```
cctgctttta aaggttggct agccgaccaa gatgttcgtt ggaatgtgat atctggtgcg    960
gtggacgacc gtactccgaa ggaaagaggt gttgcgccat tactacccaa atacaacaag   1020
aacggatttg gaggcattgc caaagacgta caagataaag tccttgaaat accaaagtca   1080
agatatagtt cggttgatct tttcttgggt gggtcgaaat ttttcaatag gacttataac   1140
gacacaaatg tacctattaa tgaaaagta ttaggacgac tactagagaa tgataaggcg    1200
ccactggact atgatcttgc taaacatttt gcgcatctct acataagaga tccagtatct   1260
acattcgaag aactgttgaa tcaggacaac aaaacgtctt caaatcactt tgaaaacatc   1320
caaagtacaa attggcagac attacgtttt aaaccccca cacaacaagc aaccccggac    1380
aaaaaggatt ctcctggttg gagagtggaa ttcagaccat ttgaagtgca actattagat   1440
tttgagaacg ctgcgtattc cgtgctcata tacttgattg tcgatagcat tttgaccttt   1500
tccgataata ttaacgcata tattcatatg tccaaagtat gggaaaatat gaagatagcc   1560
catcacagag atgctatcct atttgaaaaa tttcattgga aaaatcatt tcgcaacgac    1620
accgatgtgg aaactgaaga ttattctata agcgagattt ccataatcc agagaatggt   1680
atatttcctc aatttgttac gccaatccta tgccaaaaag ggtttgtaac caaagattgg   1740
aaagaattaa agcattcttc caaacacgag agactatact attatttaaa gctaatttct   1800
gatagagcaa gcggtgaatt gccaacaaca gcaaaattct ttagaaattt tgtactacaa   1860
catccagatt acaaacatga ttcaaaaatt tcaaagtcga tcaattatga tttgctttct   1920
acgtgtgata gacttaccca tttagacgat tcaaaaggtg aattgacatc ctttttagga   1980
gctgaaattg cagaatatgt aaaaaaaaat aagccttcaa tagaaagcaa atgttaa      2037
```

<210> SEQ ID NO 2
<211> LENGTH: 678
<212> TYPE: PRT
<213> ORGANISM: Saccharomyces cerevisiae

<400> SEQUENCE: 2

```
Met Gly Leu Leu Ala Leu Gly Thr Pro Leu Gln Trp Phe Glu Ser Arg
1               5                   10                  15

Thr Tyr Asn Glu His Ile Arg Asp Glu Gly Ile Glu Gln Leu Leu Tyr
            20                  25                  30

Ile Phe Gln Ala Ala Gly Lys Arg Asp Asn Asp Pro Leu Phe Trp Gly
        35                  40                  45

Asp Glu Leu Glu Tyr Met Val Val Asp Phe Asp Lys Glu Arg Asn
    50                  55                  60

Ser Met Leu Asp Val Cys His Asp Lys Ile Leu Thr Glu Leu Asn Met
65                  70                  75                  80

Glu Asp Ser Ser Leu Cys Glu Ala Asn Asp Val Ser Phe His Pro Glu
                85                  90                  95

Tyr Gly Arg Tyr Met Leu Glu Ala Thr Pro Ala Ser Pro Tyr Leu Asn
            100                 105                 110

Tyr Val Gly Ser Tyr Val Glu Val Asn Met Gln Lys Arg Arg Ala Ile
        115                 120                 125

Ala Glu Tyr Lys Leu Ser Glu Tyr Ala Arg Gln Asp Ser Lys Asn Asn
    130                 135                 140

Leu His Val Gly Ser Arg Ser Val Pro Leu Thr Leu Thr Val Phe Pro
145                 150                 155                 160

Arg Met Gly Cys Pro Asp Phe Ile Asn Ile Lys Asp Pro Trp Asn His
                165                 170                 175
```

```
Lys Asn Ala Ala Ser Arg Ser Leu Phe Leu Pro Asp Glu Val Ile Asn
                180                 185                 190

Arg His Val Arg Phe Pro Asn Leu Thr Ala Ser Ile Arg Thr Arg Arg
            195                 200                 205

Gly Glu Lys Val Cys Met Asn Val Pro Met Tyr Lys Asp Ile Ala Thr
    210                 215                 220

Pro Glu Thr Asp Asp Ser Ile Tyr Asp Arg Asp Trp Phe Leu Pro Glu
225                 230                 235                 240

Asp Lys Glu Ala Lys Leu Ala Ser Lys Pro Gly Phe Ile Tyr Met Asp
                245                 250                 255

Ser Met Gly Phe Gly Met Gly Cys Ser Cys Leu Gln Val Thr Phe Gln
            260                 265                 270

Ala Pro Asn Ile Asn Lys Ala Arg Tyr Leu Tyr Asp Ala Leu Val Asn
        275                 280                 285

Phe Ala Pro Ile Met Leu Ala Phe Ser Ala Ala Pro Ala Phe Lys
290                 295                 300

Gly Trp Leu Ala Asp Gln Asp Val Arg Trp Asn Val Ile Ser Gly Ala
305                 310                 315                 320

Val Asp Asp Arg Thr Pro Lys Glu Arg Gly Val Ala Pro Leu Leu Pro
                325                 330                 335

Lys Tyr Asn Lys Asn Gly Phe Gly Gly Ile Ala Lys Asp Val Gln Asp
            340                 345                 350

Lys Val Leu Glu Ile Pro Lys Ser Arg Tyr Ser Ser Val Asp Leu Phe
        355                 360                 365

Leu Gly Gly Ser Lys Phe Phe Asn Arg Thr Tyr Asn Asp Thr Asn Val
    370                 375                 380

Pro Ile Asn Glu Lys Val Leu Gly Arg Leu Leu Glu Asn Asp Lys Ala
385                 390                 395                 400

Pro Leu Asp Tyr Asp Leu Ala Lys His Phe Ala His Leu Tyr Ile Arg
                405                 410                 415

Asp Pro Val Ser Thr Phe Glu Glu Leu Leu Asn Gln Asp Asn Lys Thr
            420                 425                 430

Ser Ser Asn His Phe Glu Asn Ile Gln Ser Thr Asn Trp Gln Thr Leu
        435                 440                 445

Arg Phe Lys Pro Pro Thr Gln Gln Ala Thr Pro Asp Lys Lys Asp Ser
    450                 455                 460

Pro Gly Trp Arg Val Glu Phe Arg Pro Phe Glu Val Gln Leu Leu Asp
465                 470                 475                 480

Phe Glu Asn Ala Ala Tyr Ser Val Leu Ile Tyr Leu Ile Val Asp Ser
                485                 490                 495

Ile Leu Thr Phe Ser Asp Asn Ile Asn Ala Tyr Ile His Met Ser Lys
            500                 505                 510

Val Trp Glu Asn Met Lys Ile Ala His His Arg Asp Ala Ile Leu Phe
        515                 520                 525

Glu Lys Phe His Trp Lys Lys Ser Phe Arg Asn Asp Thr Asp Val Glu
    530                 535                 540

Thr Glu Asp Tyr Ser Ile Ser Glu Ile Phe His Asn Pro Glu Asn Gly
545                 550                 555                 560

Ile Phe Pro Gln Phe Val Thr Pro Ile Leu Cys Gln Lys Gly Phe Val
                565                 570                 575

Thr Lys Asp Trp Lys Glu Leu Lys His Ser Ser Lys His Glu Arg Leu
            580                 585                 590
```

Tyr Tyr Tyr Leu Lys Leu Ile Ser Asp Arg Ala Ser Gly Glu Leu Pro
            595                 600                 605

Thr Thr Ala Lys Phe Phe Arg Asn Phe Val Leu Gln His Pro Asp Tyr
        610                 615                 620

Lys His Asp Ser Lys Ile Ser Lys Ser Ile Asn Tyr Asp Leu Leu Ser
625                 630                 635                 640

Thr Cys Asp Arg Leu Thr His Leu Asp Asp Ser Lys Gly Glu Leu Thr
                645                 650                 655

Ser Phe Leu Gly Ala Glu Ile Ala Glu Tyr Val Lys Lys Asn Lys Pro
            660                 665                 670

Ser Ile Glu Ser Lys Cys
        675

<210> SEQ ID NO 3
<211> LENGTH: 2037
<212> TYPE: DNA
<213> ORGANISM: Artificial sequence
<220> FEATURE:
<223> OTHER INFORMATION: GSH1 with A373G mutation

<400> SEQUENCE: 3

| | | |
|---|---|---|
| atgggactct tagctttggg cacgcctttg cagtggtttg agtctaggac gtacaatgaa | | 60 |
| cacataaggg atgaaggtat cgagcagttg ttgtatattt tccaagctgc tggtaaaaga | | 120 |
| gacaatgacc ctcttttttg gggagacgag cttgagtaca tggttgtaga ttttgatgat | | 180 |
| aaggagagaa attctatgct cgacgtttgc catgacaaga tactcactga gcttaatatg | | 240 |
| gaggattcgt ccctttgtga ggctaacgat gtgagttttc accctgagta tggccggtat | | 300 |
| atgttagagg caacaccagc ttctccatat ttgaattacg tgggtagtta cgttgaggtt | | 360 |
| aacatgcaaa aaggacgtgc cattgcagaa tataagctat ctgaatatgc gagacaagat | | 420 |
| agtaaaaata acttgcatgt gggctccagg tctgtccctt tgacgctgac tgtcttcccg | | 480 |
| aggatgggat gccccgactt tattaacatt aaggatccgt ggaatcataa aaatgccgct | | 540 |
| tccaggtctc tgttttacc cgatgaagtc attaacagac atgtcaggtt tcctaacttg | | 600 |
| acagcatcca tcaggaccag gcgtggtgaa aaagtttgca tgaatgttcc catgtataaa | | 660 |
| gatatagcta ctccagaaac ggatgactcc atctacgatc gagattggtt tttaccagaa | | 720 |
| gacaaagagg cgaaactggc ttccaaaccg ggtttcattt atatggattc catgggtttt | | 780 |
| ggcatgggct gttcgtgctt acaagtgacc tttcaggcac ccaatatcaa caaggcacgt | | 840 |
| tacctgtacg atgcattagt gaattttgca cctataatgc tagccttctc tgccgctgcg | | 900 |
| cctgctttta aggttggct agccgaccaa gatgttcgtt ggaatgtgat atctggtgcg | | 960 |
| gtggacgacc gtactccgaa ggaaagaggt gttgcgccat tactacccaa atacaacaag | | 1020 |
| aacggatttg gaggcattgc caaagactta caagataaag tccttgaaat accaaagtca | | 1080 |
| agatatagtt cggttgatct tttcttgggt gggtcgaaat ttttcaatag gacttataac | | 1140 |
| gacacaaatg tacctattaa tgaaaaagta ttaggacgac tactagagaa tgataaggcg | | 1200 |
| ccactggact atgatcttgc taaacatttt gcgcatctct acataagaga tccagtatct | | 1260 |
| acattcgaag aactgttgaa tcaggacaac aaaacgtctt caaatcactt tgaaaacatc | | 1320 |
| caaagtacaa attggcagac attacgtttt aaaccccca cacaacaagc aaccccggac | | 1380 |
| aaaaaggatt ctcctggttg agagtggaa ttcagaccat tgaagtgca actattgat | | 1440 |
| tttgagaacg ctgcgtattc cgtgctcata tacttgattg tcgatagcat ttgacctttt | | 1500 |
| tccgataata ttaacgcata tattcatatg tccaaagtat gggaaaatat gaagatagcc | | 1560 |

```
catcacagag atgctatcct atttgaaaaa tttcattgga aaaaatcatt tcgcaacgac    1620
accgatgtgg aaactgaaga ttattctata agcgagattt tccataatcc agagaatggt    1680
atatttcctc aatttgttac gccaatccta tgccaaaaag ggtttgtaac caaagattgg    1740
aaagaattaa agcattcttc caaacacgag agactatact attatttaaa gctaatttct    1800
gatagagcaa gcggtgaatt gccaacaaca gcaaaattct ttagaaattt tgtactacaa    1860
catccagatt acaaacatga ttcaaaaatt tcaaagtcga tcaattatga tttgcttttct   1920 acgtgtgata gacttaccca tttagacgat tcaaaaggtg aattgacatc cttttttagga   1980 gctgaaattg cagaatatgt aaaaaaaaat aagccttcaa tagaaagcaa atgttaa       2037
```

<210> SEQ ID NO 4
<211> LENGTH: 678
<212> TYPE: PRT
<213> ORGANISM: Artificial sequence
<220> FEATURE:
<223> OTHER INFORMATION: Gsh1 with Arg125Gly mutation
<400> SEQUENCE: 4

```
Met Gly Leu Leu Ala Leu Gly Thr Pro Leu Gln Trp Phe Glu Ser Arg
1               5                   10                  15

Thr Tyr Asn Glu His Ile Arg Asp Glu Gly Ile Glu Gln Leu Leu Tyr
            20                  25                  30

Ile Phe Gln Ala Ala Gly Lys Arg Asp Asn Asp Pro Leu Phe Trp Gly
        35                  40                  45

Asp Glu Leu Glu Tyr Met Val Val Asp Phe Asp Lys Glu Arg Asn
    50                  55                  60

Ser Met Leu Asp Val Cys His Asp Lys Ile Leu Thr Glu Leu Asn Met
65                  70                  75                  80

Glu Asp Ser Ser Leu Cys Glu Ala Asn Asp Val Ser Phe His Pro Glu
                85                  90                  95

Tyr Gly Arg Tyr Met Leu Glu Ala Thr Pro Ala Ser Pro Tyr Leu Asn
            100                 105                 110

Tyr Val Gly Ser Tyr Val Glu Val Asn Met Gln Lys Gly Arg Ala Ile
        115                 120                 125

Ala Glu Tyr Lys Leu Ser Glu Tyr Ala Arg Gln Asp Ser Lys Asn Asn
    130                 135                 140

Leu His Val Gly Ser Arg Ser Val Pro Leu Thr Leu Thr Val Phe Pro
145                 150                 155                 160

Arg Met Gly Cys Pro Asp Phe Ile Asn Ile Lys Asp Pro Trp Asn His
                165                 170                 175

Lys Asn Ala Ala Ser Arg Ser Leu Phe Leu Pro Asp Glu Val Ile Asn
            180                 185                 190

Arg His Val Arg Phe Pro Asn Leu Thr Ala Ser Ile Arg Thr Arg Arg
        195                 200                 205

Gly Glu Lys Val Cys Met Asn Val Pro Met Tyr Lys Asp Ile Ala Thr
    210                 215                 220

Pro Glu Thr Asp Asp Ser Ile Tyr Asp Arg Asp Trp Phe Leu Pro Glu
225                 230                 235                 240

Asp Lys Glu Ala Lys Leu Ala Ser Lys Pro Gly Phe Ile Tyr Met Asp
                245                 250                 255

Ser Met Gly Phe Gly Met Gly Cys Ser Cys Leu Gln Val Thr Phe Gln
            260                 265                 270

Ala Pro Asn Ile Asn Lys Ala Arg Tyr Leu Tyr Asp Ala Leu Val Asn
```

```
                275                 280                 285
Phe Ala Pro Ile Met Leu Ala Phe Ser Ala Ala Pro Ala Phe Lys
290                 295                 300
Gly Trp Leu Ala Asp Gln Asp Val Arg Trp Asn Val Ile Ser Gly Ala
305                 310                 315                 320
Val Asp Asp Arg Thr Pro Lys Glu Arg Gly Val Ala Pro Leu Leu Pro
                325                 330                 335
Lys Tyr Asn Lys Asn Gly Phe Gly Gly Ile Ala Lys Asp Val Gln Asp
            340                 345                 350
Lys Val Leu Glu Ile Pro Lys Ser Arg Tyr Ser Val Asp Leu Phe
            355                 360                 365
Leu Gly Gly Ser Lys Phe Phe Asn Arg Thr Tyr Asn Asp Thr Asn Val
        370                 375                 380
Pro Ile Asn Glu Lys Val Leu Gly Arg Leu Leu Glu Asn Asp Lys Ala
385                 390                 395                 400
Pro Leu Asp Tyr Asp Leu Ala Lys His Phe Ala His Leu Tyr Ile Arg
                405                 410                 415
Asp Pro Val Ser Thr Phe Glu Glu Leu Leu Asn Gln Asp Asn Lys Thr
            420                 425                 430
Ser Ser Asn His Phe Glu Asn Ile Gln Ser Thr Asn Trp Gln Thr Leu
            435                 440                 445
Arg Phe Lys Pro Pro Thr Gln Gln Ala Thr Pro Asp Lys Lys Asp Ser
450                 455                 460
Pro Gly Trp Arg Val Glu Phe Arg Pro Phe Glu Val Gln Leu Leu Asp
465                 470                 475                 480
Phe Glu Asn Ala Ala Tyr Ser Val Leu Ile Tyr Leu Ile Val Asp Ser
                485                 490                 495
Ile Leu Thr Phe Ser Asp Asn Ile Asn Ala Tyr Ile His Met Ser Lys
            500                 505                 510
Val Trp Glu Asn Met Lys Ile Ala His His Arg Asp Ala Ile Leu Phe
        515                 520                 525
Glu Lys Phe His Trp Lys Lys Ser Phe Arg Asn Asp Thr Asp Val Glu
        530                 535                 540
Thr Glu Asp Tyr Ser Ile Ser Glu Ile Phe His Asn Pro Glu Asn Gly
545                 550                 555                 560
Ile Phe Pro Gln Phe Val Thr Pro Ile Leu Cys Gln Lys Gly Phe Val
                565                 570                 575
Thr Lys Asp Trp Lys Glu Leu Lys His Ser Ser Lys His Glu Arg Leu
            580                 585                 590
Tyr Tyr Tyr Leu Lys Leu Ile Ser Asp Arg Ala Ser Gly Glu Leu Pro
        595                 600                 605
Thr Thr Ala Lys Phe Phe Arg Asn Phe Val Leu Gln His Pro Asp Tyr
        610                 615                 620
Lys His Asp Ser Lys Ile Ser Lys Ser Ile Asn Tyr Asp Leu Leu Ser
625                 630                 635                 640
Thr Cys Asp Arg Leu Thr His Leu Asp Asp Ser Lys Gly Glu Leu Thr
                645                 650                 655
Ser Phe Leu Gly Ala Glu Ile Ala Glu Tyr Val Lys Lys Asn Lys Pro
            660                 665                 670
Ser Ile Glu Ser Lys Cys
            675

<210> SEQ ID NO 5
```

<211> LENGTH: 1764
<212> TYPE: DNA
<213> ORGANISM: Saccharomyces cerevisiae

<400> SEQUENCE: 5

```
atgatgaatc cacacgttca agaaaatttg caagcaatcc acaacgcctt aagcaatttt      60
gatacgtcat ttttatcgga ggatgaagaa gattattgcc ctctttgtat tgaaccaatg     120
gatattactg ataaaaattt ttttccttgt ccctgtggtt atcaaatttg tcaattttgc     180
tacaataata tcagacaaaa tccagaatta aatggccgtt gcccagcatg tcgtcgtaaa     240
tatgatgacg agaacgtcag atacgtcaca ttatctccgg aggagttaaa aatggagaga     300
gccaagctcg ctaggaagga gaaagaaaga aagcatagag aaaaagaacg taaagagaat     360
gaatatacga ataggaaaca tttatctggt accagagtta tccaaaagaa tttagtgtac     420
gttgttggca tcaatcctcc tgttccatac gaggaagttg cgcccactct gaaatctgaa     480
aaatattttg gccaatatgg taagataaat aagattgtgg ttaatagaaa aacaccccat     540
tctaacaaca caaccagcga gcattatcac catcattcac caggatatgg cgtttacata     600
accttcggat ccaaggacga tgctgcaaga tgtatagctc aggtagacgg gacgtatatg     660
gatggccgcc tgatcaaagc tgcctacggt actactaaat actgttcttc ttatttaaga     720
ggattgccat gcccaaatcc caactgtatg ttttttgcatg aacctggtga gaagctgat      780
tcttttaata aaagagaact ccacaataaa caacaagcgc aacagcaaag tggcggaact     840
gcattcacta gatctggaat acacaacaat atatctacca gtaccgctgg ttcaaatacc     900
aatttactaa gtgaaaattt cacaggcaca ccttcaccgg cggcgatgag ggctcagtta     960
catcatgaca gccatacaaa cgctggaaca ccggtattaa cacctgctcc ggtccctgca    1020
gggtcaaatc cttggggagt tactcaatca gcaacacctg taacctctat caatctctct    1080
aaaaacagca gctccataaa cttgccaaca ttaaatgatt ctctgggcca tcatactacc    1140
cccacaacag agaataccat cacaagtacg acaactacta ccaataccaa tgctacaagt    1200
cactcccatg gtagcaagaa gaagcaatct cttgctgcag aggaatacaa agatccttat    1260
gacgcactag ggaatgctgt tgactttttg gatgcaagac tacattctct atcaaattat    1320
cagaagcgcc ctatatctat caaatccaat attattgacg aagaaactta taaaaagtat    1380
ccgtctttgt tttcttggga caagattgag gcctcaaaga aaagtgacaa tacattagcc    1440
aacaaacttg tggagatcct ggctataaag ccaatagact acactgcttc tgtcgttcaa    1500
ttcttgcaga gtgtcaatgt tggtgtaaat gacaatatta caatcacaga taatacgaaa    1560
actcccaccc aaccaataag actgcaaacc gtctcacagc aaatccaacc accattaaac    1620
gtcagtaccc ctccaccggg tatctttggt ccacaacata aggttcctat tcagcagcaa    1680
caaatgggtg ataccagctc aagaaattcc tctgatttac taaatcaact aatcaacgga    1740
aggaaaatta tcgccggtaa ttaa                                          1764
```

<210> SEQ ID NO 6
<211> LENGTH: 587
<212> TYPE: PRT
<213> ORGANISM: Saccharomyces cerevisiae

<400> SEQUENCE: 6

```
Met Met Asn Pro His Val Gln Glu Asn Leu Gln Ala Ile His Asn Ala
1               5                   10                  15

Leu Ser Asn Phe Asp Thr Ser Phe Leu Ser Glu Asp Glu Glu Asp Tyr
            20                  25                  30
```

-continued

```
Cys Pro Leu Cys Ile Glu Pro Met Asp Ile Thr Asp Lys Asn Phe Phe
            35                  40                  45

Pro Cys Pro Cys Gly Tyr Gln Ile Cys Gln Phe Cys Tyr Asn Asn Ile
    50                  55                  60

Arg Gln Asn Pro Glu Leu Asn Gly Arg Cys Pro Ala Cys Arg Arg Lys
65              70                  75                  80

Tyr Asp Asp Glu Asn Val Arg Tyr Val Thr Leu Ser Pro Glu Glu Leu
                85                  90                  95

Lys Met Glu Arg Ala Lys Leu Ala Arg Lys Glu Lys Glu Arg Lys His
            100                 105                 110

Arg Glu Lys Glu Arg Lys Glu Asn Glu Tyr Thr Asn Arg Lys His Leu
            115                 120                 125

Ser Gly Thr Arg Val Ile Gln Lys Asn Leu Val Tyr Val Gly Ile
    130                 135                 140

Asn Pro Pro Val Pro Tyr Glu Glu Val Ala Pro Thr Leu Lys Ser Glu
145             150                 155                 160

Lys Tyr Phe Gly Gln Tyr Gly Lys Ile Asn Lys Ile Val Val Asn Arg
            165                 170                 175

Lys Thr Pro His Ser Asn Asn Thr Thr Ser Glu His Tyr His His
            180                 185                 190

Ser Pro Gly Tyr Gly Val Tyr Ile Thr Phe Gly Ser Lys Asp Asp Ala
    195                 200                 205

Ala Arg Cys Ile Ala Gln Val Asp Gly Thr Tyr Met Asp Gly Arg Leu
    210                 215                 220

Ile Lys Ala Ala Tyr Gly Thr Thr Lys Tyr Cys Ser Ser Tyr Leu Arg
225                 230                 235                 240

Gly Leu Pro Cys Pro Asn Pro Asn Cys Met Phe Leu His Glu Pro Gly
            245                 250                 255

Glu Glu Ala Asp Ser Phe Asn Lys Arg Glu Leu His Asn Lys Gln Gln
            260                 265                 270

Ala Gln Gln Gln Ser Gly Gly Thr Ala Phe Thr Arg Ser Gly Ile His
    275                 280                 285

Asn Asn Ile Ser Thr Ser Thr Ala Gly Ser Asn Thr Asn Leu Leu Ser
    290                 295                 300

Glu Asn Phe Thr Gly Thr Pro Ser Pro Ala Ala Met Arg Ala Gln Leu
305             310                 315                 320

His His Asp Ser His Thr Asn Ala Gly Thr Pro Val Leu Thr Pro Ala
            325                 330                 335

Pro Val Pro Ala Gly Ser Asn Pro Trp Gly Val Thr Gln Ser Ala Thr
            340                 345                 350

Pro Val Thr Ser Ile Asn Leu Ser Lys Asn Ser Ser Ser Ile Asn Leu
            355                 360                 365

Pro Thr Leu Asn Asp Ser Leu Gly His His Thr Thr Pro Thr Thr Glu
    370                 375                 380

Asn Thr Ile Thr Ser Thr Thr Thr Thr Asn Thr Asn Ala Thr Ser
385                 390                 395                 400

His Ser His Gly Ser Lys Lys Lys Gln Ser Leu Ala Ala Glu Glu Tyr
            405                 410                 415

Lys Asp Pro Tyr Asp Ala Leu Gly Asn Ala Val Asp Phe Leu Asp Ala
            420                 425                 430

Arg Leu His Ser Leu Ser Asn Tyr Gln Lys Arg Pro Ile Ser Ile Lys
            435                 440                 445
```

```
Ser Asn Ile Ile Asp Glu Glu Thr Tyr Lys Lys Tyr Pro Ser Leu Phe
    450                 455                 460

Ser Trp Asp Lys Ile Glu Ala Ser Lys Lys Ser Asp Asn Thr Leu Ala
465                 470                 475                 480

Asn Lys Leu Val Glu Ile Leu Ala Ile Lys Pro Ile Asp Tyr Thr Ala
                485                 490                 495

Ser Val Val Gln Phe Leu Gln Ser Val Asn Val Gly Val Asn Asp Asn
                500                 505                 510

Ile Thr Ile Thr Asp Asn Thr Lys Thr Pro Thr Gln Pro Ile Arg Leu
            515                 520                 525

Gln Thr Val Ser Gln Ile Gln Pro Pro Leu Asn Val Ser Thr Pro
    530                 535                 540

Pro Pro Gly Ile Phe Gly Pro Gln His Lys Val Pro Ile Gln Gln Gln
545                 550                 555                 560

Gln Met Gly Asp Thr Ser Ser Arg Asn Ser Ser Asp Leu Leu Asn Gln
                565                 570                 575

Leu Ile Asn Gly Arg Lys Ile Ile Ala Gly Asn
            580                 585
```

<210> SEQ ID NO 7
<211> LENGTH: 1764
<212> TYPE: DNA
<213> ORGANISM: Artificial sequence
<220> FEATURE:
<223> OTHER INFORMATION: NOT4 with T1285A mutation

<400> SEQUENCE: 7

```
atgatgaatc cacacgttca agaaaatttg caagcaatcc acaacgcctt aagcaatttt      60
gatacgtcat ttttatcgga ggatgaagaa gattattgcc ctctttgtat tgaaccaatg     120
gatattactg ataaaaattt ttttccttgt ccctgtggtt atcaaatttg tcaattttgc     180
tacaataata tcagacaaaa tccagaatta aatggccgtt gcccagcatg tcgtcgtaaa     240
tatgatgacg agaacgtcag atacgtcaca ttatctccgg aggagttaaa aatggagaga     300
gccaagctcg ctaggaagga gaaagaaaga aagcatagag aaaaagaacg taaagagaat     360
gaatatacga ataggaaaca tttatctggt accagagtta tccaaaagaa tttagtgtac     420
gttgttggca tcaatcctcc tgttccatac gaggaagttg cgcccactct gaaatctgaa     480
aaatattttg gccaatatgg taagataaat aagattgtgg ttaatagaaa aacaccccat     540
tctaacaaca caaccagcga gcattatcac catcattcac aggatatggg cgtttacata     600
accttcggat ccaaggacga tgctgcaaga tgtatagctc aggtagacgg gacgtatatg     660
gatggccgcc tgatcaaagc tgcctacggt actactaaat actgttcttc ttatttaaga     720
ggattgccat gcccaaatcc caactgtatg ttttttgcatg aacctggtga agaagctgat     780
tcttttaata aaagagaact ccacaataaa caacaagcgc aacagcaaag tggcggaact     840
gcattcacta gatctggaat acacaacaat atatctacca gtaccgctgg ttcaaatacc     900
aatttactaa gtgaaaattt cacaggcaca ccttcaccgg cggcgatgag ggctcagtta     960
catcatgaca gccatacaaa cgctggaaca ccggtattaa cacctgctcc ggtccctgca    1020
gggtcaaatc cttggggagt tactcaatca gcaacacctg taacctctat caatctctct    1080
aaaaacagca gctccataaa cttgccaaca ttaaatgatt ctctgggcca tcatactacc    1140
cccacaacag agaataccat cacaagtacg acaactacta ccaataccaa tgctacaagt    1200
cactcccatg gtagcaagaa gaagcaatct cttgctgcag aggaatacaa agatccttat    1260
```

```
gacgcactag ggaatgctgt tgacattttg gatgcaagac tacattctct atcaaattat   1320
cagaagcgcc ctatatctat caaatccaat attattgacg aagaaactta taaaaagtat   1380
ccgtctttgt tttcttggga caagattgag gcctcaaaga aaagtgacaa tacattagcc   1440
aacaaacttg tggagatcct ggctataaag ccaatagact acactgcttc tgtcgttcaa   1500
ttcttgcaga gtgtcaatgt tggtgtaaat gacaatatta caatcacaga taatacgaaa   1560
actcccaccc aaccaataag actgcaaacc gtctcacagc aaatccaacc accattaaac   1620
gtcagtaccc ctccaccggg tatctttggt ccacaacata aggttcctat tcagcagcaa   1680
caaatgggtg atacaagctc aagaaattcc tctgatttac taaatcaact aatcaacgga   1740
aggaaaatta tcgccggtaa ttaa                                          1764
```

<210> SEQ ID NO 8
<211> LENGTH: 587
<212> TYPE: PRT
<213> ORGANISM: Artificial sequence
<220> FEATURE:
<223> OTHER INFORMATION: Not4 with Phe429Ile mutation

<400> SEQUENCE: 8

```
Met Met Asn Pro His Val Gln Glu Asn Leu Gln Ala Ile His Asn Ala
1               5                   10                  15

Leu Ser Asn Phe Asp Thr Ser Phe Leu Ser Glu Asp Glu Glu Asp Tyr
            20                  25                  30

Cys Pro Leu Cys Ile Glu Pro Met Asp Ile Thr Asp Lys Asn Phe Phe
        35                  40                  45

Pro Cys Pro Cys Gly Tyr Gln Ile Cys Gln Phe Cys Tyr Asn Asn Ile
    50                  55                  60

Arg Gln Asn Pro Glu Leu Asn Gly Arg Cys Pro Ala Cys Arg Arg Lys
65                  70                  75                  80

Tyr Asp Asp Glu Asn Val Arg Tyr Val Thr Leu Ser Pro Glu Glu Leu
                85                  90                  95

Lys Met Glu Arg Ala Lys Leu Ala Arg Lys Glu Lys Glu Arg Lys His
            100                 105                 110

Arg Glu Lys Glu Arg Lys Glu Asn Glu Tyr Thr Asn Arg Lys His Leu
        115                 120                 125

Ser Gly Thr Arg Val Ile Gln Lys Asn Leu Val Tyr Val Gly Ile
    130                 135                 140

Asn Pro Pro Val Pro Tyr Glu Glu Val Ala Pro Thr Leu Lys Ser Glu
145                 150                 155                 160

Lys Tyr Phe Gly Gln Tyr Gly Lys Ile Asn Lys Ile Val Val Asn Arg
                165                 170                 175

Lys Thr Pro His Ser Asn Asn Thr Thr Ser Glu His Tyr His His
            180                 185                 190

Ser Pro Gly Tyr Gly Val Tyr Ile Thr Phe Gly Ser Lys Asp Asp Ala
        195                 200                 205

Ala Arg Cys Ile Ala Gln Val Asp Gly Thr Tyr Met Asp Gly Arg Leu
    210                 215                 220

Ile Lys Ala Ala Tyr Gly Thr Thr Lys Tyr Cys Ser Ser Tyr Leu Arg
225                 230                 235                 240

Gly Leu Pro Cys Pro Asn Pro Asn Cys Met Phe Leu His Glu Pro Gly
                245                 250                 255

Glu Glu Ala Asp Ser Phe Asn Lys Arg Glu Leu His Asn Lys Gln Gln
            260                 265                 270
```

```
Ala Gln Gln Gln Ser Gly Gly Thr Ala Phe Thr Arg Ser Gly Ile His
            275                 280                 285

Asn Asn Ile Ser Thr Ser Thr Ala Gly Ser Asn Thr Asn Leu Leu Ser
290                 295                 300

Glu Asn Phe Thr Gly Thr Pro Ser Pro Ala Ala Met Arg Ala Gln Leu
305                 310                 315                 320

His His Asp Ser His Thr Asn Ala Gly Thr Pro Val Leu Thr Pro Ala
                325                 330                 335

Pro Val Pro Ala Gly Ser Asn Pro Trp Gly Val Thr Gln Ser Ala Thr
            340                 345                 350

Pro Val Thr Ser Ile Asn Leu Ser Lys Asn Ser Ser Ile Asn Leu
            355                 360                 365

Pro Thr Leu Asn Asp Ser Leu Gly His His Thr Thr Pro Thr Thr Glu
370                 375                 380

Asn Thr Ile Thr Ser Thr Thr Thr Thr Asn Thr Asn Ala Thr Ser
385                 390                 395                 400

His Ser His Gly Ser Lys Lys Lys Gln Ser Leu Ala Ala Glu Glu Tyr
                405                 410                 415

Lys Asp Pro Tyr Asp Ala Leu Gly Asn Ala Val Asp Ile Leu Asp Ala
            420                 425                 430

Arg Leu His Ser Leu Ser Asn Tyr Gln Lys Arg Pro Ile Ser Ile Lys
            435                 440                 445

Ser Asn Ile Ile Asp Glu Glu Thr Tyr Lys Lys Tyr Pro Ser Leu Phe
450                 455                 460

Ser Trp Asp Lys Ile Glu Ala Ser Lys Lys Ser Asp Asn Thr Leu Ala
465                 470                 475                 480

Asn Lys Leu Val Glu Ile Leu Ala Ile Lys Pro Ile Asp Tyr Thr Ala
                485                 490                 495

Ser Val Val Gln Phe Leu Gln Ser Val Asn Val Gly Val Asn Asp Asn
            500                 505                 510

Ile Thr Ile Thr Asp Asn Thr Lys Thr Pro Thr Gln Pro Ile Arg Leu
            515                 520                 525

Gln Thr Val Ser Gln Gln Ile Gln Pro Pro Leu Asn Val Ser Thr Pro
530                 535                 540

Pro Pro Gly Ile Phe Gly Pro Gln His Lys Val Pro Ile Gln Gln Gln
545                 550                 555                 560

Gln Met Gly Asp Thr Ser Ser Arg Asn Ser Ser Asp Leu Leu Asn Gln
                565                 570                 575

Leu Ile Asn Gly Arg Lys Ile Ile Ala Gly Asn
            580                 585

<210> SEQ ID NO 9
<211> LENGTH: 1755
<212> TYPE: DNA
<213> ORGANISM: Homo sapiens

<400> SEQUENCE: 9
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca aatcacttca tacccttttt ggagacaaat tatgcacagt tgcaactctt     240
cgtgaaacct atggtgaaat ggctgactgc tgtgcaaaac aagaacctga gaaaatgaa      300 tgcttcttgc aacacaaaga tgacaaccca aacctccccc gattggtgag accagaggtt     360
```

```
gatgtgatgt gcactgcttt tcatgacaat gaagagacat ttttgaaaaa atacttatat    420
gaaattgcca aagacatcc ttactttat gccccggaac tccttttctt tgctaaaagg      480
tataaagctg cttttacaga atgttgccaa gctgctgata aagctgcctg cctgttgcca    540
aagctcgatg aacttcggga tgaagggaag gcttcgtctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag gcggacctt    780 gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg cagatcctca tgaatgctat gccaaagtgt tcgatgaatt taaacctctt    1140
gtggaagagc ctcagaattt aatcaaacaa aattgtgagc ttttgagca gcttggagag    1200 tacaaattcc agaatgcgct attagttcgt tacaccaaga agtacccca agtgtcaact    1260 ccaactcttg tagaggtctc aagaaaccta ggaaaagtgg gcagcaaatg ttgtaaacat    1320
cctgaagcaa aagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg atgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc caaggcaaca    1620 aaagagcaac tgaaagctgt tatggatgat ttcgcagctt ttgtagaaa gtgctgcaag    1680 gctgacgata aggagacctg ctttgccgag gagggtaaaa aacttgttgc tgcaagtcaa    1740
gctgccttag gctta                                                    1755
```

<210> SEQ ID NO 10  
<211> LENGTH: 585  
<212> TYPE: PRT  
<213> ORGANISM: Homo sapiens

<400> SEQUENCE: 10

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
```

-continued

```
              115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
            195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
                260                 265                 270
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
                420                 425                 430
Val Gly Ser Lys Cys Cys Lys His Pro Glu Ala Lys Arg Met Pro Cys
            435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
    530                 535                 540
```

| Lys | Ala | Val | Met | Asp | Asp | Phe | Ala | Ala | Phe | Val | Glu | Lys | Cys | Cys | Lys |
|---|---|---|---|---|---|---|---|---|---|---|---|---|---|---|---|
| 545 | | | | 550 | | | | 555 | | | | 560 | | | |

| Ala | Asp | Asp | Lys | Glu | Thr | Cys | Phe | Ala | Glu | Glu | Gly | Lys | Lys | Leu | Val |
|---|---|---|---|---|---|---|---|---|---|---|---|---|---|---|---|
| | | | 565 | | | | 570 | | | | 575 | | | | |

| Ala | Ala | Ser | Gln | Ala | Ala | Leu | Gly | Leu |
|---|---|---|---|---|---|---|---|---|
| | | 580 | | | | 585 | | |

<210> SEQ ID NO 11
<211> LENGTH: 1827
<212> TYPE: DNA
<213> ORGANISM: Homo sapiens

<400> SEQUENCE: 11

| | |
|---|---:|
| atgaagtggg taagctttat ttcccttctt tttctcttta gctcggctta ttccaggagc | 60 |
| ttggataaaa gagatgcaca caagagtgag gttgctcatc ggtttaaaga tttgggagaa | 120 |
| gaaaatttca agccttggt gttgattgcc tttgctcagt atcttcagca gtgtccattt | 180 |
| gaagatcatg taaaattagt gaatgaagta actgaatttg caaaaacatg tgttgctgat | 240 |
| gagtcagctg aaaattgtga caaatcactt catacccttt ttggagacaa attatgcaca | 300 |
| gttgcaactc ttcgtgaaac ctatggtgaa atggctgact gctgtgcaaa acaagaacct | 360 |
| gagagaaatg aatgcttctt gcaacacaaa gatgacaacc caaacctccc ccgattggtg | 420 |
| agaccagagg ttgatgtgat gtgcactgct tttcatgaca tgaagagac attttttgaaa | 480 |
| aaatacttat atgaaattgc cagaagacat ccttactttt atgccccgga actcctttc | 540 |
| tttgctaaaa ggtataaagc tgcttttaca aatgttgcc aagctgctga taaagctgcc | 600 |
| tgcctgttgc caaagctcga tgaacttcgg gatgaaggga aggcttcgtc tgccaaacag | 660 |
| agactcaagt gtgccagtct ccaaaaattt ggagaaagag ctttcaaagc atgggcagta | 720 |
| gctcgcctga gccagagatt tcccaaagct gagtttgcag aagtttccaa gttagtgaca | 780 |
| gatcttacca aagtccacac ggaatgctgc catgagatc tgcttgaatg tgctgatgac | 840 |
| agggcggacc ttgccaagta tatctgtgaa aatcaagatt cgatctccag taaactgaag | 900 |
| gaatgctgtg aaaaacctct gttggaaaaa tcccactgca ttgccgaagt ggaaaatgat | 960 |
| gagatgcctg ctgacttgcc ttcattagct gctgattttg ttgaaagtaa ggatgtttgc | 1020 |
| aaaaactatg ctgaggcaaa ggatgtcttc ctgggcatgt ttttgtatga atatgcaaga | 1080 |
| aggcatcctg attactctgt cgtgctgctg ctgagacttg ccaagacata tgaaaccact | 1140 |
| ctagagaagt gctgtgccgc tgcagatcct catgaatgct atgccaaagt gttcgatgaa | 1200 |
| tttaaacctc ttgtggaaga gcctcagaat ttaatcaaac aaaattgtga gcttttttgag | 1260 |
| cagcttggag agtacaaatt ccagaatgcg ctattagttc gttacaccaa gaaagtaccc | 1320 |
| caagtgtcaa ctccaactct tgtagaggtc tcaagaaacc taggaaaagt gggcagcaaa | 1380 |
| tgttgtaaac atcctgaagc aaaaagaatg ccctgtgcag aagactatct atccgtggtc | 1440 |
| ctgaaccagt tatgtgtgtt gcatgagaaa acgccagtaa gtgacagagt caccaaatgc | 1500 |
| tgcacagaat ccttggtgaa caggcgacca tgcttttcag ctctggaagt cgatgaaaca | 1560 |
| tacgttccca agagtttaa tgctgaaaca ttcaccttcc atgcagatat atgcacactt | 1620 |
| tctgagaagg agagacaaat caagaaacaa actgcacttg ttgagctcgt gaaacacaag | 1680 |
| cccaaggcaa caaagagca actgaaagct gttatggatg atttcgcagc ttttgtagag | 1740 |
| aagtgctgca aggctgacga taaggagacc tgctttgccg aggagggtaa aaaacttgtt | 1800 |
| gctgcaagtc aagctgcctt aggctta | 1827 |

<210> SEQ ID NO 12
<211> LENGTH: 609
<212> TYPE: PRT
<213> ORGANISM: Homo sapiens

<400> SEQUENCE: 12

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys

```
                370                 375                 380
Cys Ala Ala Ala Asp Pro His Glu Cys Tyr Ala Lys Val Phe Asp Glu
385                 390                 395                 400

Phe Lys Pro Leu Val Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
                530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu

<210> SEQ ID NO 13
<211> LENGTH: 2108
<212> TYPE: PRT
<213> ORGANISM: Saccharomyces cerevisiae

<400> SEQUENCE: 13

Met Leu Ser Ala Thr Tyr Arg Asp Leu Asn Thr Ala Ser Asn Leu Glu
1               5                   10                  15

Thr Ser Lys Glu Lys Gln Ala Ala Gln Ile Val Ile Ala Gln Ile Ser
                20                  25                  30

Leu Leu Phe Thr Thr Leu Asn Asn Asp Asn Phe Glu Ser Val Glu Arg
                35                  40                  45

Glu Ile Arg His Ile Leu Asp Arg Ser Ser Val Asp Ile Tyr Ile Lys
        50                  55                  60

Val Trp Glu Arg Leu Leu Thr Leu Ser Ser Arg Asp Ile Leu Gln Ala
65                  70                  75                  80

Gly Lys Phe Leu Leu Gln Glu Asn Leu Leu His Arg Leu Leu Leu Glu
                85                  90                  95

Phe Ala Lys Asp Leu Pro Lys Lys Ser Thr Asp Leu Ile Glu Leu Leu
                100                 105                 110

Lys Glu Arg Thr Phe Asn Asn Gln Glu Phe Gln Lys Gln Thr Gly Ile
                115                 120                 125

Thr Leu Ser Leu Phe Ile Asp Leu Phe Asp Lys Ser Ala Asn Lys Asp
```

```
            130                 135                 140
Ile Ile Glu Ser Leu Asp Arg Ser Ser Gln Ile Asn Asp Phe Lys Thr
145                 150                 155                 160

Ile Lys Met Asn His Thr Asn Tyr Leu Arg Asn Phe Phe Leu Gln Thr
                165                 170                 175

Thr Pro Glu Thr Leu Glu Ser Asn Leu Arg Asp Leu Leu His Ser Leu
                180                 185                 190

Glu Gly Glu Ser Leu Asn Asp Leu Leu Ala Leu Leu Leu Ser Glu Ile
                195                 200                 205

Leu Ser Pro Gly Ser Gln Asn Leu Gln Asn Asp Pro Thr Arg Ser Trp
210                 215                 220

Leu Thr Pro Pro Met Val Leu Asp Ala Thr Asn Arg Gly Asn Val Ile
225                 230                 235                 240

Ala Arg Ser Ile Ser Ser Leu Gln Ala Asn Gln Ile Asn Trp Asn Arg
                245                 250                 255

Val Phe Asn Leu Met Ser Thr Lys Tyr Phe Leu Ser Ala Pro Leu Met
                260                 265                 270

Pro Thr Thr Ala Ser Leu Ser Cys Leu Phe Ala Ala Leu His Asp Gly
                275                 280                 285

Pro Val Ile Asp Glu Phe Phe Ser Cys Asp Trp Lys Val Ile Phe Lys
                290                 295                 300

Leu Asp Leu Ala Ile Gln Leu His Lys Trp Ser Val Gln Asn Gly Cys
305                 310                 315                 320

Phe Asp Leu Leu Asn Ala Glu Gly Thr Arg Lys Val Ser Glu Thr Ile
                325                 330                 335

Pro Asn Thr Lys Gln Ser Leu Leu Tyr Leu Leu Ser Ile Ala Ser Leu
                340                 345                 350

Asn Leu Glu Leu Phe Leu Gln Arg Glu Glu Leu Ser Asp Gly Pro Met
                355                 360                 365

Leu Ala Tyr Phe Gln Glu Cys Phe Phe Glu Asp Phe Asn Tyr Ala Pro
                370                 375                 380

Glu Tyr Leu Ile Leu Ala Leu Val Lys Glu Met Lys Arg Phe Val Leu
385                 390                 395                 400

Leu Ile Glu Asn Arg Thr Val Ile Asp Glu Ile Leu Ile Thr Leu Leu
                405                 410                 415

Ile Gln Val His Asn Lys Ser Pro Ser Ser Phe Lys Asp Val Ile Ser
                420                 425                 430

Thr Ile Thr Asp Asp Ser Lys Ile Val Asp Ala Ala Lys Ile Ile Ile
                435                 440                 445

Asn Ser Asp Asp Ala Pro Ile Ala Asn Phe Leu Lys Ser Leu Leu Asp
450                 455                 460

Thr Gly Arg Leu Asp Thr Val Ile Asn Lys Leu Pro Phe Asn Glu Ala
465                 470                 475                 480

Phe Lys Ile Leu Pro Cys Ala Arg Gln Ile Gly Trp Glu Gly Phe Asp
                485                 490                 495

Thr Phe Leu Lys Thr Lys Val Ser Pro Ser Asn Val Asp Val Val Leu
                500                 505                 510

Glu Ser Leu Glu Val Gln Thr Lys Met Thr Asp Thr Asn Thr Pro Phe
                515                 520                 525

Arg Ser Leu Lys Thr Phe Asp Leu Phe Ala Phe His Ser Leu Ile Glu
                530                 535                 540

Val Leu Asn Lys Cys Pro Leu Asp Val Leu Gln Leu Gln Arg Phe Glu
545                 550                 555                 560
```

```
Ser Leu Glu Phe Ser Leu Leu Ile Ala Phe Pro Arg Leu Ile Asn Phe
                565                 570                 575

Gly Phe Gly His Asp Glu Ala Ile Leu Ala Asn Gly Asp Ile Ala Gly
            580                 585                 590

Ile Asn Asn Asp Ile Glu Lys Glu Met Gln Asn Tyr Leu Gln Lys Met
        595                 600                 605

Tyr Ser Gly Glu Leu Ala Ile Lys Asp Val Ile Glu Leu Leu Arg Arg
    610                 615                 620

Leu Arg Asp Ser Asp Leu Pro Arg Asp Gln Glu Val Phe Thr Cys Ile
625                 630                 635                 640

Thr His Ala Val Ile Ala Glu Ser Thr Phe Phe Gln Asp Tyr Pro Leu
                645                 650                 655

Asp Ala Leu Ala Thr Thr Ser Val Leu Phe Gly Ser Met Ile Leu Phe
            660                 665                 670

Gln Leu Leu Arg Gly Phe Val Leu Asp Val Ala Phe Arg Ile Ile Met
        675                 680                 685

Arg Phe Ala Lys Glu Pro Pro Glu Ser Lys Met Phe Lys Phe Ala Val
    690                 695                 700

Gln Ala Ile Tyr Ala Phe Arg Ile Arg Leu Ala Glu Tyr Pro Gln Tyr
705                 710                 715                 720

Cys Lys Asp Leu Leu Arg Asp Val Pro Ala Leu Lys Ser Gln Ala Gln
                725                 730                 735

Val Tyr Gln Ser Ile Val Glu Ala Ala Thr Leu Ala Asn Ala Pro Lys
            740                 745                 750

Glu Arg Ser Arg Pro Val Gln Glu Met Ile Pro Leu Lys Phe Phe Ala
        755                 760                 765

Val Asp Glu Val Ser Cys Gln Ile Asn Gln Glu Gly Ala Pro Lys Asp
    770                 775                 780

Val Val Glu Lys Val Leu Phe Val Leu Asn Asn Val Thr Leu Ala Asn
785                 790                 795                 800

Leu Asn Asn Lys Val Asp Glu Leu Lys Lys Ser Leu Thr Pro Asn Tyr
                805                 810                 815

Phe Ser Trp Phe Ser Thr Tyr Leu Val Thr Gln Arg Ala Lys Thr Glu
            820                 825                 830

Pro Asn Tyr His Asp Leu Tyr Ser Lys Val Ile Val Ala Met Gly Ser
        835                 840                 845

Gly Leu Leu His Gln Phe Met Val Asn Val Thr Leu Arg Gln Leu Phe
    850                 855                 860

Val Leu Leu Ser Thr Lys Asp Glu Gln Ala Ile Asp Lys Lys His Leu
865                 870                 875                 880

Lys Asn Leu Ala Ser Trp Leu Gly Cys Ile Thr Leu Ala Leu Asn Lys
                885                 890                 895

Pro Ile Lys His Lys Asn Ile Ala Phe Arg Glu Met Leu Ile Glu Ala
            900                 905                 910

Tyr Lys Glu Asn Arg Leu Glu Ile Val Val Pro Phe Val Thr Lys Ile
        915                 920                 925

Leu Gln Arg Ala Ser Glu Ser Lys Ile Phe Lys Pro Pro Asn Pro Trp
    930                 935                 940

Thr Val Gly Ile Leu Lys Leu Leu Ile Glu Leu Asn Glu Lys Ala Asn
945                 950                 955                 960

Trp Lys Leu Ser Leu Thr Phe Glu Val Glu Val Leu Leu Lys Ser Phe
                965                 970                 975
```

```
Asn Leu Thr Thr Lys Ser Leu Lys Pro Ser Asn Phe Ile Asn Thr Pro
        980                 985                 990

Glu Val Ile Glu Thr Leu Ser Gly Ala Leu Gly Ser Ile Thr Leu Glu
        995                 1000                1005

Gln Gln Gln Thr Glu Gln Gln Arg Gln Ile Ile Leu Met Gln Gln
    1010                1015                1020

His Gln Gln Gln Met Leu Ile Tyr Gln Arg Gln Gln Gln Gln
    1025                1030                1035

Gln Gln Arg Gln Gln Gln Gln His His Ile Ser Ala Asn Thr
    1040                1045                1050

Ile Ala Asp Gln Gln Ala Ala Phe Gly Gly Glu Gly Ser Ile Ser
    1055                1060                1065

His Asp Asn Pro Phe Asn Asn Leu Leu Gly Ser Thr Ile Phe Val
    1070                1075                1080

Thr His Pro Asp Leu Lys Arg Val Phe Gln Met Ala Leu Ala Lys
    1085                1090                1095

Ser Val Arg Glu Ile Leu Leu Glu Val Val Glu Lys Ser Ser Gly
    1100                1105                1110

Ile Ala Val Val Thr Thr Thr Lys Ile Ile Leu Lys Asp Phe Ala
    1115                1120                1125

Thr Glu Val Asp Glu Ser Lys Leu Lys Thr Ala Ala Ile Ile Met
    1130                1135                1140

Val Arg His Leu Ala Gln Ser Leu Ala Arg Ala Thr Ser Ile Glu
    1145                1150                1155

Pro Leu Lys Glu Gly Ile Arg Ser Thr Met Gln Ser Leu Ala Pro
    1160                1165                1170

Asn Leu Met Ser Leu Ser Ser Pro Ala Glu Glu Leu Asp Thr
    1175                1180                1185

Ala Ile Asn Glu Asn Ile Gly Ile Ala Leu Val Leu Ile Glu Lys
    1190                1195                1200

Ala Ser Met Asp Lys Ser Thr Gln Asp Leu Ala Asp Gln Leu Met
    1205                1210                1215

Gln Ala Ile Ala Ile Arg Arg Tyr His Lys Glu Arg Arg Ala Asp
    1220                1225                1230

Gln Pro Phe Ile Thr Gln Asn Thr Asn Pro Tyr Ser Leu Ser Leu
    1235                1240                1245

Pro Glu Pro Leu Gly Leu Lys Asn Thr Gly Val Thr Pro Gln Gln
    1250                1255                1260

Phe Arg Val Tyr Glu Glu Phe Gly Lys Asn Ile Pro Asn Leu Asp
    1265                1270                1275

Val Ile Pro Phe Ala Gly Leu Pro Ala His Ala Pro Pro Met Thr
    1280                1285                1290

Gln Asn Val Gly Leu Thr Gln Pro Gln Gln Gln Ala Gln Met
    1295                1300                1305

Pro Thr Gln Ile Leu Thr Ser Glu Gln Ile Arg Ala Gln Gln Gln
    1310                1315                1320

Gln Gln Gln Leu Gln Lys Ser Arg Leu Asn Gln Pro Ser Gln Ser
    1325                1330                1335

Ala Gln Pro Pro Gly Val Asn Val Pro Asn Pro Gln Gly Gly Ile
    1340                1345                1350

Ala Ala Val Gln Ser Asp Leu Glu Gln Asn Gln Arg Val Leu Val
    1355                1360                1365

His Leu Met Asp Ile Leu Val Ser Gln Ile Lys Glu Asn Ala Thr
```

```
                    1370                1375                1380
Lys Asn Asn Leu Ala Glu Leu Gly Asp Gln Asn Gln Ile Lys Thr
    1385                1390                1395
Ile Ile Phe Gln Ile Leu Thr Phe Ile Ala Lys Ser Ala Gln Lys
    1400                1405                1410
Asp Gln Leu Ala Leu Lys Val Ser Gln Ala Val Val Asn Ser Leu
    1415                1420                1425
Phe Ala Thr Ser Glu Ser Pro Leu Cys Arg Glu Val Leu Ser Leu
    1430                1435                1440
Leu Leu Glu Lys Leu Cys Ser Leu Ser Leu Val Ala Arg Lys Asp
    1445                1450                1455
Val Val Trp Trp Leu Val Tyr Ala Leu Asp Ser Arg Lys Phe Asn
    1460                1465                1470
Val Pro Val Ile Arg Ser Leu Leu Glu Val Asn Leu Ile Asp Ala
    1475                1480                1485
Thr Glu Leu Asp Asn Val Leu Val Thr Ala Met Lys Asn Lys Met
    1490                1495                1500
Glu Asn Ser Thr Glu Phe Ala Met Lys Leu Ile Gln Asn Thr Val
    1505                1510                1515
Leu Ser Asp Asp Pro Ile Leu Met Arg Met Asp Phe Ile Lys Thr
    1520                1525                1530
Leu Glu His Leu Ala Ser Ser Glu Asp Glu Asn Val Lys Lys Phe
    1535                1540                1545
Ile Lys Glu Phe Glu Asp Thr Lys Ile Met Pro Val Arg Lys Gly
    1550                1555                1560
Thr Lys Thr Thr Arg Thr Glu Lys Leu Tyr Leu Val Phe Thr Glu
    1565                1570                1575
Trp Val Lys Leu Leu Gln Arg Val Glu Asn Asn Asp Val Ile Thr
    1580                1585                1590
Thr Val Phe Ile Lys Gln Leu Val Glu Lys Gly Val Ile Ser Asp
    1595                1600                1605
Thr Asp Asn Leu Leu Thr Phe Val Lys Ser Ser Leu Glu Leu Ser
    1610                1615                1620
Val Ser Ser Phe Lys Glu Ser Asp Pro Thr Asp Glu Val Phe Ile
    1625                1630                1635
Ala Ile Asp Ala Leu Gly Ser Leu Ile Ile Lys Leu Leu Ile Leu
    1640                1645                1650
Gln Gly Phe Lys Asp Asp Thr Arg Arg Asp Tyr Ile Asn Ala Ile
    1655                1660                1665
Phe Ser Val Ile Val Leu Val Phe Ala Lys Asp His Ser Gln Glu
    1670                1675                1680
Gly Thr Thr Phe Asn Glu Arg Pro Tyr Phe Arg Leu Phe Ser Asn
    1685                1690                1695
Ile Leu Tyr Glu Trp Ala Thr Ile Arg Thr His Asn Phe Val Arg
    1700                1705                1710
Ile Ser Asp Ser Ser Thr Arg Gln Glu Leu Ile Glu Phe Asp Ser
    1715                1720                1725
Val Phe Tyr Asn Thr Phe Ser Gly Tyr Leu His Ala Leu Gln Pro
    1730                1735                1740
Phe Ala Phe Pro Gly Phe Ser Phe Ala Trp Val Thr Leu Leu Ser
    1745                1750                1755
His Arg Met Leu Leu Pro Ile Met Leu Arg Leu Pro Asn Lys Ile
    1760                1765                1770
```

Gly Trp Glu Lys Leu Met Leu Leu Ile Ile Asp Leu Phe Lys Phe
1775                1780                    1785

Leu Asp Gln Tyr Thr Ser Lys His Ala Val Ser Asp Ala Val Ser
1790                1795                    1800

Val Val Tyr Lys Gly Thr Leu Arg Val Ile Leu Gly Ile Ser Asn
1805                1810                    1815

Asp Met Pro Ser Phe Leu Ile Glu Asn His Tyr Glu Leu Met Asn
1820                1825                    1830

Asn Leu Pro Pro Thr Tyr Phe Gln Leu Lys Asn Val Ile Leu Ser
1835                1840                    1845

Ala Ile Pro Lys Asn Met Thr Val Pro Asn Pro Tyr Asp Val Asp
1850                1855                    1860

Leu Asn Met Glu Asp Ile Pro Ala Cys Lys Glu Leu Pro Glu Val
1865                1870                    1875

Phe Phe Asp Pro Val Ile Asp Leu His Ser Leu Lys Lys Pro Val
1880                1885                    1890

Asp Asn Tyr Leu Arg Ile Pro Ser Asn Ser Leu Leu Arg Thr Ile
1895                1900                    1905

Leu Ser Ala Ile Tyr Lys Asp Thr Tyr Asp Ile Lys Lys Gly Val
1910                1915                    1920

Gly Tyr Asp Phe Leu Ser Val Asp Ser Lys Leu Ile Arg Ala Ile
1925                1930                    1935

Val Leu His Val Gly Ile Glu Ala Gly Ile Glu Tyr Lys Arg Thr
1940                1945                    1950

Ser Ser Asn Ala Val Phe Asn Thr Lys Ser Ser Tyr Tyr Thr Leu
1955                1960                    1965

Leu Phe Asn Leu Ile Gln Asn Gly Ser Ile Glu Met Lys Tyr Gln
1970                1975                    1980

Ile Ile Leu Ser Ile Val Glu Gln Leu Arg Tyr Pro Asn Ile His
1985                1990                    1995

Thr Tyr Trp Phe Ser Phe Val Leu Met Asn Met Phe Lys Ser Asp
2000                2005                    2010

Glu Trp Asn Asp Gln Lys Leu Glu Val Gln Glu Ile Ile Leu Arg
2015                2020                    2025

Asn Phe Leu Lys Arg Ile Ile Val Asn Lys Pro His Thr Trp Gly
2030                2035                    2040

Val Ser Val Phe Phe Thr Gln Leu Ile Asn Asn Asp Ile Asn
2045                2050                    2055

Leu Leu Asp Leu Pro Phe Val Gln Ser Val Pro Glu Ile Lys Leu
2060                2065                    2070

Ile Leu Gln Gln Leu Val Lys Tyr Ser Lys Tyr Thr Thr Ser
2075                2080                    2085

Glu Gln Asp Asp Gln Ser Ala Thr Ile Asn Arg Arg Gln Thr Pro
2090                2095                    2100

Leu Gln Ser Asn Ala
    2105

<210> SEQ ID NO 14
<211> LENGTH: 31
<212> TYPE: PRT
<213> ORGANISM: Artificial Sequence
<220> FEATURE:
<223> OTHER INFORMATION: GLP-1 fragment

<400> SEQUENCE: 14

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 15
<211> LENGTH: 61
<212> TYPE: PRT
<213> ORGANISM: Artificial Sequence
<220> FEATURE:
<223> OTHER INFORMATION: Tandem repeat of GLP-1 fragment

<400> SEQUENCE: 15

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
                35                  40                  45

Ala Lys Glu Phe Ile Ala Trp Leu Val Lys Gly Arg Gly
    50                  55                  60

<210> SEQ ID NO 16
<211> LENGTH: 645
<212> TYPE: PRT
<213> ORGANISM: Artificial Sequence
<220> FEATURE:
<223> OTHER INFORMATION: Albiglutide (GLP-1 tandem repeat fused to the
      N-terminus of human serum albumin)

<400> SEQUENCE: 16

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
                35                  40                  45

Ala Lys Glu Phe Ile Ala Trp Leu Val Lys Gly Arg Asp Ala His Lys
    50                  55                  60

Ser Glu Val Ala His Arg Phe Lys Asp Leu Gly Glu Glu Asn Phe Lys
65                  70                  75                  80

Ala Leu Val Leu Ile Ala Phe Ala Gln Tyr Leu Gln Gln Cys Pro Phe
                85                  90                  95

Glu Asp His Val Lys Leu Val Asn Glu Val Thr Glu Phe Ala Lys Thr
                100                 105                 110

Cys Val Ala Asp Glu Ser Ala Glu Asn Cys Asp Lys Ser Leu His Thr
            115                 120                 125

Leu Phe Gly Asp Lys Leu Cys Thr Val Ala Thr Leu Arg Glu Thr Tyr
130                 135                 140

Gly Glu Met Ala Asp Cys Cys Ala Lys Gln Glu Pro Glu Arg Asn Glu
145                 150                 155                 160

Cys Phe Leu Gln His Lys Asp Asp Asn Pro Asn Leu Pro Arg Leu Val
                165                 170                 175

Arg Pro Glu Val Asp Val Met Cys Thr Ala Phe His Asp Asn Glu Glu
                180                 185                 190

Thr Phe Leu Lys Lys Tyr Leu Tyr Glu Ile Ala Arg Arg His Pro Tyr
            195                 200                 205

```
Phe Tyr Ala Pro Glu Leu Leu Phe Phe Ala Lys Arg Tyr Lys Ala Ala
210                 215                 220

Phe Thr Glu Cys Cys Gln Ala Ala Asp Lys Ala Ala Cys Leu Leu Pro
225                 230                 235                 240

Lys Leu Asp Glu Leu Arg Asp Glu Gly Lys Ala Ser Ser Ala Lys Gln
            245                 250                 255

Arg Leu Lys Cys Ala Ser Leu Gln Lys Phe Gly Glu Arg Ala Phe Lys
        260                 265                 270

Ala Trp Ala Val Ala Arg Leu Ser Gln Arg Phe Pro Lys Ala Glu Phe
    275                 280                 285

Ala Glu Val Ser Lys Leu Val Thr Asp Leu Thr Lys Val His Thr Glu
290                 295                 300

Cys Cys His Gly Asp Leu Leu Glu Cys Ala Asp Asp Arg Ala Asp Leu
305                 310                 315                 320

Ala Lys Tyr Ile Cys Glu Asn Gln Asp Ser Ile Ser Ser Lys Leu Lys
            325                 330                 335

Glu Cys Cys Glu Lys Pro Leu Leu Glu Lys Ser His Cys Ile Ala Glu
        340                 345                 350

Val Glu Asn Asp Glu Met Pro Ala Asp Leu Pro Ser Leu Ala Ala Asp
    355                 360                 365

Phe Val Glu Ser Lys Asp Val Cys Lys Asn Tyr Ala Glu Ala Lys Asp
370                 375                 380

Val Phe Leu Gly Met Phe Leu Tyr Glu Tyr Ala Arg Arg His Pro Asp
385                 390                 395                 400

Tyr Ser Val Val Leu Leu Leu Arg Leu Ala Lys Thr Tyr Glu Thr Thr
            405                 410                 415

Leu Glu Lys Cys Cys Ala Ala Ala Asp Pro His Glu Cys Tyr Ala Lys
        420                 425                 430

Val Phe Asp Glu Phe Lys Pro Leu Val Glu Glu Pro Gln Asn Leu Ile
    435                 440                 445

Lys Gln Asn Cys Glu Leu Phe Glu Gln Leu Gly Glu Tyr Lys Phe Gln
450                 455                 460

Asn Ala Leu Leu Val Arg Tyr Thr Lys Lys Val Pro Gln Val Ser Thr
465                 470                 475                 480

Pro Thr Leu Val Glu Val Ser Arg Asn Leu Gly Lys Val Gly Ser Lys
            485                 490                 495

Cys Cys Lys His Pro Glu Ala Lys Arg Met Pro Cys Ala Glu Asp Tyr
        500                 505                 510

Leu Ser Val Val Leu Asn Gln Leu Cys Val Leu His Glu Lys Thr Pro
    515                 520                 525

Val Ser Asp Arg Val Thr Lys Cys Cys Thr Glu Ser Leu Val Asn Arg
530                 535                 540

Arg Pro Cys Phe Ser Ala Leu Glu Val Asp Glu Thr Tyr Val Pro Lys
545                 550                 555                 560

Glu Phe Asn Ala Glu Thr Phe Thr Phe His Ala Asp Ile Cys Thr Leu
            565                 570                 575

Ser Glu Lys Glu Arg Gln Ile Lys Lys Gln Thr Ala Leu Val Glu Leu
        580                 585                 590

Val Lys His Lys Pro Lys Ala Thr Lys Glu Gln Leu Lys Ala Val Met
    595                 600                 605

Asp Asp Phe Ala Ala Phe Val Glu Lys Cys Cys Lys Ala Asp Asp Lys
610                 615                 620

Glu Thr Cys Phe Ala Glu Glu Gly Lys Lys Leu Val Ala Ala Ser Gln
```

```
                625                 630                 635                 640

Ala Ala Leu Gly Leu
                645

<210> SEQ ID NO 17
<211> LENGTH: 24
<212> TYPE: PRT
<213> ORGANISM: Artificial Sequence
<220> FEATURE:
<223> OTHER INFORMATION: KEX leader sequence

<400> SEQUENCE: 17

Met Lys Trp Val Ser Phe Ile Ser Leu Leu Phe Leu Phe Ser Ser Ala
1               5                   10                  15

Tyr Ser Arg Ser Leu Asp Lys Arg
            20

<210> SEQ ID NO 18
<211> LENGTH: 24
<212> TYPE: PRT
<213> ORGANISM: Artificial Sequence
<220> FEATURE:
<223> OTHER INFORMATION: Modified KEX leader sequence

<400> SEQUENCE: 18

Met Lys Trp Val Ser Phe Ile Ser Leu Leu Phe Leu Phe Ser Ser Ala
1               5                   10                  15

Tyr Ser Gly Ser Leu Asp Lys Arg
            20

<210> SEQ ID NO 19
<211> LENGTH: 27
<212> TYPE: PRT
<213> ORGANISM: Artificial Sequence
<220> FEATURE:
<223> OTHER INFORMATION: Mating factor alpha - Human serum albumin
      fusion leader sequence

<400> SEQUENCE: 19

Met Lys Trp Val Ser Phe Ile Ser Leu Leu Phe Leu Phe Ser Ser Ala
1               5                   10                  15

Tyr Ser Arg Ser Leu Asp Lys Arg Asp Ala His
            20                  25

<210> SEQ ID NO 20
<211> LENGTH: 5
<212> TYPE: PRT
<213> ORGANISM: Artificial Sequence
<220> FEATURE:
<223> OTHER INFORMATION: Pentapeptide motif
<220> FEATURE:
<221> NAME/KEY: MISC_FEATURE
<222> LOCATION: (1)..(1)
<223> OTHER INFORMATION: Xaa = Phe, Trp or Tyr
<220> FEATURE:
<221> NAME/KEY: MISC_FEATURE
<222> LOCATION: (2)..(2)
<223> OTHER INFORMATION: Xaa = Ile, Leu, Val, Ala or Met
<220> FEATURE:
<221> NAME/KEY: MISC_FEATURE
<222> LOCATION: (3)..(3)
<223> OTHER INFORMATION: Xaa = Leu, Val, Ala or Met
<220> FEATURE:
<221> NAME/KEY: MISC_FEATURE
<222> LOCATION: (4)..(4)
<223> OTHER INFORMATION: Xaa = Ser or Thr
<220> FEATURE:
<221> NAME/KEY: MISC_FEATURE
```

```
<222> LOCATION: (5)..(5)
<223> OTHER INFORMATION: Xaa = Ile, Val, Ala or Met

<400> SEQUENCE: 20

Xaa Xaa Xaa Xaa Xaa
1               5

<210> SEQ ID NO 21
<211> LENGTH: 19
<212> TYPE: PRT
<213> ORGANISM: Artificial Sequence
<220> FEATURE:
<223> OTHER INFORMATION: Leader Sequence
<220> FEATURE:
<221> NAME/KEY: MISC_FEATURE
<222> LOCATION: (5)..(5)
<223> OTHER INFORMATION: Xaa = Phe, Trp or Tyr
<220> FEATURE:
<221> NAME/KEY: MISC_FEATURE
<222> LOCATION: (6)..(6)
<223> OTHER INFORMATION: Xaa = Ile, Leu, Val, Ala or Met
<220> FEATURE:
<221> NAME/KEY: MISC_FEATURE
<222> LOCATION: (7)..(7)
<223> OTHER INFORMATION: Xaa = Leu, Val, Ala or Met
<220> FEATURE:
<221> NAME/KEY: MISC_FEATURE
<222> LOCATION: (8)..(8)
<223> OTHER INFORMATION: Xaa = Ser or Thr
<220> FEATURE:
<221> NAME/KEY: MISC_FEATURE
<222> LOCATION: (9)..(9)
<223> OTHER INFORMATION: Xaa = Ile, Val, Ala or Met

<400> SEQUENCE: 21

Met Lys Trp Val Xaa Xaa Xaa Xaa Xaa Leu Phe Leu Phe Ser Ser Ala
1               5                   10                  15

Tyr Ser Arg

<210> SEQ ID NO 22
<211> LENGTH: 24
<212> TYPE: PRT
<213> ORGANISM: Artificial Sequence
<220> FEATURE:
<223> OTHER INFORMATION: Leader Sequence
<220> FEATURE:
<221> NAME/KEY: MISC_FEATURE
<222> LOCATION: (5)..(5)
<223> OTHER INFORMATION: Xaa = Phe, Trp or Tyr
<220> FEATURE:
<221> NAME/KEY: MISC_FEATURE
<222> LOCATION: (6)..(6)
<223> OTHER INFORMATION: Xaa = Ile, Leu, Val, Ala or Met
<220> FEATURE:
<221> NAME/KEY: MISC_FEATURE
<222> LOCATION: (7)..(7)
<223> OTHER INFORMATION: Xaa = Leu, Val, Ala or Met
<220> FEATURE:
<221> NAME/KEY: MISC_FEATURE
<222> LOCATION: (8)..(8)
<223> OTHER INFORMATION: Xaa = Ser or Thr
<220> FEATURE:
<221> NAME/KEY: MISC_FEATURE
<222> LOCATION: (9)..(9)
<223> OTHER INFORMATION: Xaa = Ile, Val, Ala or Met
<220> FEATURE:
<221> NAME/KEY: PROPEP
<222> LOCATION: (20)..(24)
<220> FEATURE:
<221> NAME/KEY: MISC_FEATURE
<222> LOCATION: (20)..(20)
<223> OTHER INFORMATION: Xaa = Gly or Ser
<220> FEATURE:
<221> NAME/KEY: MISC_FEATURE
```

```
<222> LOCATION: (21)..(21)
<223> OTHER INFORMATION: Xaa = Val or Leu
<220> FEATURE:
<221> NAME/KEY: MISC_FEATURE
<222> LOCATION: (22)..(22)
<223> OTHER INFORMATION: Xaa = Phe or Asp
<220> FEATURE:
<221> NAME/KEY: MISC_FEATURE
<222> LOCATION: (23)..(23)
<223> OTHER INFORMATION: Xaa = Arg or Lys
<220> FEATURE:
<221> NAME/KEY: MISC_FEATURE
<222> LOCATION: (24)..(24)
<223> OTHER INFORMATION: Xaa = Arg or Lys

<400> SEQUENCE: 22

Met Lys Trp Val Xaa Xaa Xaa Xaa Xaa Leu Phe Leu Phe Ser Ser Ala
1               5                   10                  15

Tyr Ser Arg Xaa Xaa Xaa Xaa Xaa
            20

<210> SEQ ID NO 23
<211> LENGTH: 24
<212> TYPE: PRT
<213> ORGANISM: Artificial Sequence
<220> FEATURE:
<223> OTHER INFORMATION: Leader sequence
<220> FEATURE:
<221> NAME/KEY: SIGNAL
<222> LOCATION: (1)..(19)
<223> OTHER INFORMATION: Pre sequence
<220> FEATURE:
<221> NAME/KEY: PROPEP
<222> LOCATION: (20)..(24)
<220> FEATURE:
<221> NAME/KEY: MISC_FEATURE
<222> LOCATION: (20)..(20)
<223> OTHER INFORMATION: Xaa = Gly or Ser
<220> FEATURE:
<221> NAME/KEY: MISC_FEATURE
<222> LOCATION: (21)..(21)
<223> OTHER INFORMATION: Xaa = Val or Leu
<220> FEATURE:
<221> NAME/KEY: MISC_FEATURE
<222> LOCATION: (22)..(22)
<223> OTHER INFORMATION: Xaa = Phe or Asp
<220> FEATURE:
<221> NAME/KEY: MISC_FEATURE
<222> LOCATION: (23)..(23)
<223> OTHER INFORMATION: Xaa = Arg or Lys
<220> FEATURE:
<221> NAME/KEY: MISC_FEATURE
<222> LOCATION: (24)..(24)
<223> OTHER INFORMATION: Xaa = Arg or Lys

<400> SEQUENCE: 23

Met Lys Trp Val Phe Ile Val Ser Ile Leu Phe Leu Phe Ser Ser Ala
1               5                   10                  15

Tyr Ser Arg Xaa Xaa Xaa Xaa Xaa
            20

<210> SEQ ID NO 24
<211> LENGTH: 24
<212> TYPE: PRT
<213> ORGANISM: Artificial Sequence
<220> FEATURE:
<223> OTHER INFORMATION: Leader sequence

<400> SEQUENCE: 24

Met Lys Trp Val Phe Ile Val Ser Ile Leu Phe Leu Phe Ser Ser Ala
1               5                   10                  15
```

<210> SEQ ID NO 25
<211> LENGTH: 522
<212> TYPE: PRT
<213> ORGANISM: Saccharomyces cerevisiae

<400> SEQUENCE: 25

Met Lys Phe Ser Ala Gly Ala Val Leu Ser Trp Ser Ser Leu Leu Leu
1               5                   10                  15

Ala Ser Ser Val Phe Ala Gln Gln Glu Ala Val Ala Pro Glu Asp Ser
            20                  25                  30

Ala Val Val Lys Leu Ala Thr Asp Ser Phe Asn Glu Tyr Ile Gln Ser
        35                  40                  45

His Asp Leu Val Leu Ala Glu Phe Phe Ala Pro Trp Cys Gly His Cys
    50                  55                  60

Lys Asn Met Ala Pro Glu Tyr Val Lys Ala Ala Glu Thr Leu Val Glu
65                  70                  75                  80

Lys Asn Ile Thr Leu Ala Gln Ile Asp Cys Thr Glu Asn Gln Asp Leu
                85                  90                  95

Cys Met Glu His Asn Ile Pro Gly Phe Pro Ser Leu Lys Ile Phe Lys
            100                 105                 110

Asn Ser Asp Val Asn Asn Ser Ile Asp Tyr Glu Gly Pro Arg Thr Ala
        115                 120                 125

Glu Ala Ile Val Gln Phe Met Ile Lys Gln Ser Gln Pro Ala Val Ala
    130                 135                 140

Val Val Ala Asp Leu Pro Ala Tyr Leu Ala Asn Glu Thr Phe Val Thr
145                 150                 155                 160

Pro Val Ile Val Gln Ser Gly Lys Ile Asp Ala Asp Phe Asn Ala Thr
                165                 170                 175

Phe Tyr Ser Met Ala Asn Lys His Phe Asn Asp Tyr Asp Phe Val Ser
            180                 185                 190

Ala Glu Asn Ala Asp Asp Phe Lys Leu Ser Ile Tyr Leu Pro Ser
        195                 200                 205

Ala Met Asp Glu Pro Val Val Tyr Asn Gly Lys Lys Ala Asp Ile Ala
    210                 215                 220

Asp Ala Asp Val Phe Glu Lys Trp Leu Gln Val Glu Ala Leu Pro Tyr
225                 230                 235                 240

Phe Gly Glu Ile Asp Gly Ser Val Phe Ala Gln Tyr Val Glu Ser Gly
                245                 250                 255

Leu Pro Leu Gly Tyr Leu Phe Tyr Asn Asp Glu Glu Leu Glu Glu
            260                 265                 270

Tyr Lys Pro Leu Phe Thr Glu Leu Ala Lys Lys Asn Arg Gly Leu Met
        275                 280                 285

Asn Phe Val Ser Ile Asp Ala Arg Lys Phe Gly Arg His Ala Gly Asn
    290                 295                 300

Leu Asn Met Lys Glu Gln Phe Pro Leu Phe Ala Ile His Asp Met Thr
305                 310                 315                 320

Glu Asp Leu Lys Tyr Gly Leu Pro Gln Leu Ser Glu Glu Ala Phe Asp
                325                 330                 335

Glu Leu Ser Asp Lys Ile Val Leu Glu Ser Lys Ala Ile Glu Ser Leu
            340                 345                 350

Val Lys Asp Phe Leu Lys Gly Asp Ala Ser Pro Ile Val Lys Ser Gln
        355                 360                 365

Glu Ile Phe Glu Asn Gln Asp Ser Ser Val Phe Gln Leu Val Gly Lys
    370                 375                 380

Asn His Asp Glu Ile Val Asn Asp Pro Lys Lys Asp Val Leu Val Leu
385                 390                 395                 400

Tyr Tyr Ala Pro Trp Cys Gly His Cys Lys Arg Leu Ala Pro Thr Tyr
                405                 410                 415

Gln Glu Leu Ala Asp Thr Tyr Ala Asn Ala Thr Ser Asp Val Leu Ile
            420                 425                 430

Ala Lys Leu Asp His Thr Glu Asn Asp Val Arg Gly Val Val Ile Glu
        435                 440                 445

Gly Tyr Pro Thr Ile Val Leu Tyr Pro Gly Gly Lys Lys Ser Glu Ser
    450                 455                 460

Val Val Tyr Gln Gly Ser Arg Ser Leu Asp Ser Leu Phe Asp Phe Ile
465                 470                 475                 480

Lys Glu Asn Gly His Phe Asp Val Asp Gly Lys Ala Leu Tyr Glu Glu
                485                 490                 495

Ala Gln Glu Lys Ala Ala Glu Ala Asp Ala Asp Ala Glu Leu Ala
            500                 505                 510

Asp Glu Glu Asp Ala Ile His Asp Glu Leu
        515                 520

<210> SEQ ID NO 26
<211> LENGTH: 563
<212> TYPE: PRT
<213> ORGANISM: Saccharomyces cerevisiae

<400> SEQUENCE: 26

Met Arg Leu Arg Thr Ala Ile Ala Thr Leu Cys Leu Thr Ala Phe Thr
1               5                   10                  15

Ser Ala Thr Ser Asn Asn Ser Tyr Ile Ala Thr Asp Gln Thr Gln Asn
            20                  25                  30

Ala Phe Asn Asp Thr His Phe Cys Lys Val Asp Arg Asn Asp His Val
        35                  40                  45

Ser Pro Ser Cys Asn Val Thr Phe Asn Glu Leu Asn Ala Ile Asn Glu
    50                  55                  60

Asn Ile Arg Asp Asp Leu Ser Ala Leu Leu Lys Ser Asp Phe Phe Lys
65                  70                  75                  80

Tyr Phe Arg Leu Asp Leu Tyr Lys Gln Cys Ser Phe Trp Asp Ala Asn
                85                  90                  95

Asp Gly Leu Cys Leu Asn Arg Ala Cys Ser Val Asp Val Val Glu Asp
            100                 105                 110

Trp Asp Thr Leu Pro Glu Tyr Trp Gln Pro Glu Ile Leu Gly Ser Phe
        115                 120                 125

Asn Asn Asp Thr Met Lys Glu Ala Asp Ser Asp Asp Glu Cys Lys
    130                 135                 140

Phe Leu Asp Gln Leu Cys Gln Thr Ser Lys Lys Pro Val Asp Ile Glu
145                 150                 155                 160

Asp Thr Ile Asn Tyr Cys Asp Val Asn Asp Phe Asn Gly Lys Asn Ala
                165                 170                 175

Val Leu Ile Asp Leu Thr Ala Asn Pro Glu Arg Phe Thr Gly Tyr Gly
            180                 185                 190

Gly Lys Gln Ala Gly Gln Ile Trp Ser Thr Ile Tyr Gln Asp Asn Cys
        195                 200                 205

Phe Thr Ile Gly Glu Thr Gly Glu Ser Leu Ala Lys Asp Ala Phe Tyr

```
                210               215                 220
Arg Leu Val Ser Gly Phe His Ala Ser Ile Gly Thr His Leu Ser Lys
225                 230                 235                 240

Glu Tyr Leu Asn Thr Lys Thr Gly Lys Trp Glu Pro Asn Leu Asp Leu
                245                 250                 255

Phe Met Ala Arg Ile Gly Asn Phe Pro Asp Arg Val Thr Asn Met Tyr
                260                 265                 270

Phe Asn Tyr Ala Val Val Ala Lys Ala Leu Trp Lys Ile Gln Pro Tyr
                275                 280                 285

Leu Pro Glu Phe Ser Phe Cys Asp Leu Val Asn Lys Glu Ile Lys Asn
290                 295                 300

Lys Met Asp Asn Val Ile Ser Gln Leu Asp Thr Lys Ile Phe Asn Glu
305                 310                 315                 320

Asp Leu Val Phe Ala Asn Asp Leu Ser Leu Thr Leu Lys Asp Glu Phe
                325                 330                 335

Arg Ser Arg Phe Lys Asn Val Thr Lys Ile Met Asp Cys Val Gln Cys
                340                 345                 350

Asp Arg Cys Arg Leu Trp Gly Lys Ile Gln Thr Thr Gly Tyr Ala Thr
                355                 360                 365

Ala Leu Lys Ile Leu Phe Glu Ile Asn Asp Ala Asp Glu Phe Thr Lys
370                 375                 380

Gln His Ile Val Gly Lys Leu Thr Lys Tyr Glu Leu Ile Ala Leu Leu
385                 390                 395                 400

Gln Thr Phe Gly Arg Leu Ser Glu Ser Ile Glu Ser Val Asn Met Phe
                405                 410                 415

Glu Lys Met Tyr Gly Lys Arg Leu Asn Gly Ser Glu Asn Arg Leu Ser
                420                 425                 430

Ser Phe Phe Gln Asn Asn Phe Phe Asn Ile Leu Lys Glu Ala Gly Lys
                435                 440                 445

Ser Ile Arg Tyr Thr Ile Glu Asn Ile Asn Ser Thr Lys Glu Gly Lys
                450                 455                 460

Lys Lys Thr Asn Asn Ser Gln Ser His Val Phe Asp Asp Leu Lys Met
465                 470                 475                 480

Pro Lys Ala Glu Ile Val Pro Arg Pro Ser Asn Gly Thr Val Asn Lys
                485                 490                 495

Trp Lys Lys Ala Trp Asn Thr Glu Val Asn Val Leu Glu Ala Phe
                500                 505                 510

Arg Phe Ile Tyr Arg Ser Tyr Leu Asp Leu Pro Arg Asn Ile Trp Glu
                515                 520                 525

Leu Ser Leu Met Lys Val Tyr Lys Phe Trp Asn Lys Phe Ile Gly Val
530                 535                 540

Ala Asp Tyr Val Ser Glu Glu Thr Arg Glu Pro Ile Ser Tyr Lys Leu
545                 550                 555                 560

Asp Ile Gln
```

<210> SEQ ID NO 27
<211> LENGTH: 2445
<212> TYPE: DNA
<213> ORGANISM: Saccharomyces cerevisiae

<400> SEQUENCE: 27
atgaaagtga ggaaatatat tactttatgc ttttggtggg cctttcaac atccgctctt      60 gtatcatcac aacaaattcc attgaaggac catacgtcac gacagtattt tgctgtagaa    120

```
agcaatgaaa cattatcccg cttggaggaa atgcatccaa attggaaata tgaacatgat      180
gttcgagggc taccaaacca ttatgttttt tcaaaagagt tgctaaaatt gggcaaaaga      240
tcatcattag aagagttaca gggggataac aacgaccaca tattatctgt ccatgattta      300
ttcccgcgta acgacctatt taagagacta ccggtgcctg ctccaccaat ggactcaagc      360
ttgttaccgg taaaagaagc tgaggataaa ctcagcataa atgatccgct ttttgagagg      420
cagtggcact tggtcaatcc aagttttcct ggcagtgata taaatgttct tgatctgtgg      480
tacaataata ttacaggcgc aggggtcgtg gctgccattg ttgatgatgg ccttgactac      540
gaaaatgaag acttgaagga taattttgc gctgaaggtt cttgggattt caacgacaat       600
accaatttac ctaaaccaag attatctgat gactaccatg gtacgagatg tgcaggtgaa      660
atagctgcca aaaaggtaa caatttttgc ggtgtcgggg taggttacaa cgctaaaatc       720
tcaggcataa gaatcttatc cggtgatatc actacggaag atgaagctgc gtccttgatt      780
tatggtctag acgtaaacga tatatattca tgctcatggg gtcccgctga tgacggaaga      840
catttacaag gccctagtga cctggtgaaa aaggctttag taaaaggtgt tactgaggga      900
agagattcca aaggagcgat ttacgttttt gccagtggaa atggtggaac tcgtggtgat      960
aattgcaatt acgacggcta tactaattcc atatattcta ttactattgg ggctattgat     1020
cacaaagatc tacatcctcc ttattccgaa ggttgttccg ccgtcatggc agtcacgtat     1080
tcttcaggtt caggcgaata tattcattcg agtgatatca acggcagatg cagtaatagc     1140
cacggtggaa cgtctgcggc tgctccatta gctgccggtg tttacacttt gttactagaa     1200
gccaacccaa acctaacttg gagagacgta cagtatttat caatcttgtc tgcggtaggg     1260
ttagaaaaga acgctgacgg agattggaga gatagcgcca tggggaagaa atactctcat     1320
cgctatggct ttggtaaaat cgatgcccat aagttaattg aaatgtccaa gacctgggag     1380
aatgttaacg cacaaacctg gttttacctg ccaacattgt atgtttccca gtccacaaac     1440
tccacggaag agacattaga atccgtcata accatatcag aaaaaagtct tcaagatgct     1500
aacttcaaga gaattgagca cgtcacggta actgtagata ttgatacaga aattagggga     1560
actacgactg tcgatttaat atcaccagcg gggataattt caaaccttgg cgttgtaaga     1620
ccaagagatg tttcatcaga gggattcaaa gactggacat tcatgtctgt agcacattgg     1680
ggtgagaacg gcgtaggtga ttggaaaatc aaggttaaga caacagaaaa tggacacagg     1740
attgacttcc acagttggag gctgaagctc tttggggaat ccattgattc atctaaaaca     1800
gaaactttcg tctttggaaa cgataaagag gaggttgaac cagctgctac agaaagtacc     1860
gtatcacaat attctgccag ttcaacttct atttccatca gcgctacttc tacatcttct     1920
atctcaattg gtgtggaaac gtcggccatt ccccaaacga ctactgcgag taccgatcct     1980
gattctgatc caaacactcc taaaaaactt tcctctccta ggcaagccat gcattatttt     2040
ttaacaatat ttttgattgg cgccacattt ttggtgttat acttcatgtt ttttatgaaa     2100
tcaaggagaa ggatcagaag gtcaagagcg gaaacgtatg aattcgatat cattgataca     2160
gactctgagt acgattctac tttggacaat ggaacttccg gaattactga gcccgaagag     2220
gttgaggact tcgattttga tttgtccgat gaagaccatc ttgcaagttt gtcttcatca     2280
gaaaacggtg atgctgaaca tacaattgat agtgtactaa caaacgaaaa tccatttagt     2340
gaccctataa agcaaaagtt cccaaatgac gccaacgcag aatctgcttc caataaatta     2400
caagaattac agcctgatgt tcctccatct tccggacgat cgtga                     2445
```

-continued

```
<210> SEQ ID NO 28
<211> LENGTH: 814
<212> TYPE: PRT
<213> ORGANISM: Saccharomyces cerevisiae

<400> SEQUENCE: 28
```

| | | | | | | | | | | | | | | | |
|---|---|---|---|---|---|---|---|---|---|---|---|---|---|---|---|
| Met | Lys | Val | Arg | Lys | Tyr | Ile | Thr | Leu | Cys | Phe | Trp | Trp | Ala | Phe | Ser |
| 1 | | | | 5 | | | | | 10 | | | | | 15 | |
| Thr | Ser | Ala | Leu | Val | Ser | Ser | Gln | Gln | Ile | Pro | Leu | Lys | Asp | His | Thr |
| | | | 20 | | | | | 25 | | | | | 30 | | |
| Ser | Arg | Gln | Tyr | Phe | Ala | Val | Glu | Ser | Asn | Glu | Thr | Leu | Ser | Arg | Leu |
| | | | 35 | | | | 40 | | | | | 45 | | | |
| Glu | Glu | Met | His | Pro | Asn | Trp | Lys | Tyr | Glu | His | Asp | Val | Arg | Gly | Leu |
| | 50 | | | | | 55 | | | | | 60 | | | | |
| Pro | Asn | His | Tyr | Val | Phe | Ser | Lys | Glu | Leu | Leu | Lys | Leu | Gly | Lys | Arg |
| 65 | | | | | 70 | | | | | 75 | | | | | 80 |
| Ser | Ser | Leu | Glu | Glu | Leu | Gln | Gly | Asp | Asn | Asn | Asp | His | Ile | Leu | Ser |
| | | | | 85 | | | | | 90 | | | | | 95 | |
| Val | His | Asp | Leu | Phe | Pro | Arg | Asn | Asp | Leu | Phe | Lys | Arg | Leu | Pro | Val |
| | | | 100 | | | | | 105 | | | | | 110 | | |
| Pro | Ala | Pro | Pro | Met | Asp | Ser | Ser | Leu | Leu | Pro | Val | Lys | Glu | Ala | Glu |
| | | | 115 | | | | | 120 | | | | | 125 | | |
| Asp | Lys | Leu | Ser | Ile | Asn | Asp | Pro | Leu | Phe | Glu | Arg | Gln | Trp | His | Leu |
| | 130 | | | | | 135 | | | | | 140 | | | | |
| Val | Asn | Pro | Ser | Phe | Pro | Gly | Ser | Asp | Ile | Asn | Val | Leu | Asp | Leu | Trp |
| 145 | | | | | 150 | | | | | 155 | | | | | 160 |
| Tyr | Asn | Asn | Ile | Thr | Gly | Ala | Gly | Val | Val | Ala | Ile | Val | Asp | Asp |
| | | | | 165 | | | | | 170 | | | | | 175 | |
| Gly | Leu | Asp | Tyr | Glu | Asn | Glu | Asp | Leu | Lys | Asp | Asn | Phe | Cys | Ala | Glu |
| | | | 180 | | | | | 185 | | | | | 190 | | |
| Gly | Ser | Trp | Asp | Phe | Asn | Asp | Asn | Thr | Asn | Leu | Pro | Lys | Pro | Arg | Leu |
| | | | 195 | | | | | 200 | | | | | 205 | | |
| Ser | Asp | Asp | Tyr | His | Gly | Thr | Arg | Cys | Ala | Gly | Glu | Ile | Ala | Ala | Lys |
| | 210 | | | | | 215 | | | | | 220 | | | | |
| Lys | Gly | Asn | Asn | Phe | Cys | Gly | Val | Gly | Val | Gly | Tyr | Asn | Ala | Lys | Ile |
| 225 | | | | | 230 | | | | | 235 | | | | | 240 |
| Ser | Gly | Ile | Arg | Ile | Leu | Ser | Gly | Asp | Ile | Thr | Thr | Glu | Asp | Glu | Ala |
| | | | | 245 | | | | | 250 | | | | | 255 | |
| Ala | Ser | Leu | Ile | Tyr | Gly | Leu | Asp | Val | Asn | Asp | Ile | Tyr | Ser | Cys | Ser |
| | | | 260 | | | | | 265 | | | | | 270 | | |
| Trp | Gly | Pro | Ala | Asp | Asp | Gly | Arg | His | Leu | Gln | Gly | Pro | Ser | Asp | Leu |
| | | | 275 | | | | | 280 | | | | | 285 | | |
| Val | Lys | Lys | Ala | Leu | Val | Lys | Gly | Val | Thr | Glu | Gly | Arg | Asp | Ser | Lys |
| | 290 | | | | | 295 | | | | | 300 | | | | |
| Gly | Ala | Ile | Tyr | Val | Phe | Ala | Ser | Gly | Asn | Gly | Gly | Thr | Arg | Gly | Asp |
| 305 | | | | | 310 | | | | | 315 | | | | | 320 |
| Asn | Cys | Asn | Tyr | Asp | Gly | Tyr | Thr | Asn | Ser | Ile | Tyr | Ser | Ile | Thr | Ile |
| | | | | 325 | | | | | 330 | | | | | 335 | |
| Gly | Ala | Ile | Asp | His | Lys | Asp | Leu | His | Pro | Pro | Tyr | Ser | Glu | Gly | Cys |
| | | | 340 | | | | | 345 | | | | | 350 | | |
| Ser | Ala | Val | Met | Ala | Val | Thr | Tyr | Ser | Ser | Gly | Ser | Gly | Glu | Tyr | Ile |
| | | | 355 | | | | | 360 | | | | | 365 | | |
| His | Ser | Ser | Asp | Ile | Asn | Gly | Arg | Cys | Ser | Asn | Ser | His | Gly | Gly | Thr |
| | 370 | | | | | 375 | | | | | 380 | | | | |

```
Ser Ala Ala Ala Pro Leu Ala Gly Val Tyr Thr Leu Leu Glu
385                 390                 395                 400

Ala Asn Pro Asn Leu Thr Trp Arg Asp Val Gln Tyr Leu Ser Ile Leu
                405                 410                 415

Ser Ala Val Gly Leu Glu Lys Asn Ala Asp Gly Asp Trp Arg Asp Ser
            420                 425                 430

Ala Met Gly Lys Lys Tyr Ser His Arg Tyr Gly Phe Gly Lys Ile Asp
        435                 440                 445

Ala His Lys Leu Ile Glu Met Ser Lys Thr Trp Glu Asn Val Asn Ala
    450                 455                 460

Gln Thr Trp Phe Tyr Leu Pro Thr Leu Tyr Val Ser Gln Ser Thr Asn
465                 470                 475                 480

Ser Thr Glu Glu Thr Leu Glu Ser Val Ile Thr Ile Ser Glu Lys Ser
                485                 490                 495

Leu Gln Asp Ala Asn Phe Lys Arg Ile Glu His Val Thr Val Thr Val
                500                 505                 510

Asp Ile Asp Thr Glu Ile Arg Gly Thr Thr Thr Val Asp Leu Ile Ser
            515                 520                 525

Pro Ala Gly Ile Ile Ser Asn Leu Gly Val Val Arg Pro Arg Asp Val
        530                 535                 540

Ser Ser Glu Gly Phe Lys Asp Trp Thr Phe Met Ser Val Ala His Trp
545                 550                 555                 560

Gly Glu Asn Gly Val Gly Asp Trp Lys Ile Lys Val Lys Thr Thr Glu
                565                 570                 575

Asn Gly His Arg Ile Asp Phe His Ser Trp Arg Leu Lys Leu Phe Gly
            580                 585                 590

Glu Ser Ile Asp Ser Ser Lys Thr Glu Thr Phe Val Phe Gly Asn Asp
        595                 600                 605

Lys Glu Glu Val Glu Pro Ala Ala Thr Glu Ser Thr Val Ser Gln Tyr
    610                 615                 620

Ser Ala Ser Ser Thr Ser Ile Ser Ile Ser Ala Thr Ser Thr Ser Ser
625                 630                 635                 640

Ile Ser Ile Gly Val Glu Thr Ser Ala Ile Pro Gln Thr Thr Thr Ala
                645                 650                 655

Ser Thr Asp Pro Asp Ser Asp Pro Asn Thr Pro Lys Lys Leu Ser Ser
            660                 665                 670

Pro Arg Gln Ala Met His Tyr Phe Leu Thr Ile Phe Leu Ile Gly Ala
        675                 680                 685

Thr Phe Leu Val Leu Tyr Phe Met Phe Met Lys Ser Arg Arg Arg
690                 695                 700

Ile Arg Arg Ser Arg Ala Glu Thr Tyr Glu Phe Asp Ile Ile Asp Thr
705                 710                 715                 720

Asp Ser Glu Tyr Asp Ser Thr Leu Asp Asn Gly Thr Ser Gly Ile Thr
                725                 730                 735

Glu Pro Glu Glu Val Asp Phe Asp Phe Asp Leu Ser Asp Glu Asp
            740                 745                 750

His Leu Ala Ser Leu Ser Ser Glu Asn Gly Asp Ala Glu His Thr
        755                 760                 765

Ile Asp Ser Val Leu Thr Asn Glu Asn Pro Phe Ser Asp Pro Ile Lys
    770                 775                 780

Gln Lys Phe Pro Asn Asp Ala Asn Ala Glu Ser Ala Ser Asn Lys Leu
785                 790                 795                 800

Gln Glu Leu Gln Pro Asp Val Pro Pro Ser Ser Gly Arg Ser
```

<210> SEQ ID NO 29
<211> LENGTH: 116
<212> TYPE: DNA
<213> ORGANISM: Artificial sequence
<220> FEATURE:
<223> OTHER INFORMATION: PCR primer MBP267

<400> SEQUENCE: 29

```
atactattgt aattcaaaaa aaaaaagcga atcttcccat gcctgttgct gctcttgaat      60
ggcgacagcc tattgcccca gtgttccctc aacaaccttg cgtacgctgc aggtcg        116
```

<210> SEQ ID NO 30
<211> LENGTH: 119
<212> TYPE: DNA
<213> ORGANISM: Artificial sequence
<220> FEATURE:
<223> OTHER INFORMATION: PCR Primer MBP268

<400> SEQUENCE: 30

```
acagttgtag tcacgtgcgc gccatgctga ctaatggcag ccgtcgttgg gcagaagaga      60
attagtatgg tacaggatac gctaattgcg ctccaactac atcgatgaat tcgagctcg     119
```

<210> SEQ ID NO 31
<211> LENGTH: 2723
<212> TYPE: DNA
<213> ORGANISM: Artificial Sequence
<220> FEATURE:
<223> OTHER INFORMATION: 5'-GSH1 5'UTR-KanMX-GSH1 5'UTR-GSH1 ORF
      fragment. Sequence amplified by MBP288 and MBP289 and used for
      GSH1 SNP reversion.

<400> SEQUENCE: 31

```
gattttatcg gtcaaagggg aaatcaatgc gaaagacagt aatgatgaga gaaaaactct      60
ccgtaaccac caagtttggt tcagcgcgac gagattttta tcgattatcg agaaaaatac     120
ctgtatatct acatttctat gtcagtgata tatacttctt agataagtta tgccaccagt     180
gcatacgctt acgcacacac acgtattctt gtgcacacgc ctgttacttc ttgcagacat     240
cagacatact attgtaattc aaaaaaaaaa agcgaatctt cccatgcctg ttgctgctct     300
tgaatggcga cagcctattg ccccagtgtt ccctcaacaa ccttgcgtac gctgcaggtc     360
gacggatccc cgggttaatt aaggcgcgcc agatctgttt agcttgcctc gtccccgccg     420
ggtcacccgg ccagcgacat ggaggcccag aatacccctc cttgacagtct tgacgtgcgc     480 agctcagggg catgatgtga ctgtcgcccg tacatttagc ccatacatcc ccatgtataa     540
tcatttgcat ccatacattt tgatggccgc acggcgcgaa gcaaaaatta cggctcctcg     600
ctgcagacct gcgagcaggg aaacgctccc ctcacagacg cgttgaattg tccccacgcc     660
gcgcccctgt agagaaatat aaaaggttag gatttgccac tgaggttctt ctttcatata     720
cttcctttta aaatcttgct aggatacagt tctcacatca catccgaaca taaacaacca     780
tgggtaagga aaagactcac gtttcgaggc cgcgattaaa ttccaacatg gatgctgatt     840
tatatgggta taaatgggct cgcgataatg tcgggcaatc aggtgcgaca atctatcgat     900
tgtatgggaa gcccgatgcg ccagagttgt ttctgaaaca tggcaaaggt agcgttgcca     960
atgatgttac agatgagatg gtcagactaa actggctgac ggaatttatg cctcttccga    1020
ccatcaagca ttttatccgt actcctgatg atgcatggtt actcaccact gcgatccccg    1080
gcaaaacagc attccaggta ttagaagaat atcctgattc aggtgaaaat attgttgatg    1140
```

-continued

```
cgctggcagt gttcctgcgc cggttgcatt cgattcctgt ttgtaattgt ccttttaaca    1200
gcgatcgcgt atttcgtctc gctcaggcgc aatcacgaat gaataacggt ttggttgatg    1260
cgagtgattt tgatgacgag cgtaatggct ggcctgttga acaagtctgg aaagaaatgc    1320
ataagctttt gccattctca ccggattcag tcgtcactca tggtgatttc tcacttgata    1380
accttatttt tgacgagggg aaattaatag gttgtattga tgttggacga gtcggaatcg    1440
cagaccgata ccaggatctt gccatcctat ggaactgcct cggtgagttt tctccttcat    1500
tacagaaacg cttttcaa aaatatggta ttgataatcc tgatatgaat aaattgcagt    1560
ttcatttgat gctcgatgag ttttctaat cagtactgac aataaaaga ttcttgtttt    1620 caagaacttg tcatttgtat agttttttta tattgtagtt gttctatttt aatcaaatgt    1680
tagcgtgatt tatattttt ttcgcctcga catcatctgc ccagatgcga agttaagtgc    1740
gcagaaagta atatcatgcg tcaatcgtat gtgaatgctg gtcgctatac tgctgtcgat    1800
tcgatactaa cgccgccatc cagtgtcgaa aacgagctcg aattcatcga tgtagttgga    1860
gcgcaattag cgtatcctgt accatactaa ttctcttctg cccaacgacg gctgccatta    1920
gtcagcatgg cgcgcacgtg actacaactg tggctggaaa ccttttcgtc ctccccggtt    1980
tttcagtgag ccgactctac tacaatgctt tttcattttt cactcagaaa aacctgcaat    2040
ttgccaaatt ggccatgctc tgtgcctccc ttgacaaagg acatcttccc tgtttataaa    2100
cggcggctta ccaaaagttg aagcttgttc ttgcctctta tgagtggagc aatcgattat    2160
attgaatcgt tgtgctggag tagttggatc tttccacgtg gtctcgagtc acttgtagaa    2220
gctgaaaatt gagcagattt agtatagggc tacattgtag ggtggtttag agtatcgaaa    2280
atatacatat agaagaataa aatgggactc ttagctttgg gcacgccttt gcagtggttt    2340
gagtctagga cgtacaatga acacataagg gatgaaggta tcgagcagtt gttgtatatt    2400
ttccaagctg ctggtaaaag agacaatgac cctcttttt ggggagacga gcttgagtac    2460
atggttgtag atttttgatga taaggagaga aattctatgc tcgacgtttg ccatgacaag    2520
atactcactg agcttaatat ggaggattcg tcccttttgtg aggctaacga tgtgagtttt    2580
caccctgagt atggccggta tatgttagag gcaacaccag cttctccata tttgaattac    2640
gtgggtagtt acgttgaggt taacatgcaa aaaagacgtg ccattgcaga atataagcta    2700
tctgaatatg cgagacaaga tag                                             2723
```

<210> SEQ ID NO 32
<211> LENGTH: 18
<212> TYPE: DNA
<213> ORGANISM: Artificial Sequence
<220> FEATURE:
<223> OTHER INFORMATION: PCR Primer MBP288

<400> SEQUENCE: 32

```
gattttatcg gtcaaagg                                                    18
```

<210> SEQ ID NO 33
<211> LENGTH: 20
<212> TYPE: DNA
<213> ORGANISM: Artificial sequence
<220> FEATURE:
<223> OTHER INFORMATION: PCR Primer MBP289

<400> SEQUENCE: 33

```
ctatcttgtc tcgcatattc                                                  20
```

<210> SEQ ID NO 34
<211> LENGTH: 20
<212> TYPE: DNA
<213> ORGANISM: Artificial Sequence
<220> FEATURE:
<223> OTHER INFORMATION: PCR Primer MBP290

<400> SEQUENCE: 34
tctcgagtca cttgtagaag                                              20

<210> SEQ ID NO 35
<211> LENGTH: 17
<212> TYPE: DNA
<213> ORGANISM: Artificial sequence
<220> FEATURE:
<223> OTHER INFORMATION: PCR Primer  MBP292

<400> SEQUENCE: 35
gagcccacat gcaagtt                                                 17

<210> SEQ ID NO 36
<211> LENGTH: 20
<212> TYPE: DNA
<213> ORGANISM: Artificial sequence
<220> FEATURE:
<223> OTHER INFORMATION: PCR Primer MBP291

<400> SEQUENCE: 36
gtagggtggt ttagagtatc                                              20

<210> SEQ ID NO 37
<211> LENGTH: 32
<212> TYPE: DNA
<213> ORGANISM: Artificial sequence
<220> FEATURE:
<223> OTHER INFORMATION: PCR Primer MBP393

<400> SEQUENCE: 37
tattatgaat tcaaatgttg agcccgaaga cg                                32

<210> SEQ ID NO 38
<211> LENGTH: 32
<212> TYPE: DNA
<213> ORGANISM: Artificial sequence
<220> FEATURE:
<223> OTHER INFORMATION: PCR Primer MBP396

<400> SEQUENCE: 38
tattataagc ttaaattagc gaagcaggtt cc                                32

<210> SEQ ID NO 39
<211> LENGTH: 32
<212> TYPE: DNA
<213> ORGANISM: Artificial sequence
<220> FEATURE:
<223> OTHER INFORMATION: PCR Primer MBP397

<400> SEQUENCE: 39
tattatgcat gccacgtatt cttgtgcaca cg                                32

<210> SEQ ID NO 40
<211> LENGTH: 32
<212> TYPE: DNA
<213> ORGANISM: Artificial sequence
<220> FEATURE:
<223> OTHER INFORMATION: PCR Primer MBP406

-continued

<400> SEQUENCE: 40
tattatgtcg actaccacct acaccaataa gc                                    32

<210> SEQ ID NO 41
<211> LENGTH: 19
<212> TYPE: PRT
<213> ORGANISM: Artificial Sequence
<220> FEATURE:
<223> OTHER INFORMATION: Modified invertase signal peptide
<220> FEATURE:
<221> NAME/KEY: MISC
<222> LOCATION: (7)..(7)
<223> OTHER INFORMATION: Xaa = Phe, Trp or Tyr
<220> FEATURE:
<221> NAME/KEY: MISC
<222> LOCATION: (8)..(8)
<223> OTHER INFORMATION: Xaa = Ile, Leu, Val, Ala or Met
<220> FEATURE:
<221> NAME/KEY: MISC
<222> LOCATION: (9)..(9)
<223> OTHER INFORMATION: Xaa = Leu, Val, Ala or Met
<220> FEATURE:
<221> NAME/KEY: MISC
<222> LOCATION: (10)..(10)
<223> OTHER INFORMATION: Xaa = Ser or Thr
<220> FEATURE:
<221> NAME/KEY: MISC
<222> LOCATION: (11)..(11)
<223> OTHER INFORMATION: Xaa = Ile, Val, Ala or Met

<400> SEQUENCE: 41

Met Leu Leu Gln Ala Phe Xaa Xaa Xaa Xaa Xaa Gly Phe Ala Ala Lys
1               5                   10                  15

Ile Ser Ala

<210> SEQ ID NO 42
<211> LENGTH: 19
<212> TYPE: PRT
<213> ORGANISM: Artificial sequence
<220> FEATURE:
<223> OTHER INFORMATION: Modified invertase signal peptide

<400> SEQUENCE: 42

Met Leu Leu Gln Ala Phe Phe Ile Val Ser Ile Gly Phe Ala Ala Lys
1               5                   10                  15

Ile Ser Ala

<210> SEQ ID NO 43
<211> LENGTH: 2118
<212> TYPE: DNA
<213> ORGANISM: Artificial Sequence
<220> FEATURE:
<223> OTHER INFORMATION: KanMX flanked on the 5' end by 300bp
      immediately upstream to the GSH1 ORF and on the 3' end by 300bp
      immediately downstream to the GSH1 ORF

<400> SEQUENCE: 43
ggtaccacaa tgcttttttca tttttcactc agaaaaacct gcaatttgcc aaattggcca      60
tgctctgtgc ctcccttgac aaaggacatc ttccctgttt ataaacggcg gcttaccaaa     120
agttgaagct tgttcttgcc tcttatgagt ggagcaatcg attatattga atcgttgtgc     180
tggagtagtt ggatctttcc acgtggtctc gagtcacttg tagaagctga aaattgagca     240
gatttagtat agggctacat tgtagggtgg tttagagtat cgaaaatata catatagaag     300
aataaacgta cgctgcaggt cgacggatcc ccgggttaat taaggcgcgc cagatctgtt     360

```
tagcttgcct cgtccccgcc gggtcacccg gccagcgaca tggaggccca gaatacc ctc      420
cttgacagtc ttgacgtgcg cagctcaggg gcatgatgtg actgtcgccc gtacattt ag      480
cccatacatc cccatgtata atcatttgca tccatacatt ttgatggccg cacggcgc ga      540
agcaaaaatt acggcctctc gctgcagacc tgcgagcagg gaaacgctcc cctcacag ac      600
gcgttgaatt gtccccacgc cgcgccctg tagagaaata taaaaggtta ggatttgc ca      660
ctgaggttct tctttcatat acttcctttt aaaatcttgc taggatacag ttctcaca tc      720
acatccgaac ataaacaacc atgggtaagg aaaagactca cgtttcgagg ccgcgatt aa      780
attccaacat ggatgctgat ttatatgggt ataaatgggc tcgcgataat gtcgggca at      840
caggtgcgac aatctatcga ttgtatggga agcccgatgc gccagagttg tttctgaa ac      900
atggcaaagg tagcgttgcc aatgatgtta cagatgagat ggtcagacta aactggct ga      960
cggaatttat gcctcttccg accatcaagc attttatccg tactcctgat gatgcatg gt     1020
tactcaccac tgcgatcccc ggcaaaacag cattccaggt attagaagaa tatcctga tt     1080
caggtgaaaa tattgttgat gcgctggcag tgttcctgcg ccggttgcat tcgattcc tg     1140
tttgtaattg tcctttta ac agcgatcgcg tatttcgtct cgctcaggcg caatcacg aa     1200
tgaataacgg tttggttgat gcgagtgatt ttgatgacga gcgtaatggc tggcctgt tg     1260
aacaagtctg gaaagaaatg cataagcttt tgccattctc accggattca gtcgtcac tc     1320
atggtgattt ctcacttgat aaccttattt ttgacgaggg gaaattaata ggttgtat tg     1380
atgttggacg agtcggaatc gcagaccgat accaggatct tgccatccta tggaactg cc     1440
tcggtgagtt ttctccttca ttacagaaac ggcttttttca aaaatatggt attgata atc     1500
ctgatatgaa taaattgcag tttcatttga tgctcgatga gttttctaa tcagtactg a     1560
caataaaaag attcttgttt tcaagaactt gtcatttgta tagttttttt atattgta gt     1620
tgttctattt taatcaaatg ttagcgtgat ttatattttt tttcgcctcg acatcatc tg     1680
cccagatgcg aagttaagtg cgcagaaagt aatatcatgc gtcaatcgta tgtgaatg ct     1740
ggtcgctata ctgctgtcga ttcgatacta acgccgccat ccagtgtcga aaacgagc tc     1800
gaattcatcg atactccttt tacttcggtt gtgaaagaaa gttgacatta tcgatttg gg     1860
tgacacggtg attgaaaaag caacgaccag tattatacct ctttttttta ttattcag tt     1920
tatatttttg caagtgatct taagcatttc tacacaaact tatgccaacg tgaccatt ta     1980
ttatttata tagcaaaaaa aaatgagggg ccttgcagaa caattgttgc gagtttcta a     2040
taacaagcac gtagaatatt ggccatttaa ttttctctt caatttatag aatggttgt g     2100
ttagtgacaa aaggtacc                                                 2118
```

<210> SEQ ID NO 44
<211> LENGTH: 1755
<212> TYPE: DNA
<213> ORGANISM: Artificial Sequence
<220> FEATURE:
<223> OTHER INFORMATION: Nucleic acid sequence encoding an albumin
      variant with mutations E492G, K573P, K574H and Q580K relative to
      wt HSA

<400> SEQUENCE: 44

```
gacgctcaca agtctgaagt tgctcacaga ttcaaggact taggcgagga aaacttc aaa       60
gctttggttt tgattgcatt cgctcaatac ttacaacaat gcccattcga agaccacg tc      120
aaattggtta acgaagttac tgaattcgca aagacttgcg ttgcagacga atccgcag aa      180
aactgcgaca gtctttgca cacattgttc ggcgacaaat tgtgcacagt tgctactt ta      240
```

```
agagaaacat acggcgaaat ggctgactgc tgcgctaaac aagagccaga aagaaacgaa    300
tgcttcttac aacacaagga cgacaaccca aacttaccaa gattggttag accagaagtt    360
gacgttatgt gcacagcatt ccacgacaac gaagaaactt tcttgaagaa gtacttgtac    420
gaaattgcta aagacaccc atacttctac gctccagaat tgttgttctt cgctaaaaga    480
tacaaggctg cattcacaga atgctgccaa gcagctgaca aggctgcttg cttgttacca    540
aagttggacg aattgagaga cgaaggcaag gcttcttctg ctaagcaaag gttgaaatgc    600
gcttctttgc aaaagttcgg cgagagagca ttcaaggcat gggctgttgc tcgtttatct    660
caaagattcc caaagcaga gttcgctgaa gtttccaagt tagttactga cttgacaaaa    720
gttcacactg aatgctgcca cggcgacttg ttagagtgcg ctgacgaccg tgctgactta    780
gccaaataca tttgcgaaaa ccaagactct atttcttcta agttaaagga gtgctgcgaa    840
aaaccgttgt tagagaaatc tcactgcatt gctgaagttg aaaacgacga aatgccagct    900
gacttgccat ctttagctgc tgacttcgtt gaatctaaag acgtttgcaa gaactacgca    960
gaagctaagg acgttttctt gggcatgttc ttatacgaat acgcaagaag acacccagac   1020
tactctgttg ttttgttgtt aagattggct aagacttacg aaactacatt agaaaagtgc   1080
tgcgctgccg cagacccaca cgaatgctac gctaaagttt cgacgagtt caagccattg   1140
gttgaagaac cacaaaactt gattaagcaa aactgcgagt tattcgaaca attgggcgaa   1200
tacaaattcc aaaacgcctt gttagttaga tacactaaga aagttccaca agtttcaact   1260
ccaacattgg ttgaagtttc tcgtaactta ggcaaggttg gctctaagtg ctgcaaacac   1320
ccagaggcta agcgtatgcc atgcgctgaa gactacttgt ctgttgtttt gaaccagtta   1380
tgcgttttgc acgagaagac tccagtttct gaccgtgtta ctaagtgctg cacagaatct   1440
ttagttaaca gacgtccatg cttctcagct ttgggtgttg acgaaactta cgttccaaaa   1500
gaattcaacg ctgaaacttt cacttttccac gctgacattt gcactttgtc tgaaaaggaa   1560
agacagatta agaaacaaac tgctttggtt gaattggtta agcacaagcc aaaggctact   1620
aaggaacaat gaaggctgt tatggacgac ttcgctgctt tcgttgaaaa gtgctgcaaa   1680
gctgacgaca aggaaacttg cttcgctgag gaaggcccac atttggttgc agcttcaaaa   1740
gctgctttgg gcttg                                                    1755
```

<210> SEQ ID NO 45
<211> LENGTH: 585
<212> TYPE: PRT
<213> ORGANISM: Artificial sequence
<220> FEATURE:
<223> OTHER INFORMATION: Albumin variant with mutations E492G, K573P,
      K574H and Q580K relative to wt HSA

<400> SEQUENCE: 45

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80
```

Arg Glu Thr Tyr Gly Glu Met Ala Asp Cys Cys Ala Lys Gln Pro
            85                  90                  95

Glu Arg Asn Glu Cys Phe Leu Gln His Lys Asp Asp Asn Pro Asn Leu
        100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Gly Val Asp Glu Thr
                485                 490                 495

Tyr Val Pro Lys Glu Phe Asn Ala Glu Thr Phe Thr Phe His Ala Asp

```
              500             505             510
Ile Cys Thr Leu Ser Glu Lys Glu Arg Gln Ile Lys Lys Gln Thr Ala
            515             520             525

Leu Val Glu Leu Val Lys His Lys Pro Lys Ala Thr Lys Glu Gln Leu
            530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Pro His Leu Val
                565             570             575

Ala Ala Ser Lys Ala Ala Leu Gly Leu
                580             585

<210> SEQ ID NO 46
<211> LENGTH: 2253
<212> TYPE: DNA
<213> ORGANISM: Artificial sequence
<220> FEATURE:
<223> OTHER INFORMATION: IL-1Ra fused to the C-terminus of HSA

<400> SEQUENCE: 46
gacgctcaca agtccgaagt cgctcacaga ttcaaggact tgggtgaaga aaacttcaag      60
gctttggtct tgatcgcttt cgctcaatac ttgcaacaat gtccattcga agatcacgtc     120
aagttggtca cgaagttac  cgaattcgct aagacttgtg ttgctgacga atccgcggaa     180
aactgtgaca agtccttgca caccttgttc ggtgataagt tgtgtactgt tgctaccttg     240
agagaaacct acggtgaaat ggctgactgt tgtgctaagc aagaaccaga agaaacgaa      300 tgtttcttgc aacacaagga cgacaaccca aacttgccaa gattggttag accagaagtt     360
gacgtcatgt gtactgcttt ccacgacaac aagaaaccct tcttgaagaa gtacttgtac     420
gaaattgcta agacacccc  atacttctac gctccagaat tgttgttctt cgctaagaga     480
tacaaggctg ctttcaccga atgttgtcaa gctgctgata aggctgcttg tttgttgcca     540
aagttggatg aattgagaga cgaaggtaag gcttcttccg ctaagcaaag attgaagtgt     600
gcttccttgc aaaagttcgg tgaaagagct ttcaaggctt gggctgtcgc tagattgtct     660
caaagattcc caaaggctga attcgctgaa gtttctaagt tggttactga cttgactaag     720
gttcacactg aatgttgtca cggtgacttg ttggaatgtg ctgatgacag agctgacttg     780
gctaagtaca tctgtgaaaa ccaagactct atctcttcca gttgaagga  atgttgtgaa     840 aagccattgt tggaaaagtc tcactgtatt gctgaagttg aaaacgatga aatgccagct     900
gacttgccat ctttggctgc tgacttcgtt gaatctaagg acgtttgtaa gaactacgct     960
gaagctaagg acgtcttctt gggtatgttc ttgtacgaat acgctagaag acacccagac    1020
tactccgttg tcttgttgtt gagattggct aagacctacg aaactaccct cgagaagtgt    1080
tgtgctgctg ctgacccaca cgaatgttac gctaaggttt tcgatgaatt caagccattg    1140
gtcgaagaac acaaaaactt gatcaagcaa actgtgaat  tgttcgaaca attgggtgaa    1200
tacaagttcc aaaacgcttt gttggttaga tacactaaga aggtcccaca agtctccacc    1260
ccaactttgg ttgaagtctc tagaaacttg ggtaaggtcg gttctaagtg ttgtaagcac    1320
ccagaagcta gagaatgcc  atgtgctgaa gattacttgt ccgtcgtttt gaaccaattg    1380
tgtgttttgc acgaaaagac cccagtctct gatagagtca ccaagtgttg tactgaatct    1440
ttggttaaca aagaccatg  tttctctgct ttggaagtcg acgaaactta cgttccaaag    1500
gaattcaacg ctgaaacttt caccttccac gctgatatct gtaccttgtc cgaaaaggaa    1560
```

```
agacaaatta agaagcaaac tgctttggtt gaattggtca agcacaagcc aaaggctact    1620
aaggaacaat tgaaggctgt catggatgat ttcgctgctt tcgttgaaaa gtgttgtaag    1680
gctgatgata aggaaacttg tttcgctgaa gaaggtaaga agttggtcgc tgcttcccaa    1740
gctgccttag gtttgggtgg ttctggtggt tccggtggtt ctggtggatc cggtggtcga    1800
ccctctggga gaaaatccag caagatgcaa gccttcagaa tctgggatgt taaccagaag    1860
accttctatc tgaggaacaa ccaactagtt gctggatact tgcaaggacc aaatgtcaat    1920
ttagaagaaa agatagatgt ggtacccatt gagcctcatg ctctgttctt gggaatccat    1980
ggagggaaga tgtgcctgtc ctgtgtcaag tctggtgatg agaccagact ccagctggag    2040
gcagttcaaa tcactgacct gagcgagaac agaaagcagg acaagcgctt cgccttcatc    2100
cgctcagaca gcggccccac caccagtttt gagtctgccg cctgcccgg ttggttcctc    2160 tgcacagcga tggaagctga ccagcccgtc agcctcacca atatgcctga cgaaggcgtc    2220
atggtcacca aattctactt ccaggaggac gag                                 2253
```

<210> SEQ ID NO 47
<211> LENGTH: 751
<212> TYPE: PRT
<213> ORGANISM: Artificial Sequence
<220> FEATURE:
<223> OTHER INFORMATION: IL-1Ra fused to the C-terminus of HSA

<400> SEQUENCE: 47

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240
```

-continued

Val His Thr Glu Cys Cys His Gly Asp Leu Glu Cys Ala Asp Asp
            245                 250                 255

Arg Ala Asp Leu Ala Lys Tyr Ile Cys Glu Asn Gln Asp Ser Ile Ser
        260                 265                 270

Ser Lys Leu Lys Glu Cys Cys Glu Lys Pro Leu Leu Glu Lys Ser His
    275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Ser Gly Gly Ser Gly
            580                 585                 590

Gly Ser Gly Gly Ser Gly Gly Arg Pro Ser Gly Arg Lys Ser Ser Lys
        595                 600                 605

Met Gln Ala Phe Arg Ile Trp Asp Val Asn Gln Lys Thr Phe Tyr Leu
610                 615                 620

Arg Asn Asn Gln Leu Val Ala Gly Tyr Leu Gln Gly Pro Asn Val Asn
625                 630                 635                 640

Leu Glu Glu Lys Ile Asp Val Val Pro Ile Glu Pro His Ala Leu Phe
                645                 650                 655

Leu Gly Ile His Gly Gly Lys Met Cys Leu Ser Cys Val Lys Ser Gly

```
            660                 665                 670
Asp Glu Thr Arg Leu Gln Leu Glu Ala Val Gln Ile Thr Asp Leu Ser
            675                 680                 685

Glu Asn Arg Lys Gln Asp Lys Arg Phe Ala Phe Ile Arg Ser Asp Ser
        690                 695                 700

Gly Pro Thr Thr Ser Phe Glu Ser Ala Ala Cys Pro Gly Trp Phe Leu
705                 710                 715                 720

Cys Thr Ala Met Glu Ala Asp Gln Pro Val Ser Leu Thr Asn Met Pro
                725                 730                 735

Asp Glu Gly Val Met Val Thr Lys Phe Tyr Phe Gln Glu Asp Glu
            740                 745                 750
```

<210> SEQ ID NO 48
<211> LENGTH: 756
<212> TYPE: DNA
<213> ORGANISM: Artificial Sequence
<220> FEATURE:
<223> OTHER INFORMATION: FLAG fused to the C-terminus of scFv

<400> SEQUENCE: 48

```
gaagttcaat tgttggaatc tggtggtggt ttggttcaac tggtggttc tttgagattg      60
tcttgtgctg cttctggttt tactttttct aattattgga tgtcttgggt tagacaagct    120
ccaggtaaag gtttggaatg ggtttccggt atttcaggta atggtggtta tacttatttt    180
gctgattcag ttaaagatag atttactatt tctagagata attctaaaaa taccttatat    240
ttgcaaatga actctttgag agcagaagat actgctgttt attactgtgc aggtggtgac    300
ggttctggtt ggagtttttg gggtcaaggt actctagtta ccgtttcttc aggtggtggt    360
ggttctggtg gaggtggatc aggtggtgga ggatctcaat cagttttgac tcaaccacca    420
tctgcttcag gtactccagg tcaaagagtt accatttctt gtactggttc ttcttctaat    480
attggtgcag gttacgatgt tcattggtat caacaattgc caggtactgc tccaaaattg    540
ttgatttatg gtaacaacaa tagaccatct ggtgtcccag atagattttc tggttctaaa    600
tctggtactt ctgcttcttt ggctatttct ggtttaagat cagaagatga agctgattac    660
tactgtgctc ttgggatga ctctttgtct ggtagagttt tcggtggtgg tactaaattg    720
accgttttgg gtgattataa agatgatgac gataaa                              756
```

<210> SEQ ID NO 49
<211> LENGTH: 252
<212> TYPE: PRT
<213> ORGANISM: Artificial Sequence
<220> FEATURE:
<223> OTHER INFORMATION: FLAG fused to the C-terminus of scFv

<400> SEQUENCE: 49

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ser Gly Ile Ser Gly Asn Gly Gly Tyr Thr Tyr Phe Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Gly Gly Asp Gly Ser Gly Trp Ser Phe Trp Gly Gln Gly Thr Leu
                100                 105                 110

Val Thr Val Ser Ser Gly Gly Gly Ser Gly Gly Gly Gly Ser Gly
            115                 120                 125

Gly Gly Gly Ser Gln Ser Val Leu Thr Gln Pro Pro Ser Ala Ser Gly
        130                 135                 140

Thr Pro Gly Gln Arg Val Thr Ile Ser Cys Thr Gly Ser Ser Ser Asn
145                 150                 155                 160

Ile Gly Ala Gly Tyr Asp Val His Trp Tyr Gln Gln Leu Pro Gly Thr
                165                 170                 175

Ala Pro Lys Leu Leu Ile Tyr Gly Asn Asn Asn Arg Pro Ser Gly Val
            180                 185                 190

Pro Asp Arg Phe Ser Gly Ser Lys Ser Gly Thr Ser Ala Ser Leu Ala
        195                 200                 205

Ile Ser Gly Leu Arg Ser Glu Asp Glu Ala Asp Tyr Tyr Cys Ala Ala
        210                 215                 220

Trp Asp Asp Ser Leu Ser Gly Arg Val Phe Gly Gly Gly Thr Lys Leu
225                 230                 235                 240

Thr Val Leu Gly Asp Tyr Lys Asp Asp Asp Lys
                245                 250

<210> SEQ ID NO 50
<211> LENGTH: 8
<212> TYPE: PRT
<213> ORGANISM: Artificial sequence
<220> FEATURE:
<223> OTHER INFORMATION: FLAG

<400> SEQUENCE: 50

Asp Tyr Lys Asp Asp Asp Asp Lys
1               5

<210> SEQ ID NO 51
<211> LENGTH: 30
<212> TYPE: PRT
<213> ORGANISM: Artificial sequence
<220> FEATURE:
<223> OTHER INFORMATION: GLP-1 fragment

<400> SEQUENCE: 51

His Ala Glu Gly Thr Phe Thr Ser Asp Val Ser Ser Tyr Leu Glu Gly
1               5                  10                  15

Gln Ala Ala Lys Glu Phe Ile Ala Trp Leu Val Lys Gly Arg
            20                  25                  30

<210> SEQ ID NO 52
<211> LENGTH: 60
<212> TYPE: PRT
<213> ORGANISM: Artificial sequence
<220> FEATURE:
<223> OTHER INFORMATION: Tandem repeat of GLP-1 fragment

<400> SEQUENCE: 52

His Gly Glu Gly Thr Phe Thr Ser Asp Val Ser Ser Tyr Leu Glu Gly
1               5                  10                  15

Gln Ala Ala Lys Glu Phe Ile Ala Trp Leu Val Lys Gly Arg His Gly
            20                  25                  30
```

-continued

```
Glu Gly Thr Phe Thr Ser Asp Val Ser Ser Tyr Leu Glu Gly Gln Ala
        35                  40                  45
Ala Lys Glu Phe Ile Ala Trp Leu Val Lys Gly Arg
 50                  55                  60
```